US010426468B2

(12) United States Patent
Contini et al.

(10) Patent No.: US 10,426,468 B2
(45) Date of Patent: Oct. 1, 2019

(54) HANDHELD ELECTROMECHANICAL SURGICAL SYSTEM

(71) Applicant: Covidien LP, Mansfield, MA (US)

(72) Inventors: Elizabeth Contini, Trumbull, CT (US); Kelly Valentine, New Britain, CT (US); Thomas Wingardner, North Haven, CT (US); David McCuen, Stratford, CT (US); Matthew Chowaniec, Madison, CT (US); John Beardsley, Wallingford, CT (US); Russell Pribanic, Roxbury, CT (US); Xingrui Chen, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 595 days.

(21) Appl. No.: 15/096,399

(22) Filed: Apr. 12, 2016

(65) Prior Publication Data
US 2016/0310134 A1 Oct. 27, 2016

Related U.S. Application Data

(60) Provisional application No. 62/291,775, filed on Feb. 5, 2016, provisional application No. 62/151,145, filed
(Continued)

(51) Int. Cl.
  *A61B 17/072* (2006.01)
  *A61B 17/00* (2006.01)
  *A61B 90/00* (2016.01)

(52) U.S. Cl.
  CPC .................. *A61B 17/07207* (2013.01); *A61B 2017/0046* (2013.01); *A61B 2017/00398* (2013.01);
(Continued)

(58) Field of Classification Search
  CPC ...... A61B 17/07207; A61B 2090/0808; A61B 2090/0813; A61B 2017/00398;
(Continued)

(56) References Cited

U.S. PATENT DOCUMENTS 2,777,340 A  1/1957  Hettwer et al.
2,957,353 A  10/1960 Babacz
(Continued)

FOREIGN PATENT DOCUMENTS

CA      2451558 A1    1/2003
CN    102247177 A    11/2011
(Continued)

OTHER PUBLICATIONS

Notification of Transmittal of the International Search Report and the Written Opinion of the International Searching Authority issued in corresponding application No. PCT/US2016/027042 dated Jul. 12, 2016.
(Continued)

*Primary Examiner* — Michelle Lopez

(57) ABSTRACT

A handheld electromechanical surgical device includes a non-sterile power-pack having a drive component(s) including a rotatable drive shaft extending therefrom, a main processor configured to control each drive component, a battery configured to power each drive component, an electrical receptacle, and a control interface(s) configured to control a functionality of the drive component. A sterile outer shell housing is configured to removably encase the power-pack to define a sterile barrier thus enabling use in a surgical environment without breaking sterility. The outer shell housing includes a coupler configured to transmit a rotation from the rotatable drive shaft through the outer shell housing, a control button(s) operatively positioned such that actuation of the control button actuates the control interface,
(Continued)

and a pass-through connector configured to transmit electrical communications from the electrical receptacle through the outer shell housing.

18 Claims, 56 Drawing Sheets

Related U.S. Application Data on Apr. 22, 2015, provisional application No. 62/151,171, filed on Apr. 22, 2015, provisional application No. 62/151,183, filed on Apr. 22, 2015, provisional application No. 62/151,196, filed on Apr. 22, 2015, provisional application No. 62/151,206, filed on Apr. 22, 2015, provisional application No. 62/151,224, filed on Apr. 22, 2015, provisional application No. 62/151,235, filed on Apr. 22, 2015, provisional application No. 62/151,246, filed on Apr. 22, 2015, provisional application No. 62/151,255, filed on Apr. 22, 2015, provisional application No. 62/151,261, filed on Apr. 22, 2015, provisional application No. 62/151,266, filed on Apr. 22, 2015, provisional application No. 62/151,273, filed on Apr. 22, 2015.

(52) U.S. Cl.
CPC ........... *A61B 2017/00464* (2013.01); *A61B 2017/00734* (2013.01); *A61B 2090/0808* (2016.02); *A61B 2090/0813* (2016.02)

(58) Field of Classification Search
CPC .. A61B 2017/0046; A61B 2017/00464; A61B 2017/00734
USPC ...................................................... 227/175.1
See application file for complete search history.

(56) References Cited

U.S. PATENT DOCUMENTS

| | | | |
|---|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,275,612 A | 1/1994 | Bales, Jr. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,356,064 A | 10/1994 | Green et al. |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen |
| 5,402,768 A | 4/1995 | Adair |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,573,529 A | 11/1996 | Haak et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,651,780 A | 7/1997 | Jackson et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,704,892 A | 1/1998 | Adair |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,871,493 A | 2/1999 | Sjostrom et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 5,993,470 A | 11/1999 | Yoon |
| 6,010,054 A | 1/2000 | Johnson et al. |
| 6,017,354 A | 1/2000 | Culp et al. |
| 6,025,683 A | 2/2000 | Philipp |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,132,368 A | 10/2000 | Cooper |
| 6,165,169 A | 12/2000 | Panescu et al. |
| 6,223,440 B1 | 5/2001 | Rashman |
| 6,233,504 B1 | 5/2001 | Das et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,346,072 B1 | 2/2002 | Cooper |
| 6,348,061 B1 | 2/2002 | Whitman |
| 6,368,324 B1 | 4/2002 | Dinger et al. |
| 6,371,909 B1 | 4/2002 | Hoeg et al. |
| 6,377,008 B1 | 4/2002 | Hirata |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,494,877 B2 | 12/2002 | Odell et al. |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |

(56) References Cited

U.S. PATENT DOCUMENTS

| | | |
|---|---|---|
| 6,668,751 B1 | 12/2003 | Henke |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| 7,048,745 B2 | 5/2006 | Tierney et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,154,378 B1 | 12/2006 | Ertas et al. |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,357,774 B2 | 4/2008 | Cooper |
| 7,364,061 B2 | 4/2008 | Swayze et al. |
| 7,364,582 B2 | 4/2008 | Lee |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,498,950 B1 | 3/2009 | Ertas et al. |
| 7,524,320 B2 | 4/2009 | Tierney et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,638,958 B2 | 12/2009 | Philipp et al. |
| 7,641,093 B2 | 1/2010 | Doll et al. |
| 7,644,848 B2 | 1/2010 | Swayze et al. |
| 7,666,191 B2 | 2/2010 | Orban, III et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,699,855 B2 | 4/2010 | Anderson et al. |
| 7,721,931 B2 | 5/2010 | Shelton, IV et al. |
| 7,721,936 B2 | 5/2010 | Shalton, IV et al. |
| 7,727,244 B2 | 6/2010 | Orban, III et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,784,663 B2 | 8/2010 | Shelton, IV |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,885 B2 | 10/2010 | Cooper |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,886,743 B2 | 2/2011 | Cooper et al. |
| 7,900,805 B2 | 3/2011 | Shelton, IV et al. |
| 7,905,886 B1 | 3/2011 | Curran et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,105,338 B2 | 1/2012 | Anderson et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,161,977 B2 | 4/2012 | Shelton, IV et al. |
| 8,167,185 B2 | 5/2012 | Shelton, IV et al. |
| 8,182,469 B2 | 5/2012 | Anderson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,202,278 B2 | 6/2012 | Orban, III et al. |
| 8,206,406 B2 | 6/2012 | Orban, III |
| 8,216,250 B2 | 7/2012 | Orban, III et al. |
| 8,220,367 B2 | 7/2012 | Hsu |
| 8,235,273 B2 | 8/2012 | Olson et al. |
| 8,241,322 B2 | 8/2012 | Whitman et al. |
| 8,259,186 B2 | 9/2012 | Kiyoshige |
| 8,272,554 B2 | 9/2012 | Whitman et al. |
| 8,273,076 B2 | 9/2012 | Devengenzo et al. |
| 8,292,150 B2 | 10/2012 | Bryant |
| 8,292,888 B2 | 10/2012 | Whitman |
| 8,308,043 B2 | 11/2012 | Bindra et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,357,158 B2 | 1/2013 | McKenna et al. |

(56) References Cited

U.S. PATENT DOCUMENTS

| | | |
|---|---|---|
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,397,971 B2 | 3/2013 | Yates et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,439,939 B2 | 5/2013 | Deville et al. |
| 8,444,662 B2 | 5/2013 | Palmer et al. |
| 8,453,907 B2 | 6/2013 | Laurent et al. |
| 8,454,585 B2 | 6/2013 | Whitman |
| 8,459,520 B2 | 6/2013 | Giordano et al. |
| 8,491,581 B2 | 7/2013 | Deville et al. |
| 8,505,802 B2 | 8/2013 | Viola et al. |
| 8,517,241 B2 | 8/2013 | Nicholas et al. |
| 8,517,243 B2 | 8/2013 | Giordano et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,596,515 B2 | 12/2013 | Okoniewski |
| 8,602,287 B2 | 12/2013 | Yates et al. |
| 8,623,000 B2 | 1/2014 | Humayun et al. |
| 8,627,995 B2 | 1/2014 | Smith et al. |
| 8,628,518 B2 | 1/2014 | Blumenkranz et al. |
| 8,632,463 B2 | 1/2014 | Drinan et al. |
| 8,632,535 B2 | 1/2014 | Shelton, IV et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,894,647 B2 * | 11/2014 | Beardsley ......... A61B 17/07207 606/42 |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,072,523 B2 | 7/2015 | Houser et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 * | 5/2011 | Malinouskas ......... A61B 17/068 606/1 |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |

(56) References Cited

U.S. PATENT DOCUMENTS

| | | |
|---|---|---|
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0080477 A1 | 4/2012 | Leimbach et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0265230 A1 | 10/2012 | Yates et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005677 A1 | 1/2014 | Shelton, IV et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| CN | 103230284 A | 8/2013 |
| DE | 102008053842 A1 | 5/2010 |
| EP | 0705571 A1 | 4/1996 |
| EP | 1769754 A1 | 4/2007 |
| EP | 2316345 A1 | 5/2011 |
| EP | 2614782 A2 | 7/2013 |
| EP | 2668910 A2 | 12/2013 |
| EP | 3005954 A1 | 4/2016 |
| EP | 3011910 A1 | 4/2016 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |
| WO | 2016171947 A1 | 10/2016 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.

(56) References Cited

OTHER PUBLICATIONS

European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action dated Dec. 5, 2019 (with English translation), corresponding to Chinese Application No. 201510807574.4; 17 total pages.
European Search Report dated Nov. 29, 2018, corresponding to counterpart European Application No. 16783602.2; 7 pages.
European Search Report dated Oct. 25, 2018, corresponding to counterpart European Application No. 18175484.7; 6 pages.

* cited by examiner

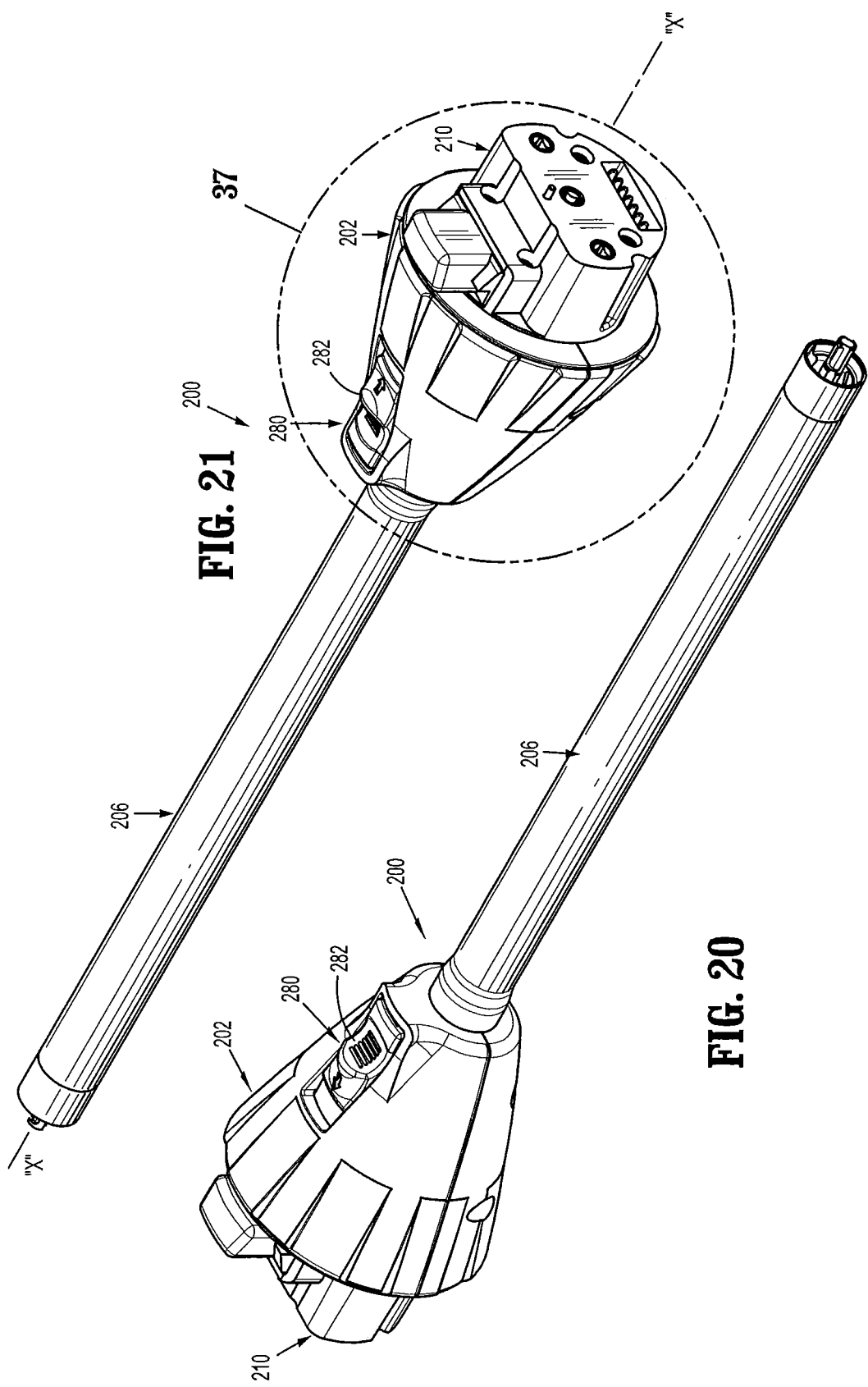

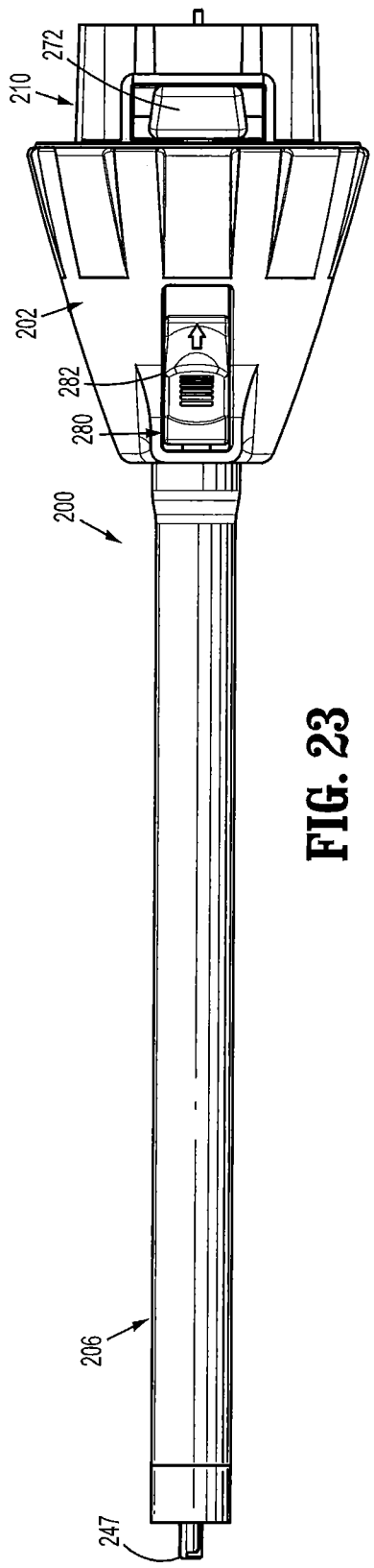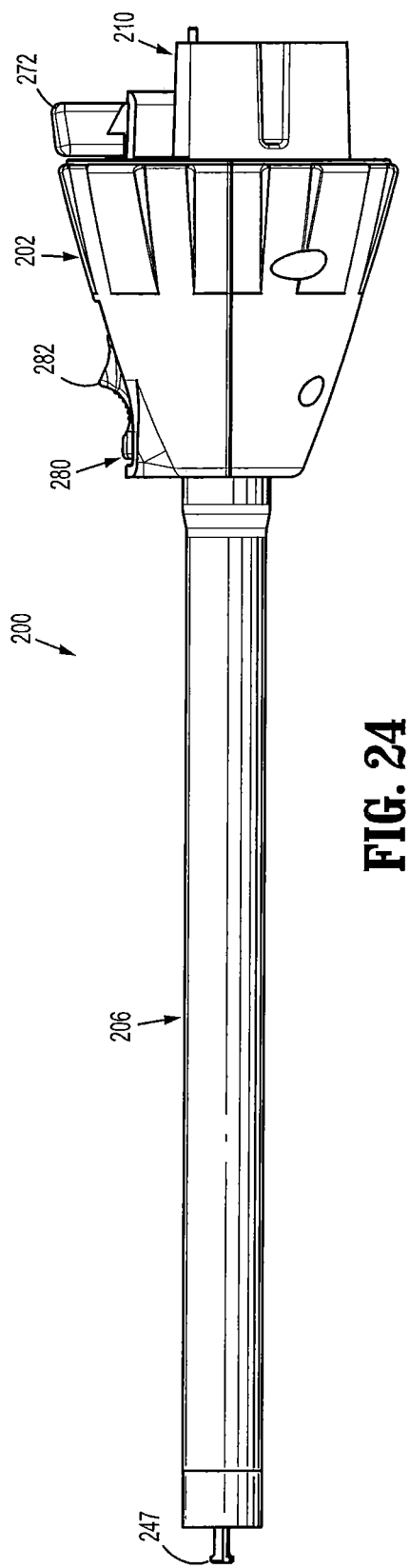

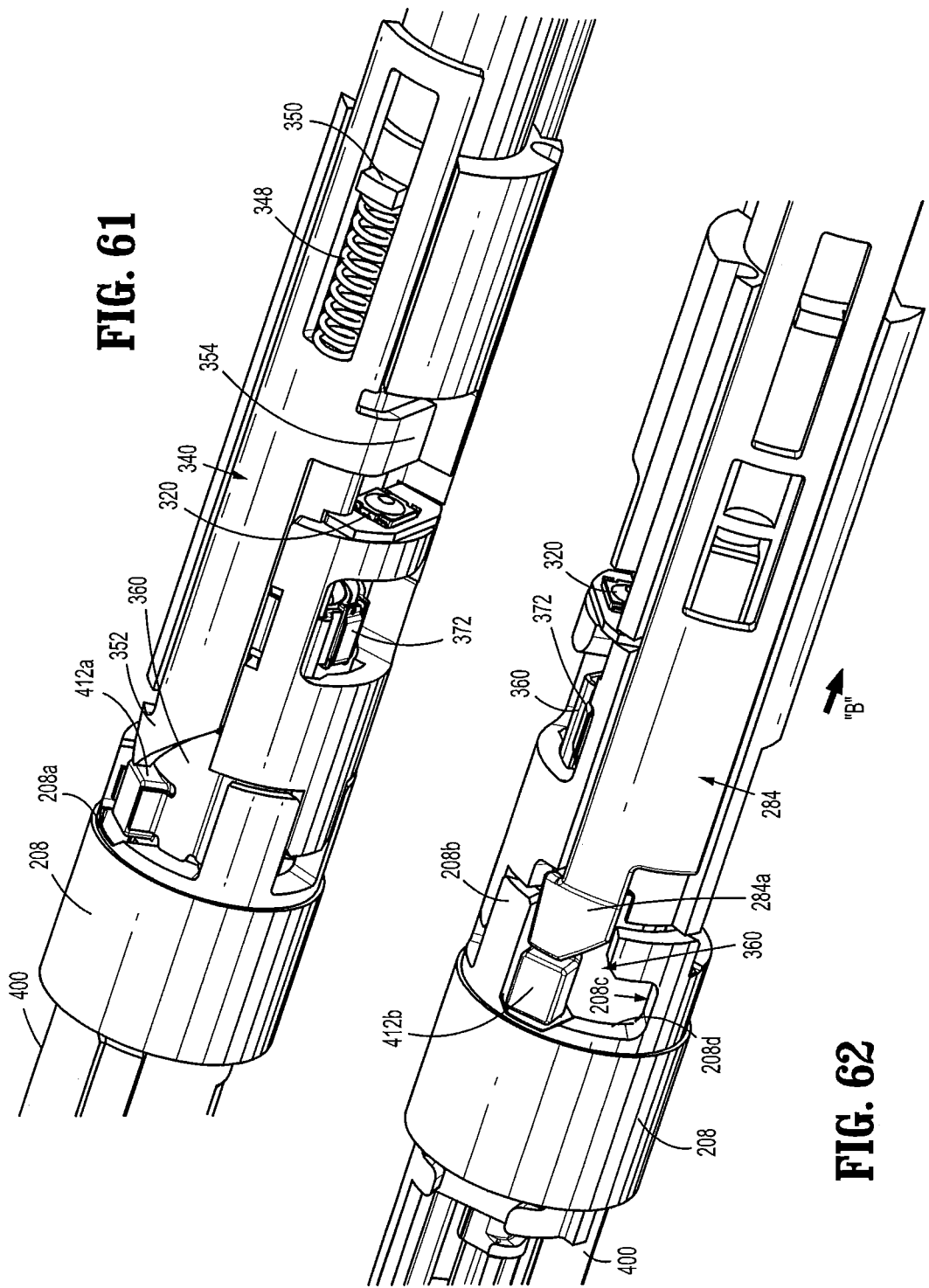

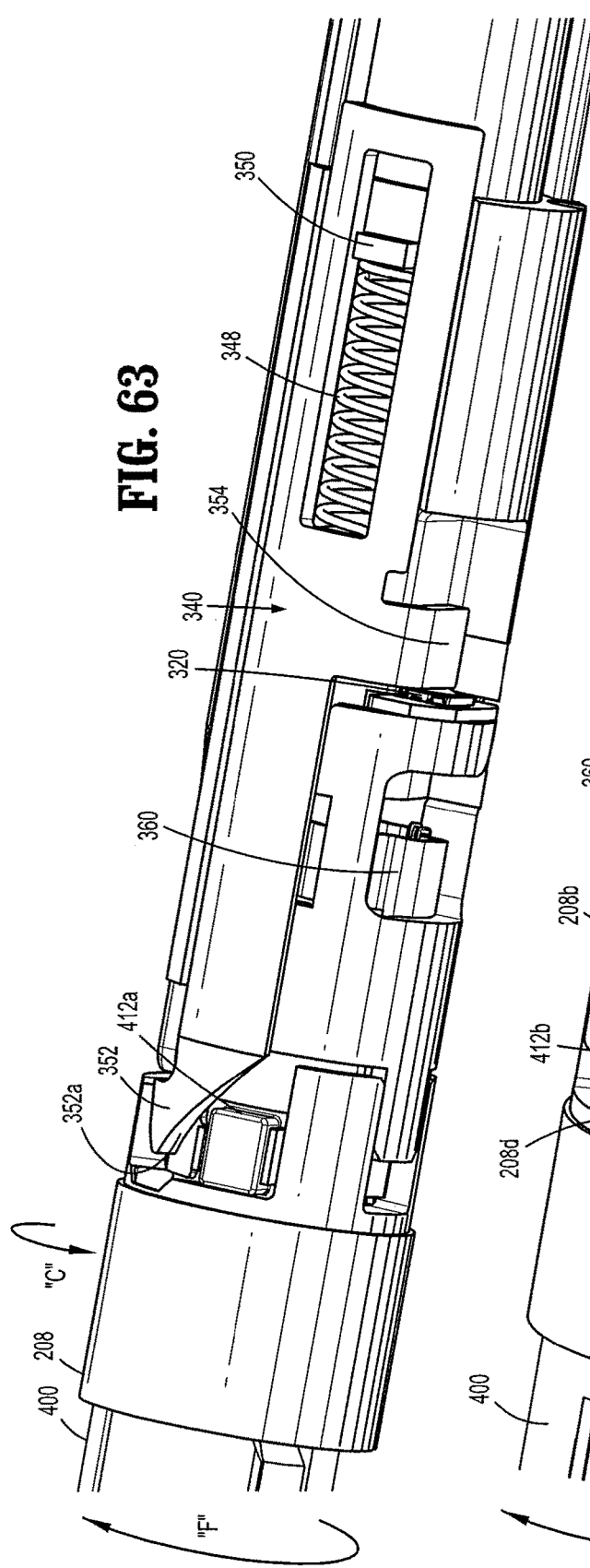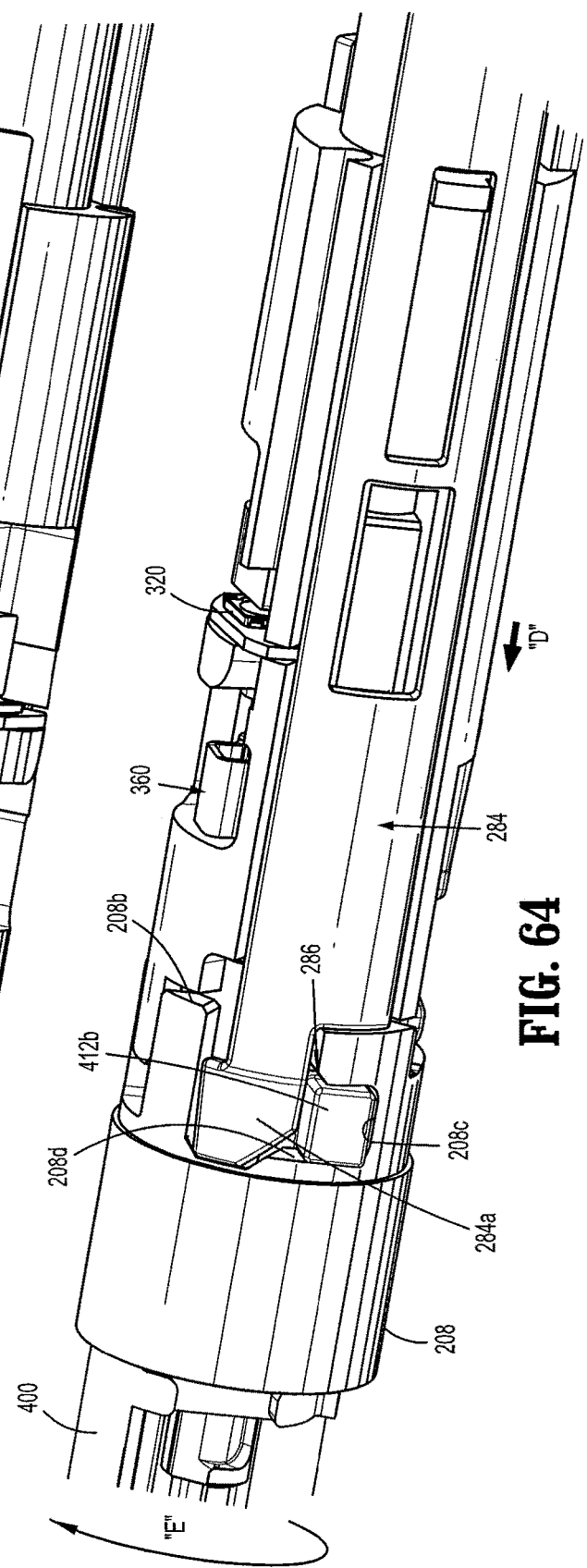

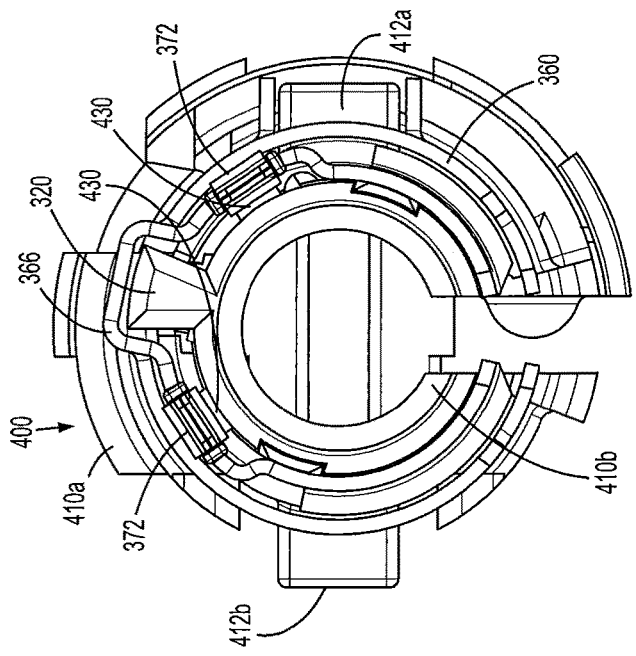
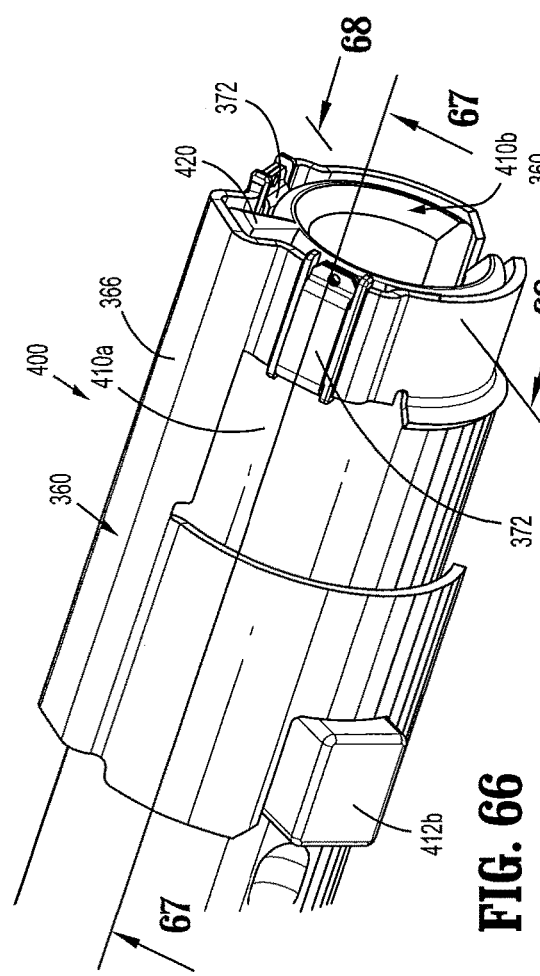
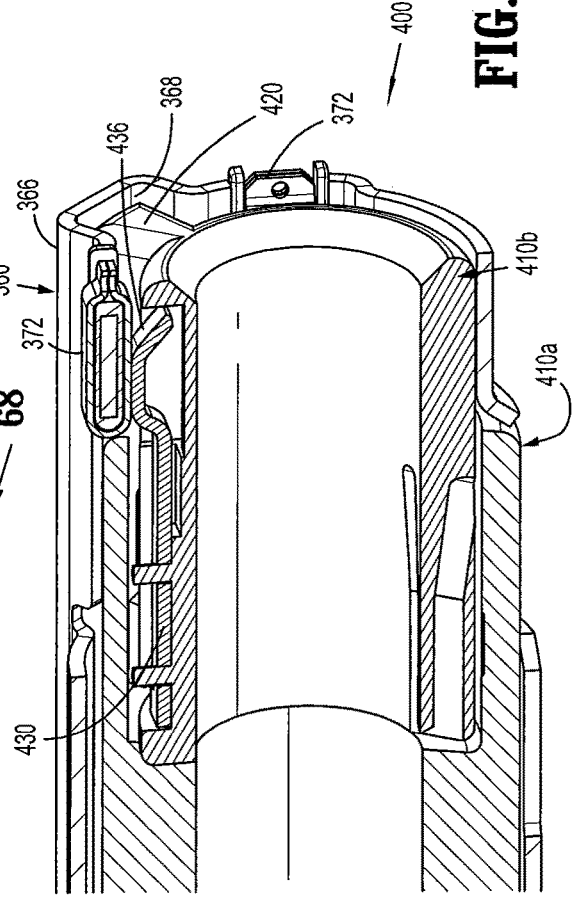
FIG. 68
FIG. 67
FIG. 66

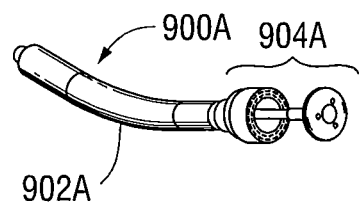
FIG. 69A
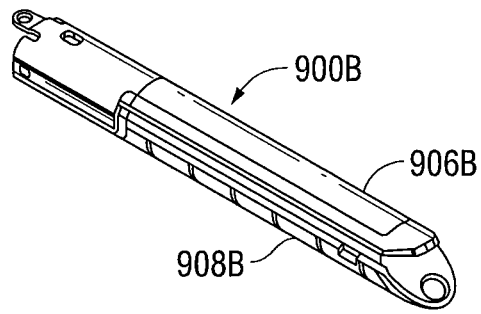
FIG. 69B1
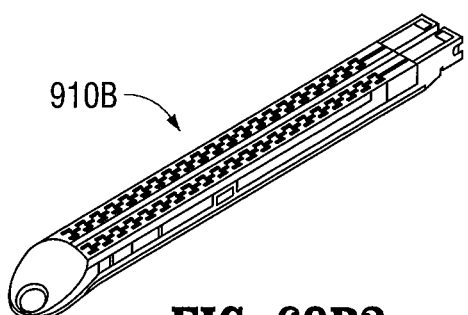
FIG. 69B2
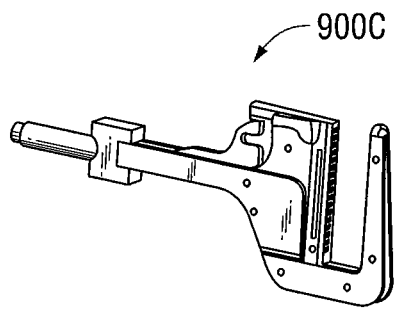
FIG. 69C
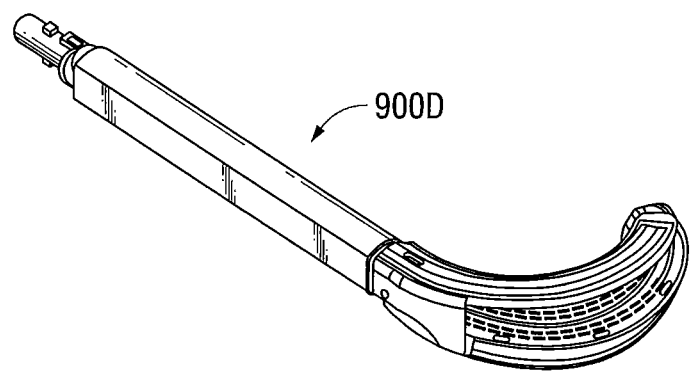
FIG. 69D

HANDHELD ELECTROMECHANICAL SURGICAL SYSTEM

CROSS-REFERENCE TO RELATED APPLICATIONS

This application claims the benefit of, and priority to, U.S. Provisional Patent Application No. 62/291,775, filed on Feb. 5, 2016, and U.S. Provisional Patent Application Nos. 62/151,145; 62/151,171; 62/151,183; 62/151,196; 62/151,206; 62/151,224; 62/151,235; 62/151,246; 62/151,255; 62/151,261; 62/151,266; and 62/151,273, each of which was filed on Apr. 22, 2015, the entire contents of each of which are incorporated herein by reference.

BACKGROUND

1. Technical Field

The present disclosure relates to surgical devices. More specifically, the present disclosure relates to handheld electromechanical surgical systems for performing surgical procedures.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary powered drive systems for operating and/or manipulating the surgical device. In many instances the surgical devices include a powered handle assembly, which is reusable, and a disposable end effector or the like that is selectively connected to the powered handle assembly prior to use and then disconnected from the end effector following use in order to be disposed of or in some instances sterilized for re-use.

The use of powered electro and endomechanical surgical staplers, including intelligent battery power, has grown tremendously over the past few decades. Advanced technology and informatics within these intelligent battery-powered stapling devices provide the ability to gather clinical data and drive design improvements to ultimately improve patient outcomes. Accordingly, a need exists to evaluate conditions that affect staple formation with the intention of building a more intelligent stapling algorithm.

SUMMARY

A handheld electromechanical surgical device provided in accordance with aspects of the present disclosure includes a non-sterile power-pack and a sterile outer shell housing. The non-sterile power-pack includes at least one drive component each having a rotatable drive shaft extending therefrom, a main processor coupled to the at least one drive component and configured to control each drive component, a battery coupled to the main processor and the at least one drive component and configured to power each drive component, an electrical receptacle coupled to the main processor, and at least one control interface coupled to the main processor. The at least one control interface is actuatable to direct the main processor to control a functionality of at least one of the at least one drive component. The sterile outer shell housing is configured to removably encase the power-pack to define a sterile barrier between the power-pack and an exterior of the outer shell housing, thus enabling use thereof in a surgical environment without breaking sterility. The outer shell housing includes a coupler configured to transmit a rotation from the rotatable drive shaft of each drive component through the outer shell housing, at least one control button in operative registration with each of the at least one control interfaces such that actuation of the at least one control button actuates the at least one control interface in operative registration therewith, and a pass-through connector configured to transmit electrical communications from the electrical receptacle through the outer shell housing.

In aspects, the coupler transmits a rotation from the rotatable drive shaft of each drive component through the outer shell housing without breaking the sterile barrier.

In aspects, the at least one control button actuates the at least one control interface in operative registration therewith without breaking the sterile barrier.

In aspects, the pass-through connector transmits electrical communications from the electrical receptacle through the outer shell housing without breaking the sterile barrier.

In aspects, the outer shell housing further includes a barrier plate assembly incorporating the coupler and the pass-through connector. In such aspects, the coupler may include a plurality of rotatable coupling shafts supported on the barrier plate assembly. Each rotatable coupling shaft includes a proximal end configured to operably couple to a respective rotatable drive shaft to receive rotative forces therefrom, and a distal end projecting from the outer shell housing.

In aspects, an adapter assembly is selectively connectable to the outer shell housing in operable engagement with the coupler and the pass-through connector to enable a rotation from the rotatable drive shaft of each drive component to be transmitted through the outer shell housing to the adapter assembly and to enable electrical communications from the electrical receptacle to be transmitted through the outer shell housing to the adapter assembly. In such aspects, the adapter assembly may include a housing configured to selectively connect to the outer shell housing in operable engagement with the coupler and the pass-through connector, an outer tube having a proximal end supported by the housing and a distal end, and at least one transmitting/converting assembly extending between the proximal and distal ends of the outer tube.

In aspects, a loading unit is be connected to the distal end of the outer tube of the adapter and configured such that the at least one transmitting/converting assembly effects an operation of the loading unit in response to rotation of one of the rotatable drive shafts of the power-pack. In such aspects, the adapter assembly may include an electrical connection to enable electrical communication between the electrical receptacle of the power-pack and the loading unit.

Additionally or alternatively, the loading unit may be selectively connectable with the distal end of the outer tube of the adapter.

In aspects, the power-pack includes an inner housing enclosing each drive component, the main processor, and the battery. The inner housing including the at least one control interface and the electrical receptacle disposed thereon.

In aspects, the at least one drive component is a motor.

Another handheld electromechanical surgical device provided in accordance with aspects of the present disclosure includes a non-sterile power-pack, a sterile outer shell housing, an adapter assembly, and a loading unit. The power-pack includes at least one drive component, a main processor coupled to each drive component, a battery coupled to the main processor and each drive component, an electrical receptacle coupled to the main processor, and at least one control interface coupled to the main processor. The sterile outer shell housing is configured to removably encase the power-pack to define a sterile barrier between the power-pack and an exterior of the outer shell housing, thus enabling use thereof in a surgical environment without breaking sterility. The outer shell housing includes a coupler configured to transmit an output from each drive component through the outer shell housing, at least one control button in operative registration with each of the at least one control interfaces such that actuation of the at least one control button actuates the at least one control interface in operative registration therewith, and a pass-through connector configured to transmit electrical communications from the electrical receptacle through the outer shell housing. The adapter assembly is connected to the outer shell housing in operable engagement with the coupler and the pass-through connector to enable an output from each motor to be transmitted through the outer shell housing to the adapter assembly and to enable electrical communications from the electrical receptacle to be transmitted through the outer shell housing to the adapter assembly. The loading unit is connected to the adapter assembly such that the adapter assembly is configured to effect an operation of the loading unit in response to an output from at least one of the at least one drive component of the power-pack and to enable electrical communication between the electrical receptacle of the power-pack and the loading unit.

In aspects, the adapter and/or the loading unit is selectively connectable.

In aspects, the coupler transmits an output from each drive component through the outer shell housing without breaking the sterile barrier.

In aspects, the at least one control button actuates the at least one control interface in operative registration therewith without breaking the sterile barrier.

In aspects, the pass-through connector transmits electrical communications from the electrical receptacle through the outer shell housing without breaking the sterile barrier.

In aspects, the at least one drive component includes a plurality of motors.

A method of operating a handheld electromechanical surgical device provided in accordance with the present disclosure includes encasing a non-sterile power-pack within a sterile outer shell housing to establish a sterile barrier between the power-pack and an exterior of the outer shell housing to enable use thereof in a surgical environment without breaking sterility, engaging an adapter with the outer shell housing, establishing electrical contact between a main processor of the power-pack and the adapter without breaking the sterile barrier, and mechanically coupling an output of each drive component of the power-pack with the adapter without breaking the sterile barrier.

In aspects, the method further includes establishing electrical contact between the main processor and the outer shell housing upon encasing the power-pack within the outer shell housing, without breaking the sterile barrier.

In aspects, the method further includes attempting to establish communication between the main processor and the outer shell housing via the electrical contact therebetween, and inhibiting at least one operation of the power-pack if electrical communication cannot be established or electrical communication indicates that the outer shell housing is invalid.

In aspects, the method further includes establishing operative registration between at least one control button of the outer shell housing and the at least one control interface of the power-pack upon encasing the power-pack within the outer shell housing, without breaking the sterile barrier.

In aspects, the method further includes actuating one of the at least one control buttons of the outer shell housing to thereby actuate a corresponding one of the at least one control interfaces of the power-pack without breaking the sterile barrier.

In aspects, the method further includes transmitting a mechanical output of at least one of the at least one drive component through the outer shell housing to the adapter without breaking the sterile barrier. The mechanical output is produced in response to the actuation of the at least one control button.

In aspects, the method further includes attempting to establish communication between the main processor and the adapter via the electrical contact therebetween, and inhibiting at least one operation of the power-pack if electrical communication cannot be established or the electrical communication indicates that the adapter is invalid.

In aspects, the at least one drive component includes a plurality of motors. In such aspects, the at least one operation is driving at least one of the plurality of motors.

In aspects, the method further includes engaging a loading unit with the adapter. Additionally, the method may include establishing electrical contact between the main processor and the loading unit upon engaging the loading unit with the adapter, without breaking the sterile barrier.

In aspects, the method further includes attempting to establish communication between the main processor and the loading unit via the electrical contact therebetween, and inhibiting at least one operation of the power-pack if electrical communication cannot be established or the electrical communication indicates that the loading unit is invalid.

In aspects, the method further includes transmitting a mechanical output of at least one of the at least one drive components through the outer shell housing to the adapter without breaking the sterile barrier, and effecting an operation of the loading unit in response to transmission of the mechanical output to the adapter. Such operation may include rotating the loading unit relative to the adapter, articulating the loading unit relative to the adapter, closing the loading unit, opening the loading unit, and/or firing the loading unit.

Another method of operating a handheld electromechanical surgical device provided in accordance with aspects of the present disclosure includes encasing a non-sterile power-pack within a sterile outer shell housing to establish a sterile barrier between the power-pack and an exterior of the outer shell housing to enable use thereof in a surgical environment without breaking sterility, establishing electrical contact between a main processor of the power-pack and the outer shell housing upon encasing the power-pack within the outer shell housing, without breaking the sterile barrier, validating the outer shell housing, engaging an adapter with the outer shell housing, establishing electrical contact between the main processor and the adapter upon engaging the adapter with the outer shell housing, without breaking the sterile barrier, mechanically coupling an output of each drive component of the power-pack with the adapter upon engaging the adapter with the outer shell housing, without breaking the sterile barrier, validating the adapter, engaging a loading unit with the adapter, establishing electrical contact between the main processor and the loading upon engaging the loading unit with the adapter, without breaking the sterile barrier, and validating the loading unit.

In aspects, the method further includes inhibiting at least one operation of the power-pack if validating the outer shell housing, validating the adapter, or validating the loading unit fails.

In aspects the method further includes establishing operative registration between at least one control button of the outer shell housing and the at least one control interface of the power-pack upon encasing the power-pack within the outer shell housing, without breaking the sterile barrier.

In aspects, the method further includes actuating one of the at least one control buttons of the outer shell housing to thereby actuate a corresponding one of the at least one control interfaces of the power-pack without breaking the sterile barrier.

In aspects, the method further includes transmitting a mechanical output of at least one of the at least one drive component through the outer shell housing to the adapter without breaking the sterile barrier. The mechanical output is produced in response to the actuation of the at least one control button.

In aspects, the method further includes effecting an operation of the loading unit in response to transmission of the mechanical output to the adapter. Such operation may include rotating the loading unit relative to the adapter, articulating the loading unit relative to the adapter, closing the loading unit, opening the loading unit, or firing the loading unit.

Another handheld electromechanical surgical device provided in accordance with aspects of the present disclosure includes a power-pack including a power-pack memory, at least one drive component, a battery having a first memory, a main processor, and a communication bus system coupled to the main processor. The communication bus system establishes communication between the main processor and the first memory. The device further includes an outer shell housing including a second memory. The outer shell housing is configured to removably encase the power-pack therein. The second memory is electrically coupled with the communication bus system to establish communication between the main processor and the second memory upon encasing the power-pack within the outer shell housing. The device also includes an adapter including a third memory. The adapter is configured to removably attach to the outer shell housing. The third memory is electrically coupled with the communication bus system to establish communication between the main processor and the third memory upon attachment of the adapter to the outer shell housing with the power-pack encased within the outer shell housing.

In aspects, the power-pack includes a non-transitory, computer-readable storage medium storing instructions that, when executed by the main processor, cause the power-pack to determine whether communication between the main processor and the first memory across the communication bus system is established. If communication is established, the power-pack obtains a battery identifier from the first memory across the communication bus system, stores the battery identifier in the power-pack memory, and inhibits use of the power-pack with any other battery. Further, if communication is established, the power-pack may be further caused to perform at least one test on the battery, e.g., a battery capacity test, a battery temperature test, or a battery end-of-life test.

In aspects, the communication bus system includes a first communication bus that establishes the communication between the main processor and the first memory.

In aspects, determining whether communication between the main processor and the first memory across the first communication bus is established includes monitoring the first communication bus at a minimum rate of 1 Hz.

In aspects, the power-pack includes a non-transitory, computer-readable storage medium storing instructions that, when executed by the main processor, cause the power-pack to determine whether communication between the main processor and the second memory across the communication bus system is established, and, if communication is established, obtain an outer shell housing identifier from the second memory across the communication bus system, store the outer shell housing identifier in the power-pack memory, and mark the outer shell housing as used in the second memory to inhibit reuse of the outer shell housing.

In aspects, the communication bus system includes a second communication bus that establishes the communication between the main processor and the second memory.

In aspects, determining whether communication between the main processor and the second memory across the second communication bus is established includes monitoring the second communication bus at a minimum rate of 1 Hz.

In aspects, the power-pack includes a non-transitory, computer-readable storage medium storing instructions that, when executed by the main processor, cause the power-pack to determine whether communication between the main processor and the third memory across the communication bus system is established, and, if communication is established, obtain an adapter identifier from the third memory across the communication bus system, determine whether the adapter identifier is valid, and obtain at least one counter value from the third memory across the communication bus system.

In aspects, if communication between the main processor and the third memory across the communication bus system is established, the power-pack is further caused to compare the at least one counter value to at least one pre-determined threshold value and inhibit use of the adapter if the at least one counter value is equal to the at least one pre-determined threshold value. More specifically, first and second counter values may be obtained and compared to respective first and second threshold values.

In aspects, the communication bus system includes a third communication bus that establishes the communication between the main processor and the third memory.

In aspects, determining whether communication between the main processor and the third memory across the third communication bus is established includes monitoring the third communication bus at a minimum rate of 1 Hz.

In aspects, the device further includes a loading unit including a fourth memory and configured to removably attach to the adapter. The fourth memory is electrically coupled with the communication bus system via the adapter to establish electrical communication between the main processor and the fourth memory upon attachment of the loading unit to the adapter with the adapter attached to the outer shell housing and the power-pack encased within the outer shell housing.

In aspects, the power-pack includes a non-transitory, computer-readable storage medium storing instructions that, when executed by the main processor, cause the power-pack to monitor the communication bus system for an indication from the adapter that the loading unit has been attached thereto, and, if an indication is received, attempt to validate the loading unit.

In aspects, attempting to validate the loading unit includes testing encryption of the loading unit and obtaining a loading unit identifier.

In aspects, the power-pack is further caused to determine whether the loading unit is a single-use loading unit or a multi-use loading unit.

Another handheld electromechanical surgical device provided in accordance with the present disclosure includes a power-pack including a power-pack memory, at least one drive component, a battery having a first memory, a main processor, and first, second, and third communication buses coupled to the main processor. The first communication bus establishes communication between the main processor and the first memory. The device further includes an outer shell housing including a second memory. The outer shell housing is configured to removably encase the power-pack therein. The second memory is electrically coupled with the second communication bus to establish communication between the main processor and the second memory upon encasing the power-pack within the outer shell housing. The device further includes an adapter including a third memory and configured to removably attach to the outer shell housing. The third memory is electrically coupled with the third communication bus to establish communication between the main processor and the third memory upon attachment of the adapter to the outer shell housing with the power-pack encased within the outer shell housing. The device further includes a non-transitory, computer-readable storage medium storing instructions that, when executed by the main processor, cause the power-pack to obtain a battery identifier from the first memory across the first communication bus, store the battery identifier in the power-pack memory, and inhibit use of the power-pack with any other battery, obtain an outer shell housing identifier from the second memory across the second communication bus, store the outer shell housing identifier in the power-pack memory, and mark the outer shell housing as used in the second memory to inhibit reuse of the outer shell housing, and obtain an adapter identifier from the third memory across the third communication bus, determine whether the adapter identifier is valid, and obtain at least one counter value from the third memory across the third communication bus.

In aspects, the device further includes a loading unit including a fourth memory. The loading unit is configured to removably attach to the adapter, while the fourth memory is electrically coupled with the third communication bus via the adapter to establish electrical communication between the main processor and the fourth memory upon attachment of the loading unit to the adapter with the adapter attached to the outer shell housing and the power-pack encased within the outer shell housing.

In aspects, the power-pack is further caused to monitor the third communication bus for an indication from the adapter that the loading unit has been attached thereto, and if an indication is received, determine a type of the loading unit.

A method of operating a handheld electromechanical surgical device provided in accordance with aspects of the present disclosure includes encasing a power-pack within an outer shell housing including a second memory, attaching an adapter including a third memory to the outer shell housing, attempting to establish communication between a main processor of the power-pack and the first memory, attempting to establish communication between the main processor and the second memory, and attempting to establish communication between the main processor and the third memory.

In aspects, if communication is established between the main processor and the first memory, the method further includes obtaining a battery identifier from the first memory, storing the battery identifier in the power-pack memory, and inhibiting use of the power-pack with any other battery.

In aspects, the method further includes performing at least one test on the battery, e.g., a battery capacity test, a battery temperature test, or a battery end-of-life test. The method may further include inhibiting use of the battery if the at least one battery test fails.

In aspects, if communication is established between the main processor and the second memory, the method further includes determining whether the outer shell housing has been used. If it is determined that the outer shell housing has been used, the method further includes inhibiting use of the power-pack with the outer shell housing. If, on the other hand, it is determined that the outer shell housing has not been used, the method further includes obtaining an outer shell housing identifier from the second memory, storing the outer shell housing identifier in the power-pack memory, and marking the outer shell housing as used in the second memory to inhibit reuse of the outer shell housing.

In aspects, if communication is established between the main processor and the third memory, the method further includes obtaining an adapter identifier from the third memory, determining whether the adapter identifier is valid, and obtaining at least one counter value from the third memory.

In aspects, the method further includes comparing the at least one counter value to at least one pre-determined threshold value, and inhibiting use of the adapter if the at least one counter value is equal to the at least one pre-determined threshold value. More specifically, first and second counter values may be obtained and compared to respective first and second threshold values.

In aspects, the method further includes determining whether a loading unit is attached to the adapter, and, if a loading unit is attached, attempting to establish communication between the main processor and the loading unit across the adapter.

In aspects, if communication between the main processor and the loading unit is established, the method further includes testing encryption of the loading unit and obtaining a loading unit identifier.

In aspects, the method further includes determining whether the loading unit is a single-use loading unit or a multi-use loading unit. If it is determined that the loading unit is a single-use loading unit, the method further includes determining whether the loading unit has been used. If, on the other hand, it is determined that the loading unit is a multi-use loading unit, the method further includes determining if the loading unit has any remaining uses. The method may additionally or alternatively include determining a type of the loading unit.

Another handheld electromechanical surgical device provided in accordance with aspects of the present disclosure includes a non-sterile power-pack, a sterile outer shell housing, an adapter, a loading unit, and a non-transitory, computer-readable storage medium storing instructions. The power-pack includes a main processor, at least one drive component, and a battery. The outer shell housing is configured to removably encase the power-pack to define a sterile barrier between the power-pack and an exterior of the outer shell housing, thus enabling use thereof in a surgical environment without breaking sterility. The adapter is selectively connectable to the outer shell housing. The loading unit is connected with the adapter. The instructions, when executed by the main processor, cause the power-pack to determine whether to permit entry into a firing mode based upon whether the outer shell housing is acceptable for firing, the adapter is acceptable for firing, the loading unit is acceptable for firing, and the battery is acceptable for firing.

In aspects, determining whether the outer shell housing is acceptable for firing includes determining whether the outer shell housing has been properly installed, detected, validated, and has not been previously used.

In aspects, determining whether the adapter is acceptable for firing includes determining whether the adapter has been properly installed, detected, validated, and calibrated successfully.

In aspects, determining whether the adapter is validated includes obtaining an identifier of the adapter, determining whether the adapter is a supported adapter, and determining whether a counter value associated with the adapter is below a pre-determined threshold value.

In aspects, determining whether the loading unit is acceptable for firing includes determining whether the loading unit is capable of providing information. If it is determined that the loading unit is capable of providing information, determining whether the loading unit is acceptable for firing further includes determining whether the loading unit has been properly installed, validated, passed encryption, can be marked as used, and has not been previously fired.

In aspects, determining whether the battery is acceptable for firing includes determining whether the battery has sufficient capacity for firing.

In aspects, the power-pack further includes a safety switch. Entry into the firing mode is inhibited prior to actuation of the safety switch.

In aspects, the power-pack includes a first communication bus and the battery includes a first memory. The main processor communicates with the first memory across the first communication bus to determine whether the battery is acceptable for firing. The first communication bus may be a 1-wire communication bus.

In aspects, the power-pack includes a second communication bus, the outer shell housing includes a second memory, and the main processor communicates with the second memory across the second communication bus to determine whether the outer shell housing is acceptable for firing. The second communication bus may be a 1-wire communication bus.

In aspects, the power-pack includes a third communication bus, the adapter includes a third memory, and the main processor communicates with the third memory across the third communication bus to determine whether the adapter is acceptable for firing. The third communication bus may be a 1-wire communication bus.

In aspects, the loading unit includes a fourth memory and the main processor communicates with the fourth memory across the third communication bus via the adapter to determine whether the loading unit is acceptable for firing.

Another handheld electromechanical surgical device provided in accordance with aspects of the present disclosure includes a non-sterile power-pack, a sterile outer housing, an adapter, a loading unit, and a non-transitory, computer-readable storage medium storing instructions. The power-pack includes a main processor, a memory, a display, a communications system, at least one drive component, and a battery. The outer shell housing is configured to removably encase the power-pack to define a sterile barrier between the power-pack and an exterior of the outer shell housing, thus enabling use thereof in a surgical environment without breaking sterility. The adapter is selectively connectable to the outer shell housing and the loading unit connected with the adapter. The instructions, when executed by the main processor, cause the power-pack to verify operation of the memory, display, communications system, at least one drive component, and battery, and, if verification is achieved, determine whether to permit entry into a firing mode. Such a determination is based upon whether the outer shell housing is acceptable for firing, the adapter is acceptable for firing, and the loading unit is acceptable for firing.

In aspects, determining whether the outer shell housing is acceptable for firing includes determining whether the outer shell housing has been properly installed, detected, validated, and has not been previously used.

In aspects, determining whether the adapter is acceptable for firing includes determining whether the adapter has been properly installed, detected, validated, and calibrated successfully.

In aspects, determining whether the loading unit is acceptable for firing includes determining whether the loading unit has been properly installed, validated, passed encryption, can be marked as used, and has not been previously fired.

In aspects, if at least one of the operation of the memory, display, communications system, at least one drive component, or battery cannot be verified, the power-pack is caused to emit a fault tone and display an error screen.

Another method of operating a handheld electromechanical surgical device provided in accordance with aspects of the present disclosure includes encasing a non-sterile power-pack within a sterile outer shell housing to establish a sterile barrier between the power-pack and an exterior of the outer shell housing to enable use thereof in a surgical environment without breaking sterility, connecting an adapter having a loading unit connected thereto to the outer shell housing, and determining, using a processor of the power-pack, whether to permit entry of the power-pack into a firing mode by determining whether the outer shell housing is acceptable for firing, the adapter is acceptable for firing, the loading unit is acceptable for firing, and the battery is acceptable for firing.

In aspects, determining whether the outer shell housing is acceptable for firing includes determining whether the outer shell housing has been properly installed, detected, validated, and has not been previously used.

In aspects, determining whether the adapter is acceptable for firing includes determining whether the adapter has been properly installed, detected, and validated.

In aspects, determining whether the adapter is acceptable for firing further includes attempting to calibrate the adapter and determining whether the adapter has been calibrated successfully.

In aspects, determining whether the loading unit is acceptable for firing includes determining whether the loading unit has been properly installed, validated, passed encryption, can be marked as used, and has not been previously fired.

In aspects, determining whether the battery is acceptable for firing includes determining whether the battery has sufficient capacity for firing, determining whether a battery temperature is within a pre-determined range, and determining whether the battery has reached its end-of-life.

In aspects, determining whether to permit entry of the power-pack into the firing mode further includes determining whether the power-pack is acceptable for firing.

In aspects, determining whether the power-pack is acceptable for firing includes determining whether the power-pack has reached its usage limit.

In aspects, determining whether the power-pack is acceptable for firing further includes verifying various operational components of the power-pack, e.g., a memory, display, communications system, or at least one drive component.

Another method of operating a handheld electromechanical surgical device provided in accordance with aspects of the present disclosure includes encasing a non-sterile power-pack within a sterile outer shell housing to establish a sterile barrier between the power-pack and an exterior of the outer shell housing thus enabling enable use thereof in a surgical environment without breaking sterility, connecting an adapter including a loading unit to the outer shell housing, determining, using a processor of the power-pack, whether to permit entry of the power-pack into a firing mode by determining whether the outer shell housing has been properly installed, detected, validated, and has not been previously used, determining whether the adapter has been properly installed, detected, and validated, determining whether the loading unit has been properly installed, validated, passed encryption, can be marked as used, and has not been previously fired, and determining whether the battery is acceptable for firing.

In aspects, determining whether the battery is acceptable for firing includes determining whether the battery has sufficient capacity for firing, determining whether a battery temperature is within a pre-determined range, and determining whether the battery has reached its end-of-life.

In aspects, if it is determined that the adapter has not been properly installed, detected, or validated, the method further includes permitting operation except for entry into the firing mode.

In aspects, if it is determined that the loading unit has not been properly installed, validated, passed encryption, cannot be marked as used, or has been previously fired, the method further includes permitting operation except for entry into the firing mode.

In aspects, if it is determined that the outer shell housing has not been properly installed, detected, validated, or has been previously used, the method further includes permitting operation except for entry into the firing mode.

In aspects, determining whether to permit entry of the power-pack into the firing mode further includes determining whether the power-pack is acceptable for firing.

In aspects, determining whether the power-pack is acceptable for firing includes determining whether the power-pack has reached its usage limit.

In aspects, determining whether the power-pack is acceptable for firing further includes verifying various operational components of the power-pack, e.g., a memory, display, communications system, or at least one drive component.

Another handheld electromechanical surgical device provided in accordance with aspects of the present disclosure includes a power-pack, an outer shell housing, and a non-transitory, computer-readable storage medium storing instructions. The power-pack includes a main processor, at least one drive component, and a battery and has a plurality of different modes including a sleep mode, a standby mode, and an active mode. The outer shell housing is configured to removably encase the power-pack. The instructions, when executed by the main processor, cause the power-pack to determine whether the outer shell housing is encased about the power-pack. If so encased, the power-pack is caused to enter the active mode upon use and enter the standby mode upon expiration of a first pre-determined period of non-use. If not encased, the power-pack is caused to enter the active mode upon use, enter the standby mode upon expiration of a second pre-determined period of non-use, and enter the sleep mode when the power-pack has remained in the standby mode for a third pre-determined period.

In aspects, the power-pack is inhibited from entering the sleep mode with the outer shell housing encased about the power-pack.

In aspects, the power-pack exits the standby and sleep modes upon use.

In aspects, with the outer shell housing initially not encased about the power-pack, the standby mode and the sleep mode are exited upon encasing the outer shell housing about the power-pack.

In aspects, the power-pack further includes a ship mode that is permanently exited upon a first initialization. Initialization may be activated in response to connecting the power-pack to a charger.

In aspects, usage includes connecting the power-pack to a charger, pressing a button on the power-pack, or manipulating the power-pack. An accelerometer of the power-pack may be configured to determine manipulation of the power-pack.

In aspects, in the active mode with the outer shell housing encased about the power-pack, actuating at least one button of the power-pack effects at least one operation, e.g., rotation, articulation, open/close, or fire.

In aspects, in the active mode with the outer shell housing not encased about the power-pack, the at least one operation is inhibited regardless of whether at least one button of the power-pack is actuated.

In aspects, in the active mode with the outer shell housing not encased about the power-pack, actuating at least one button of the power-pack displays a statistics screen on a display of the power-pack.

In aspects, the device further includes an adapter configured to removably attach to the outer shell housing. The power-pack is inhibited from exiting the active mode with the adapter attached to the outer shell housing and the outer shell housing encased about the power-pack.

In aspects, a loading unit is configured to removably attach to the adapter. Further, a plurality of different loading units may be provided, each configured to removably attach to the adapter.

In aspects, initialization is performed upon exiting the sleep mode. Such initialization may include performing a plurality of tests on the power-pack, e.g., verifying communication capability, verifying memory integrity, verifying clock functionality, testing the at least one drive component, or testing the battery. Further, testing the battery may include testing a capacity of the battery, testing a temperature of the battery, and performing an end-of-life test on the battery. The power-pack may be configured to emit a tone in response to a failed test.

Another method of operating handheld electromechanical surgical device provided in accordance with the present disclosure includes determining whether an outer shell housing is encased about a power-pack of a handheld electromechanical surgical device. If so encased, the method includes entering the active mode upon use, and entering the standby mode upon expiration of a first pre-determined period of non-use. If not encased, the method includes entering the active mode upon use, entering the standby mode upon expiration of a second pre-determined period of non-use, and entering the sleep mode when the power-pack has remained in the standby mode for a third pre-determined period.

In aspects, the method further includes inhibiting entry of the power-pack into the sleep mode with the outer shell housing encased about the power-pack.

In aspects, the method further includes exiting the standby mode upon use.

In aspects, the method further includes exiting the sleep mode upon use.

In aspects, the method further includes exiting the standby mode or the sleep mode when the outer shell housing is encased about the power-pack.

In aspects, the power-pack is initially disposed in a ship mode. In such aspects, the method further includes permanently exiting the ship mode upon a first initialization of the power-pack. Initialization may be activated in response to connecting the power-pack to a charger.

In aspects, usage includes connecting the power-pack to a charger, pressing a button on the power-pack, or manipulating the power-pack. An accelerometer of the power-pack may be configured to determine manipulation of the power-pack.

In aspects, the method further includes actuating at least one button of the power-pack to effect at least one operation with the power-pack in the active mode and the outer shell housing encased about the power-pack. The at least one operation may include at least one of rotation, articulation, open/close, or fire.

In aspects, the method further includes inhibiting the at least one operation when the power-pack is in the active mode with the outer shell housing not encased about the power-pack.

In aspects, the method further includes displaying a statistics screen on a display of the power-pack upon actuating at least one button of the power-pack with the power-pack in the active mode and the outer shell housing not encased about the power-pack.

In aspects, the method further includes attaching an adapter to the outer shell housing with the outer shell housing encased about the power-pack.

In aspects, the method further includes inhibiting the power-pack from exiting the active mode with the adapter attached to the outer shell housing.

In aspects, the method further includes attaching a loading unit to the adapter.

In aspects, the method further includes performing initialization upon exiting the sleep mode. Initialization may include performing a plurality of tests on the power-pack, e.g., verifying communication capability, verifying memory integrity, verifying clock functionality, testing the at least one drive component, or testing the battery. A tone may be emitted in response to a failed test.

Another handheld electromechanical surgical device provided in accordance with aspects of the present disclosure includes a power-pack, an outer shell housing, and an adapter. The power-pack includes at least one drive component, a battery, a main processor, and a non-transitory, computer-readable storage medium including a validation module, a calibration module, and an operation module. Each module stores instructions configured for execution by the main processor. The outer shell housing encases the power-pack therein and the adapter is configured to removably attach to the outer shell housing. Upon attachment of the adapter to the outer shell housing, the main processor executes the instructions of the validation module to determine whether the adapter has a valid identifier, is supported, has at least one use remaining, and is up-to-date and, if the adapter has a valid identifier, is supported, has at least one use remaining, and is up-to-date, executes the instructions of the calibration module to calibrate the adapter.

In aspects, determining whether the adapter is up-to-date includes determining whether software stored in the adapter is compatible.

In aspects, the main processor executes the instructions of the validation module to update the software stored in the adapter if the software stored in the adapter is determined to be incompatible.

In aspects, the device further includes a loading unit configured to removably attach to the adapter. Upon attachment of the loading unit with the adapter, the main processor executes the instructions of the validation module to determine whether the loading unit is compatible, and whether the loading unit has any uses remaining.

In aspects, the main processor executes the instructions of the validation module to determine whether the adapter is up-to-date only if the loading unit is not attached to the adapter.

In aspects, the main processor executes the instructions of the validation module to determine whether the adapter has a valid identifier, is supported, and has at least one use remaining regardless of whether the loading unit is attached to the adapter.

In aspects, the main processor executes the instructions of the calibration module to calibrate the adapter only if the loading unit is not attached to the adapter.

In aspects, upon attachment of the adapter to the outer shell housing, the main processor further executes the instructions of the validation module to determine a type of the adapter.

In aspects, if the adapter is determined to be of a first type, a first calibration is performed and, if the adapter is determined to be of a second type different from the first type, a second calibration, different from the first calibration, is performed.

In aspects, calibrating the adapter includes calibrating at least one of a clamping function, a firing function, or an articulation function.

In aspects, the at least one drive component of the power-pack includes a plurality of motors and the adapter includes a corresponding plurality of drive shafts. Each drive shaft is configured to couple to a corresponding motor upon attachment of the adapter to the outer shell housing.

In aspects, calibrating the adapter includes activating at least one of the motors to drive the corresponding at least one drive shaft to an end stop.

In aspects, the main processor is inhibited from executing the instructions of the operation module if calibration fails.

Another handheld electromechanical surgical device provided in accordance with aspects of the present disclosure includes a power-pack, an outer shell housing, an adapter, and a loading unit. The power-pack includes at least one drive component, a battery, a main processor, and a non-transitory, computer-readable storage medium including a validation module, a calibration module, and an operation module, each storing instructions. The outer shell housing encases the power-pack therein while the adapter is configured to removably attach to the outer shell housing. Upon attachment of the adapter to the outer shell housing, the main processor executes the instructions of the validation module to validate the adapter by determining whether the adapter has a valid identifier, is supported, has at least one use remaining, and is up-to-date. If the adapter is validated, the instructions of the calibration module are executed to calibrate the adapter. The loading unit is attached to the adapter. Upon attachment of the loading unit with the adapter, the main processor executes the instructions of the validation module to validate the loading unit by determining whether the loading unit is compatible and whether the loading unit has any uses remaining. If the adapter is validated, calibration is successful, and the loading unit is validated, the main processor is permitted to execute the instructions of the operation module to perform at least one of an articulation function, a clamping function, or a firing function.

In aspects, if the adapter is not validated, not calibrated successfully, or the loading unit is not validated, the main processor is inhibited from executing the instructions of the operation module.

In aspects, upon attachment of the adapter to the outer shell housing, the main processor further executes the instructions of the validation module to determine a type of the adapter. In such aspects, if the adapter is determined to be of a first type, a first calibration is performed and, if the adapter is determined to be of a second type different from the first type, a second calibration, different from the first calibration, is performed.

In aspects, the main processor executes the instructions of the validation module to determine whether the adapter is up-to-date only if the loading unit is not attached to the adapter.

In aspects, the main processor executes the instructions of the validation module to determine whether the adapter has a valid identifier, is supported, and has at least one use remaining regardless of whether the loading unit is attached to the adapter.

In aspects, the main processor executes the instructions of the calibration module to calibrate the adapter only if the loading unit is not attached to the adapter.

Another method of operating a handheld electromechanical surgical device provided in accordance with the present disclosure includes attaching an adapter to an outer shell housing encasing a power-pack, validating the adapter by determining whether the adapter has a valid identifier, is supported, has at least one use remaining, and is up-to-date, and, if the adapter is validated, calibrating the adapter.

In aspects, determining whether the adapter is up-to-date includes determining whether software stored in the adapter is compatible.

In aspects, the method further includes updating the software stored in the adapter if the software stored in the adapter is determined to be incompatible.

In aspects, the method further includes attaching a loading unit to the adapter and validating the loading unit by determining whether the loading unit is compatible and whether the loading unit has any uses remaining.

In aspects, determining whether the adapter is up-to-date is only performed if the loading unit is not attached to the adapter.

In aspects, determining whether the adapter has a valid identifier, is supported, and has at least one use remaining is performed regardless of whether the loading unit is attached to the adapter.

In aspects, calibrating the adapter is performed only if the loading unit is not attached to the adapter.

In aspects, the method further includes determining a type of the adapter. If the adapter is determined to be of a first type, the method includes performing a first calibration. If the adapter is determined to be of a second type different from the first type, the method further includes performing a second calibration, different from the first calibration.

In aspects, calibrating the adapter includes calibrating at least one of a clamping function, a firing function, or an articulation function.

In aspects, the method further includes inhibiting operation if validation of the adapter or calibration of the adapter fails.

Another method of operating a handheld electromechanical surgical device provided in accordance with the present disclosure includes attaching an adapter to an outer shell housing encasing a power-pack, validating the adapter by determining whether the adapter has a valid identifier, is supported, has at least one use remaining, and is up-to-date, if the adapter is validated, calibrating the adapter, attaching a loading unit to the adapter, validating the loading unit by determining whether the loading unit is compatible and whether the loading unit has any uses remaining, and, if adapter is validated, calibration is successful, and the loading unit is validated, permitting at least one of an articulation function, a clamping function, or a firing function.

In aspects, if the adapter is not validated, not calibrated successfully, or the loading unit is not validated, the method further includes inhibiting operation.

In aspects, validating the adapter further includes determining a type of the adapter.

In aspects, if the adapter is determined to be of a first type, calibrating the adapter includes performing a first calibration and, if the adapter is determined to be of a second type different from the first type, calibrating the adapter includes performing a second calibration, different from the first calibration.

In aspects, determining whether the adapter is up-to-date includes determining whether software stored in the adapter is compatible.

In aspects, the method further includes updating software stored in the adapter if the software stored in the adapter is determined to be incompatible.

Another handheld electromechanical surgical device provided in accordance with aspects of the present disclosure includes a handle and shaft assembly, a loading unit configured to removably attach to the handle and shaft assembly, a processor, and a non-transitory, computer-readable storage medium storing instructions that, when executed by the processor, cause the handle and shaft assembly to determine whether the loading unit is capable of providing information. If the loading unit is determined not to be capable of providing information, the handle and shaft assembly is further caused to determine whether the loading unit is properly installed and, if the loading unit is properly installed, permit operation using the loading unit. If the loading unit is determined to be capable of providing information, the handle and shaft assembly is further caused to communicate with the loading unit to determine whether the loading unit is acceptable for firing and, if the loading unit is acceptable for firing, permit operation using the loading unit.

In aspects, if the loading unit is determined to be capable of providing information, determining whether the loading unit is acceptable for firing includes determining whether the loading unit is valid, passes encryption, can be marked as used, and has at least one firing remaining.

In aspects, if the loading unit is determined to be capable of providing information, determining whether the loading unit is acceptable for firing further includes determining a type of the loading unit.

In aspects, determining the type of the loading unit includes determining whether the loading unit is a single-use loading unit or a multi-use loading unit.

In aspects, if the loading unit is determined not to be capable of providing information, determining whether the loading unit is properly installed includes outputting a display notifying a user to check that the loading unit is properly installed.

In aspects, if the loading unit is determined not to be capable of providing information and the loading unit is not properly installed, the handle and shaft assembly is caused to inhibit operation using the loading unit.

In aspects, if the loading unit is determined to be capable of providing information and the loading unit is not acceptable for firing, the handle and shaft assembly is caused to inhibit at least some operation using the loading unit.

In aspects, the handle and shaft assembly is configured to open/close the loading unit, articulate the loading unit, and fire the loading unit. If the loading unit is not acceptable for firing, the handle and shaft assembly is caused to permit opening/closing of the loading unit and articulation of the loading unit but inhibit firing of the loading unit.

In aspects, the handle and shaft assembly includes a power-pack, an outer shell housing encasing the power-pack therein, and an adapter configured to removably attach to the outer shell housing. The loading unit is configured to removably attach to the adapter.

In aspects, the outer shell housing is configured to removably encase the power-pack therein.

In aspects, the power-pack includes at least one drive component, a battery, the processor, and the non-transitory, computer-readable storage medium.

Another handheld electromechanical surgical device provided in accordance with aspects of the present disclosure includes a handle and shaft assembly, a loading unit configured to removably attach to the handle and shaft assembly, a processor, and a non-transitory, computer-readable storage medium storing instructions that, when executed by the processor, cause the handle and shaft assembly to determine whether the loading unit passes encryption, determine whether the loading unit has a valid identifier, and, if the loading unit passes encryption and has a valid identifier, determine whether the loading unit is a single-use loading unit or a multi-use loading unit. If the loading unit is a single-use loading unit, the handle and shaft assembly is further caused to determine whether the single-use loading unit has been used and determine whether the single-use loading unit can be marked as used. If the single-use loading unit has not been used and can be marked as used, the handle and shaft assembly is further caused to permit operation using the single-use loading unit. If the loading unit is determined to be a multi-use loading unit, the handle and shaft assembly is further caused to determine whether the multi-use loading unit has at least one use remaining and determine whether an unused cartridge is engaged with the multi-use loading unit. If the multi-use loading unit has at least one use remaining and an unused cartridge is engaged with the multi-use loading unit, the handle and shaft assembly is further caused to permit operation using the multi-use loading unit.

In aspects, the handle and shaft assembly is configured to open/close the loading unit, articulate the loading unit, and fire the loading unit. If the loading unit does not pass encryption or does not have a valid identifier, the handle and shaft assembly is caused to permit opening/closing of the loading unit and articulation of the loading unit but inhibit firing of the loading unit.

In aspects, the handle and shaft assembly is configured to open/close the loading unit, articulate the loading unit, and fire the loading unit. If the single-use loading unit has been used or the multi-use loading unit does not have at least one use remaining, the handle and shaft assembly is caused to permit opening/closing of the loading unit and articulation of the loading unit but inhibit firing of the loading unit.

In aspects, the handle and shaft assembly includes a power-pack, an outer shell housing encasing the power-pack therein, and an adapter configured to removably attach to the outer shell housing. The loading unit may be configured to removably attach to the adapter in such aspects.

In aspects, the outer shell housing is configured to removably encase the power-pack therein.

In aspects, the power-pack includes at least one drive component, a battery, the processor, and the non-transitory, computer-readable storage medium.

Another method of operating a handheld electromechanical surgical device provided in accordance with aspects of the present disclosure includes connecting a loading unit to a handle and shaft assembly and determining whether the loading unit is capable of providing information. If the loading unit is determined not to be capable of providing information, the method further includes determining whether the loading unit is properly installed. If the loading unit is properly installed, the method further includes permitting operation using the loading unit. If the loading unit is determined to be capable of providing information, the method further includes communicating with the loading unit to determine whether the loading unit is acceptable for firing. If the loading unit is acceptable for firing, the method further includes permitting operation using the loading unit.

In aspects, if the loading unit is determined to be capable of providing information, determining whether the loading unit is acceptable for firing includes determining whether the loading unit is valid, passes encryption, can be marked as used, and has at least one firing remaining.

In aspects, if the loading unit is determined to be capable of providing information, determining whether the loading unit is acceptable for firing further includes determining a type of the loading unit.

In aspects, determining the type of the loading unit includes determining whether the loading unit is a single-use loading unit or a multi-use loading unit.

In aspects, if the loading unit is determined not to be capable of providing information, determining whether the loading unit is properly installed includes outputting a display notifying a user to check that the loading unit is properly installed.

In aspects, if the loading unit is determined not to be capable of providing information and the loading unit is not properly installed, the method further includes inhibiting operation using the loading unit.

In aspects, if the loading unit is determined to be capable of providing information and the loading unit is not acceptable for firing, the method further includes inhibiting at least some operation using the loading unit.

Another method of operating a handheld electromechanical surgical device provided in accordance with aspects of the present disclosure includes connecting a loading unit to a handle and shaft assembly, determining whether the loading unit passes encryption, determining whether the loading unit has a valid identifier, and, if the loading unit passes encryption and has a valid identifier, determining whether the loading unit is a single-use loading unit or a multi-use loading unit. If the loading unit is a single-use loading unit, the method further includes determining whether the single-use loading unit has been used and determining whether the single-use loading unit can be marked as used. If the single-use loading unit has not been used and can be marked as used, the method further includes permitting operation using the single-use loading unit. If the loading unit is determined to be a multi-use loading unit, the method further includes determining whether the multi-use loading unit has at least one use remaining and determining whether an unused cartridge is engaged with the multi-use loading unit. If the multi-use loading unit has at least one use remaining and an unused cartridge is engaged with the multi-use loading unit, the method further includes permitting operation using the multi-use loading unit.

In aspects, the handle and shaft assembly includes a power-pack, an outer shell housing, and an adapter. In such aspects, the method further includes encasing the power-pack within the outer shell housing and attaching the adapter to the outer shell housing. Connecting the loading unit to the handle and shaft assembly includes attaching the loading unit to the adapter.

In aspects, the handle and shaft assembly is configured to open/close the loading unit, articulate the loading unit, and fire the loading unit. If the loading unit does not pass encryption or does not have a valid identifier, the method further includes permitting opening/closing of the loading unit and articulation of the loading unit and inhibiting firing of the loading unit.

In aspects, the handle and shaft assembly is configured to open/close the loading unit, articulate the loading unit, and fire the loading unit. If the single-use loading unit has been used or the multi-use loading unit does not have at least one use remaining, the method further includes permitting opening/closing of the loading unit and articulation of the loading unit and inhibiting firing of the loading unit.

Another handheld electromechanical surgical device provided in accordance with aspects of the present disclosure includes a loading unit, at least one sensor, and a power-pack. The loading unit includes an anvil assembly and a cartridge assembly, at least one of which is movable relative to the other from an open position to a closed position to clamp tissue therebetween. The cartridge assembly houses a plurality of staples therein and is configured to fire the plurality of staples through tissue clamped between the anvil assembly and the cartridge assembly for formation against the anvil assembly. The loading unit defines an operative length. The at least one sensor is configured to provide an indication of a thickness of tissue clamped between the anvil assembly and the cartridge assembly. The power-pack includes at least one drive component and a processor. The at least one drive component is operably coupled to the loading unit such that driving of the at least one drive component fires the plurality of staples. The processor is configured to receive information indicative of the operative length and the thickness of tissue and to implement a control algorithm for controlling the at least one drive component in accordance with the operative length and the tissue thickness such that an optimal firing speed and/or an optimal firing force are achieved during firing of the plurality of staples.

In aspects, the device further includes at least one sensor configured to provide an indication of a pre-compression time. In such aspects, the processor is further configured to implement the control algorithm in accordance with the pre-compression time to achieve the optimal firing speed and/or the optimal firing force.

In aspects, the power-pack further includes a memory storing at least one of experimental data or historical data for use by the processor in implementing the control algorithm.

In aspects, the at least one drive component is at least one motor.

In aspects, the loading unit includes a memory storing the information indicative of the operative length of the loading unit. In such aspects, the processor is configured to receive the information indicative of the operative length of the loading unit from the memory of the loading unit.

A method of operating a handheld electromechanical surgical device provided in accordance with aspects of the present disclosure includes determining an operative length of a loading unit that includes an anvil assembly and a cartridge assembly housing a plurality of staples, clamping tissue between the anvil assembly and the cartridge assembly, determining a thickness of tissue clamped between the anvil assembly and the cartridge assembly, determining an optimal firing algorithm based upon the operative length and the thickness of tissue, and firing the plurality of staples through tissue clamped between the anvil assembly and the cartridge assembly for formation against the anvil assembly in accordance with the optimal firing algorithm such that an optimal firing speed and/or an optimal firing force are achieved during the firing of the plurality of staples.

In aspects, determining the optimal firing algorithm includes consulting at least one of experimental data or historical data.

In aspects, the method further includes determining a pre-compression time. In such aspects, the optimal firing algorithm is determined based upon the operative length, the tissue thickness, and the pre-compressing time.

In aspects, the information indicative of the operative length of the loading unit is stored in a memory of the loading unit and is retrievable therefrom for determining the optimal firing algorithm.

BRIEF DESCRIPTION OF THE DRAWINGS

Embodiments of the present disclosure are described herein with reference to the accompanying drawings, wherein:

FIG. 20 is a front, perspective view of the adapter assembly of FIG. 1;

FIG. 21 is a rear, perspective view of the adapter assembly of FIGS. 1 and 20;

FIG. 23 is a top, plan view of the adapter assembly of FIGS. 1 and 20-22;

FIG. 24 is a side, elevational view of the adapter assembly of FIGS. 1 and 20-23;

FIGS. 61 and 62 are alternate cutaway views of the distal portion of the adapter assembly of FIGS. 1 and 20-26 engaged with the loading unit, illustrating the annular member in a first orientation and a sensor link in a non-locking configuration;

FIGS. 63 and 64 are alternate cutaway views of the distal portion of the adapter assembly of FIGS. 1 and 20-26 engaged with the loading unit, illustrating the annular member in a second orientation and the sensor link in a locking configuration;

FIG. 66 is a cutaway view of the loading unit of FIGS. 1 and 53-54 inserted into the annular member shown in FIG. 49;

FIG. 67 is a cross-sectional view of the loading unit of FIGS. 1 and 53-54, taken along line 67-67 of FIG. 66;

FIG. 68 is a cross-sectional view of the loading unit of FIGS. 1 and 53-54, taken along line 68-68 of FIG. 66;

FIGS. 69A-69D are perspective views of various other loading units configured for use with the handheld surgical device of FIG. 1;

DETAILED DESCRIPTION OF EMBODIMENTS

Figure 1:
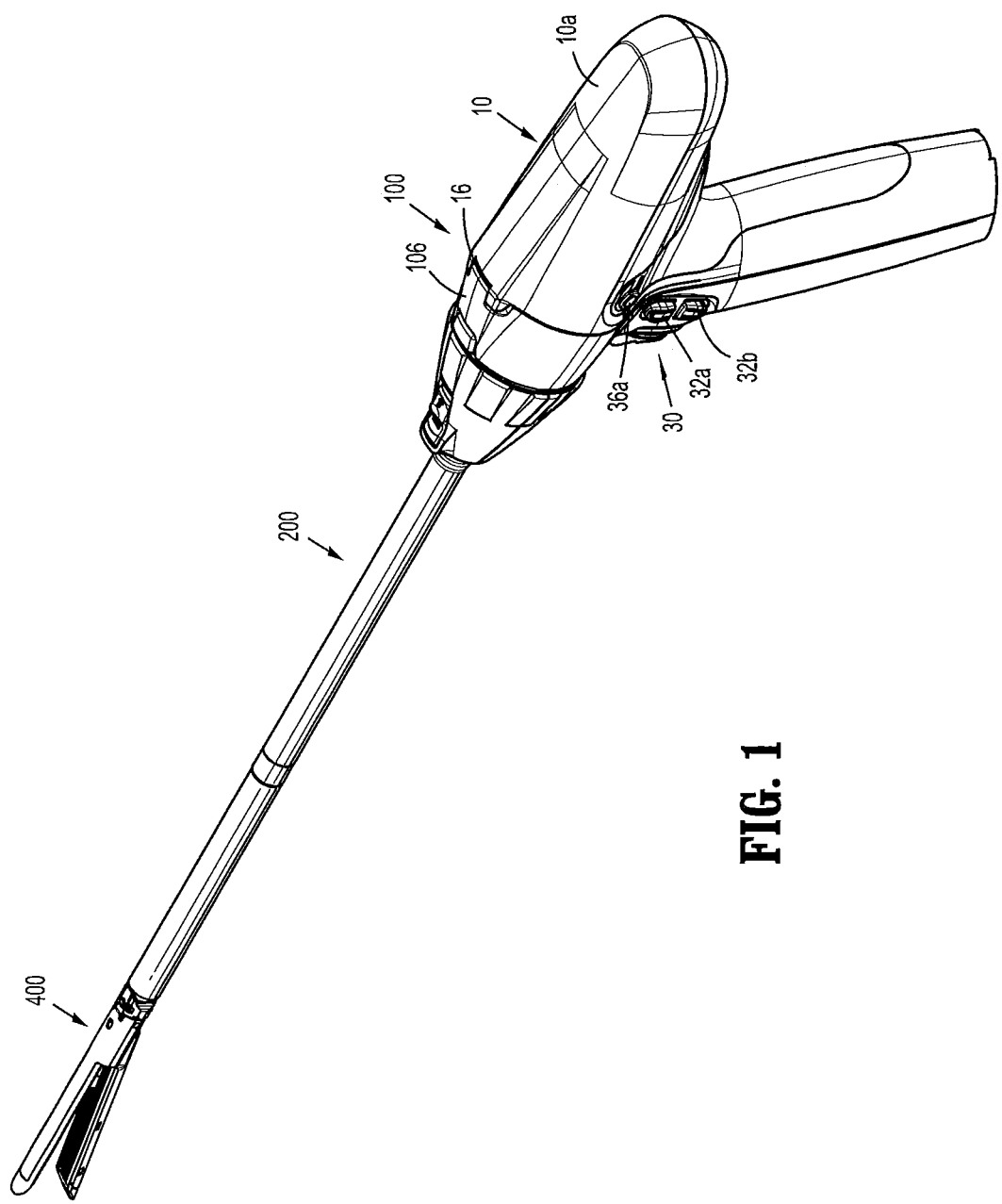
FIG. 1 is a perspective view of a handheld surgical device and adapter assembly, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument. In addition to enabling powered actuation and manipulation, surgical device 100 further incorporates various safety and control features that help ensure proper, safe, and effective use thereof.

As illustrated in FIG. 1, surgical device is configured for selective connection with an adapter 200, and, in turn, adapter 200 is configured for selective connection with end effectors or single use loading units ("SULU's") 400. Although described with respect to adapter 200 and SULU 400, different adapters configured for use with different end effectors and/or different end effectors configured for use with adapter 200 are also capable of being used with surgical device 100. Suitable end effectors configured for use with adapter 200 and/or other adapters usable with surgical device 100 include end effectors configured for performing endoscopic gastro-intestinal anastomosis (EGIA) procedures, e.g., SULU 400 and multi-use loading unit ("MULU") 900B (FIG. 69B1), end effectors configured to perform end-to-end anastomosis (EEA) procedures, e.g., loading unit 900A (FIG. 69A), a transverse stapling loading units, e.g., loading unit 900C (FIG. 69C), and curved loading units, e.g., loading unit 900D (FIG. 69D).

As illustrated in FIGS. 1-11, surgical device 100 includes a power-pack 101, and an outer shell housing 10 configured to selectively receive and sealingly encase power-pack 101 to establish a sterile barrier about power-pack 101. Outer shell housing 10 includes a distal half-section 10a and a proximal half-section 10b pivotably connected to distal half-section 10a by a hinge 16 located along an upper edge of distal half-section 10a and proximal half-section 10b. When joined, distal and proximal half-sections 10a, 10b define a shell cavity 10c therein in which power-pack 101 is selectively situated.

Distal and proximal half-sections 10a, 10b are divided along a plane that traverses a longitudinal axis "X" of adapter 200.

Each of distal and proximal half-sections 10a, 10b includes a respective upper shell portion 12a, 12b, and a respective lower shell portion 14a, 14b. Lower shell portions 12a, 12b define a snap closure feature 18 for selectively securing lower shell portions 12a, 12b to one another and for maintaining outer shell housing 10 in a closed condition.

Distal half-section 10a of outer shell housing 10 defines a connecting portion 20 configured to accept a corresponding drive coupling assembly 210 of adapter 200. Specifically, distal half-section 10a of outer shell housing 10 has a recess 20 that receives a portion of drive coupling assembly 210 of adapter 200 when adapter 200 is mated to surgical device 100.

Connecting portion 20 of distal half-section 10a defines a pair of axially extending guide rails 20a, 20b projecting radially inward from inner side surfaces thereof. Guide rails 20a, 20b assist in rotationally orienting adapter 200 relative to surgical device 100 when adapter 200 is mated to surgical device 100.

Connecting portion 20 of distal half-section 10a defines three apertures 22a, 22b, 22c formed in a distally facing surface thereof and which are arranged in a common plane or line with one another. Connecting portion 20 of distal half-section 10a also defines an elongate slot 24 (to contain connector 66, see FIG. 3) also formed in the distally facing surface thereof.

Connecting portion 20 of distal half-section 10a further defines a female connecting feature 26 (see FIG. 2) formed in a surface thereof. Female connecting feature 26 selectively engages with a male connecting feature of adapter 200, as will be described in greater detail below.

Distal half-section 10a of outer shell housing 10 supports a distal facing toggle control button 30. Toggle control button 30 is capable of being actuated in a left, right, up and down direction upon application of a corresponding force thereto or a depressive force thereto.

Distal half-section 10a of outer shell housing 10 supports a right-side pair of control buttons 32a, 32b; and a left-side pair of control button 34a, 34b. Right-side control buttons 32a, 32b and left-side control buttons 34a, 34b are capable of being actuated upon application of a corresponding force thereto or a depressive force thereto.

Proximal half-section 10b of outer shell housing 10 supports a right-side control button 36a and a left-side control button 36b. Right-side control button 36a and left-side control button 36b are capable of being actuated upon application of a corresponding force thereto or a depressive force thereto.

Distal half-section 10a and proximal half-section 10b of outer shell housing 10 are fabricated from a polycarbonate or similar polymer, and are clear or transparent or may be overmolded.

With reference to FIGS. 5-11, surgical device 100 includes an insertion guide 50 that is configured and shaped to seat on and entirely surround a distal facing edge 10d (FIGS. 3 and 9) of proximal half-section 10b. Insertion guide 50 includes a body portion 52 having a substantially U-shaped transverse cross-sectional profile, and a stand-off 54 extending from a bottom of body portion 52. Stand-off 54 is configured to engage snap closure feature 18 of each of lower shell portions 12a, 12b of respective distal and proximal half-sections 10a, 10b of outer shell housing 10.

In use, when body portion 52 of insertion guide 50 is seated on distal facing edge 10d of proximal half-section 10b, snap closure feature 18 of lower shell portion 12a of distal half-section 10a engages a first end of stand-off 54, and snap closure feature 18 of lower shell portion 12b of proximal half-section 10b engages a first end of stand-off 54.

Figure 2:
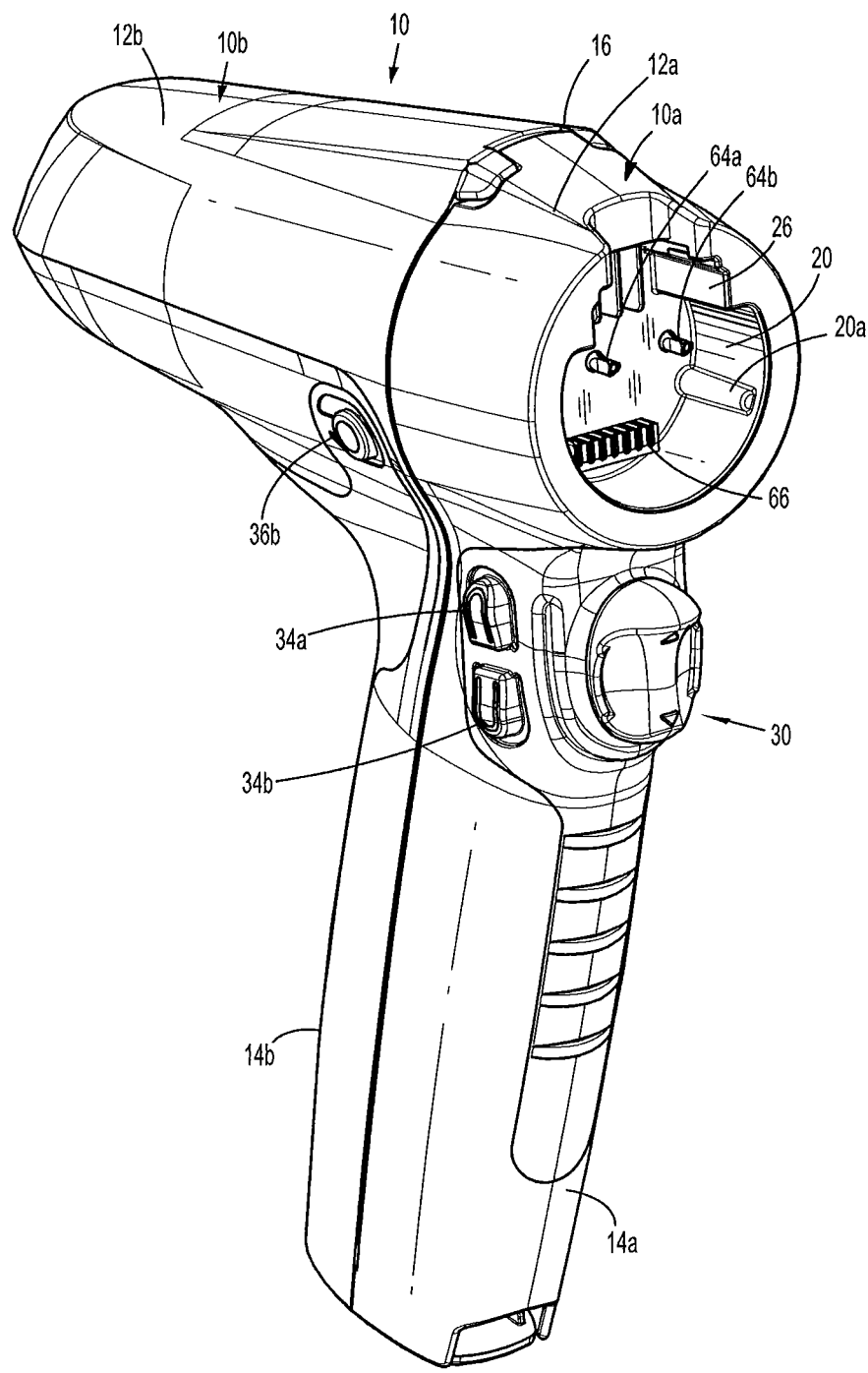
FIG. 2 is a perspective view of the handheld surgical device of FIG. 1.
Figure 3:
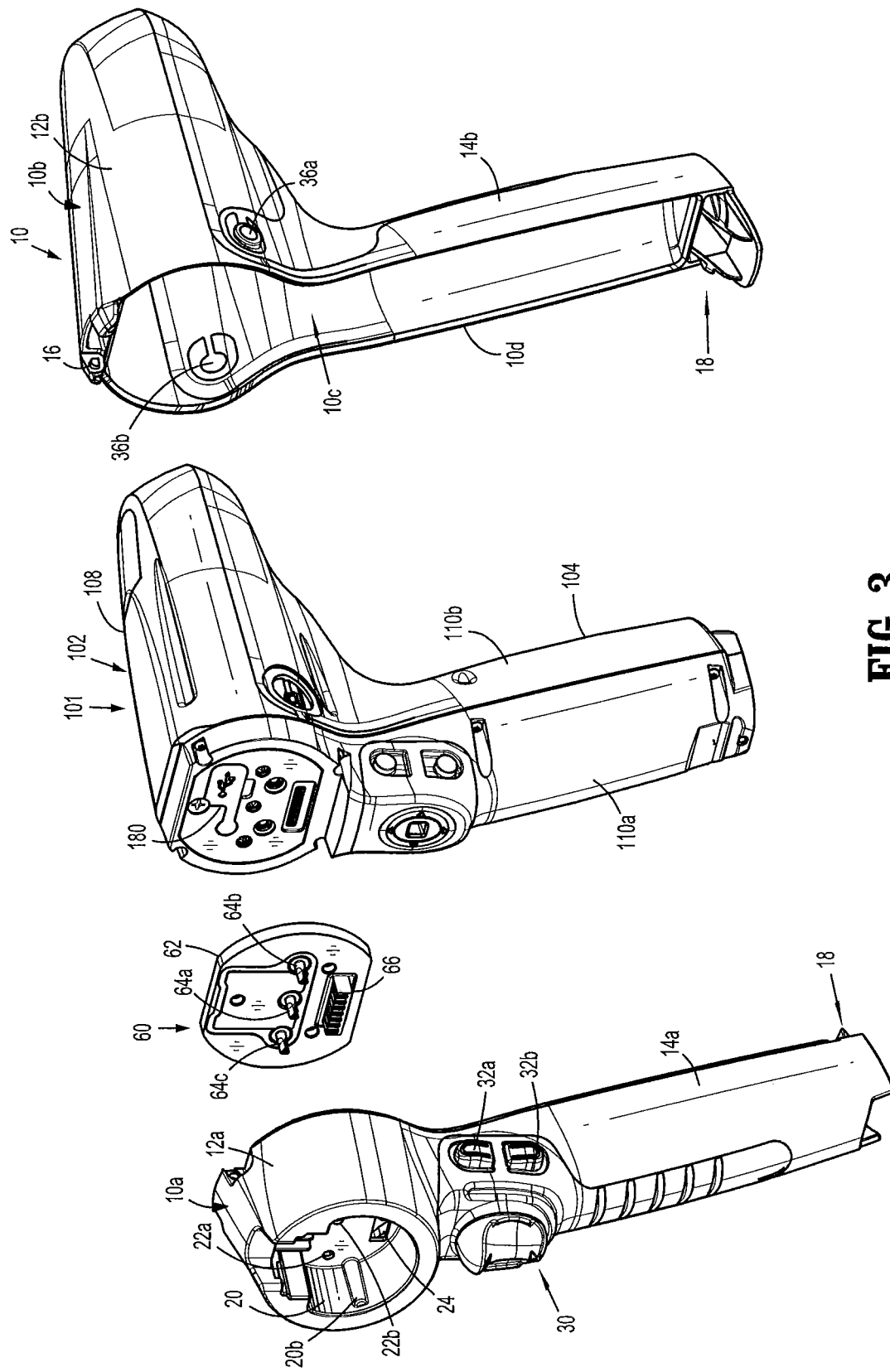
FIG. 3 is a front perspective view, with parts separated, of the handheld surgical device of FIGS. 1 and 2.
Figure 4:
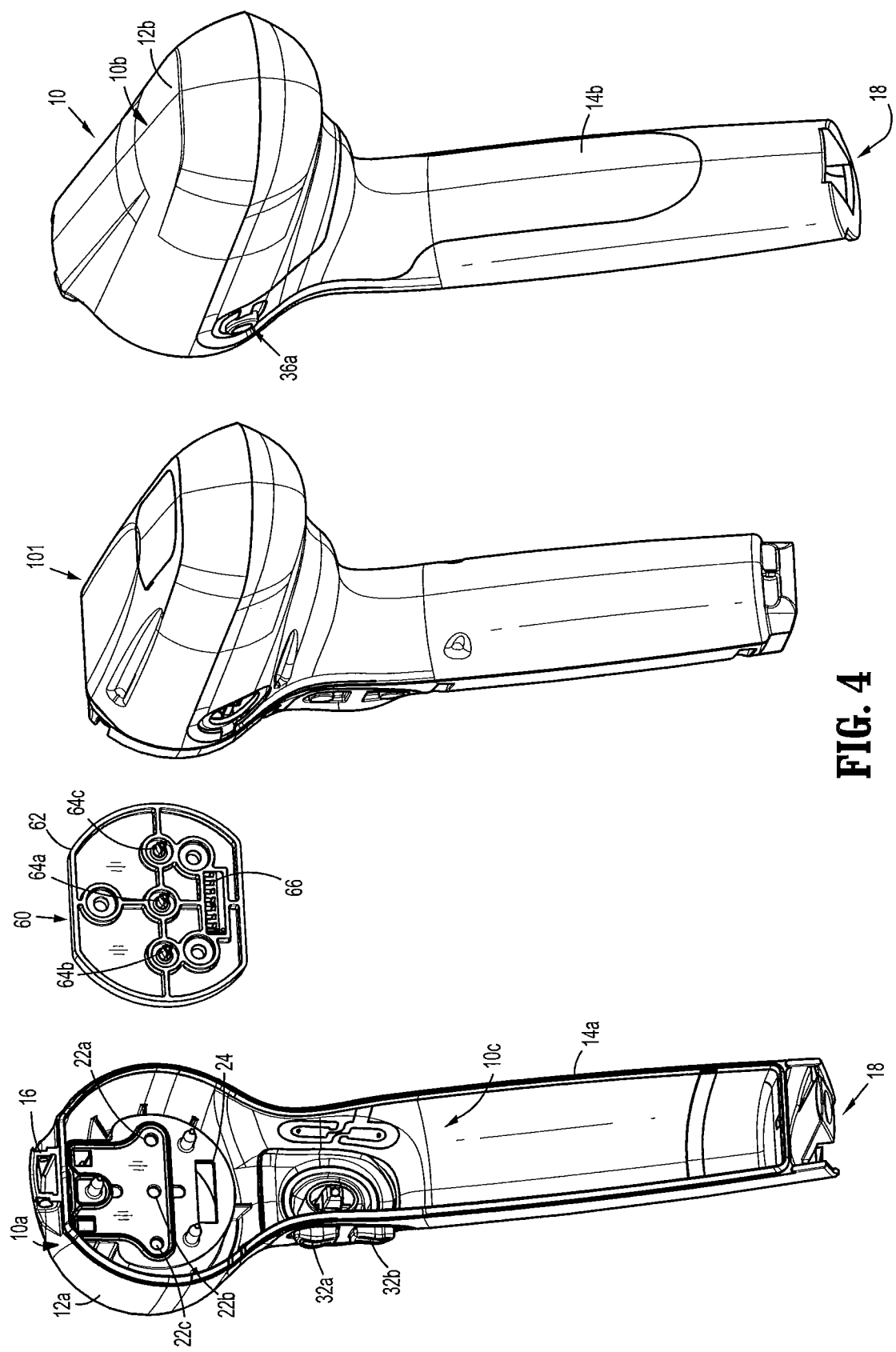
FIG. 4 is a rear perspective view, with parts separated, of the handheld surgical device of FIGS. 1 and 2.
Figure 6:
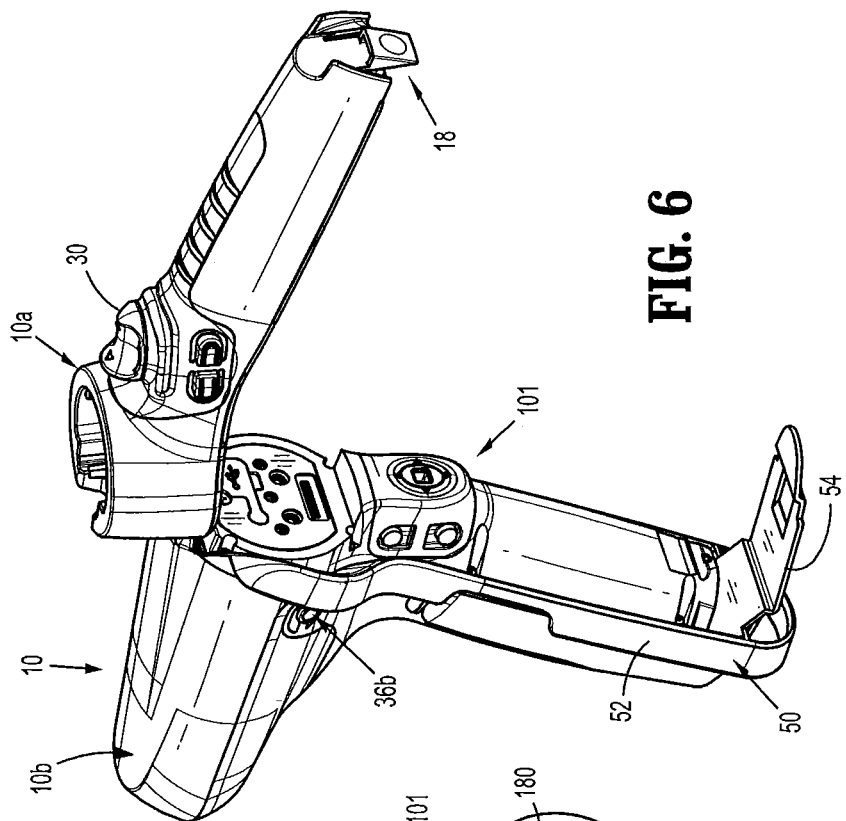
FIG. 6 is a perspective view illustrating the power-pack nested into the outer shell housing of the handheld surgical device.
Figure 5:
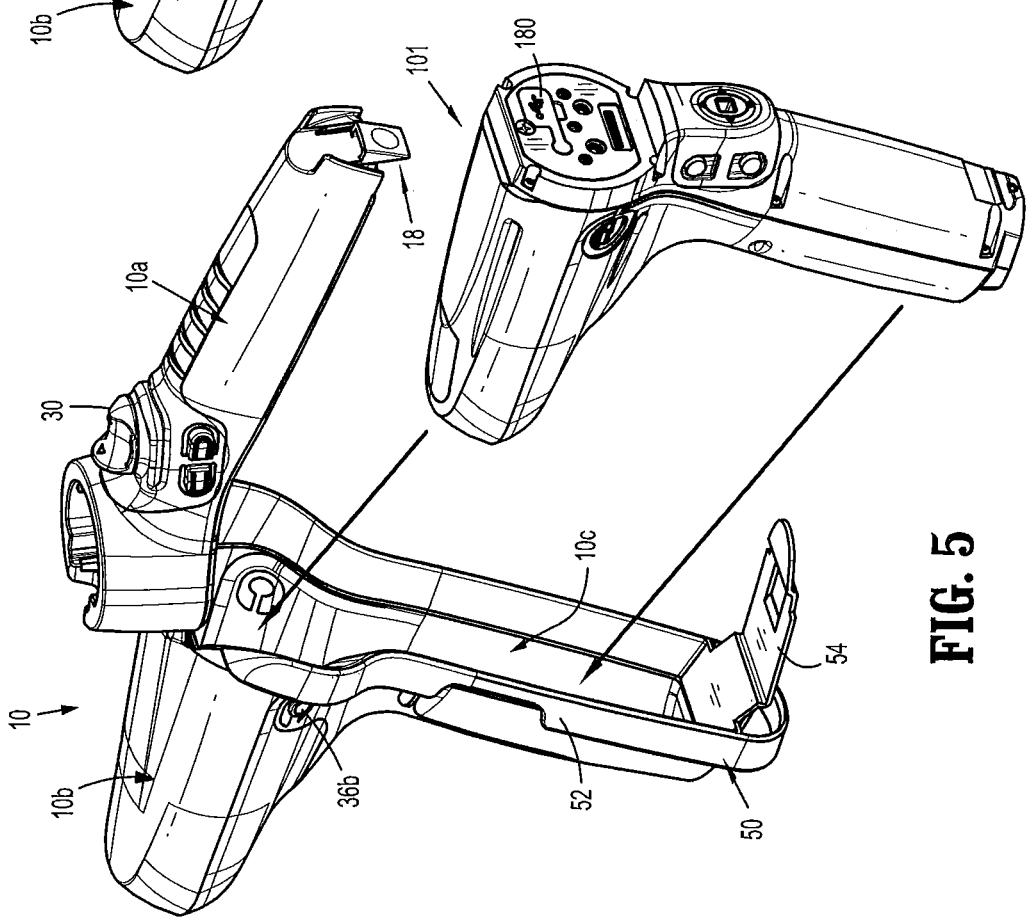
FIG. 5 is a perspective view illustrating insertion of a power-pack into an outer shell housing of the handheld surgical device.
Figure 7:
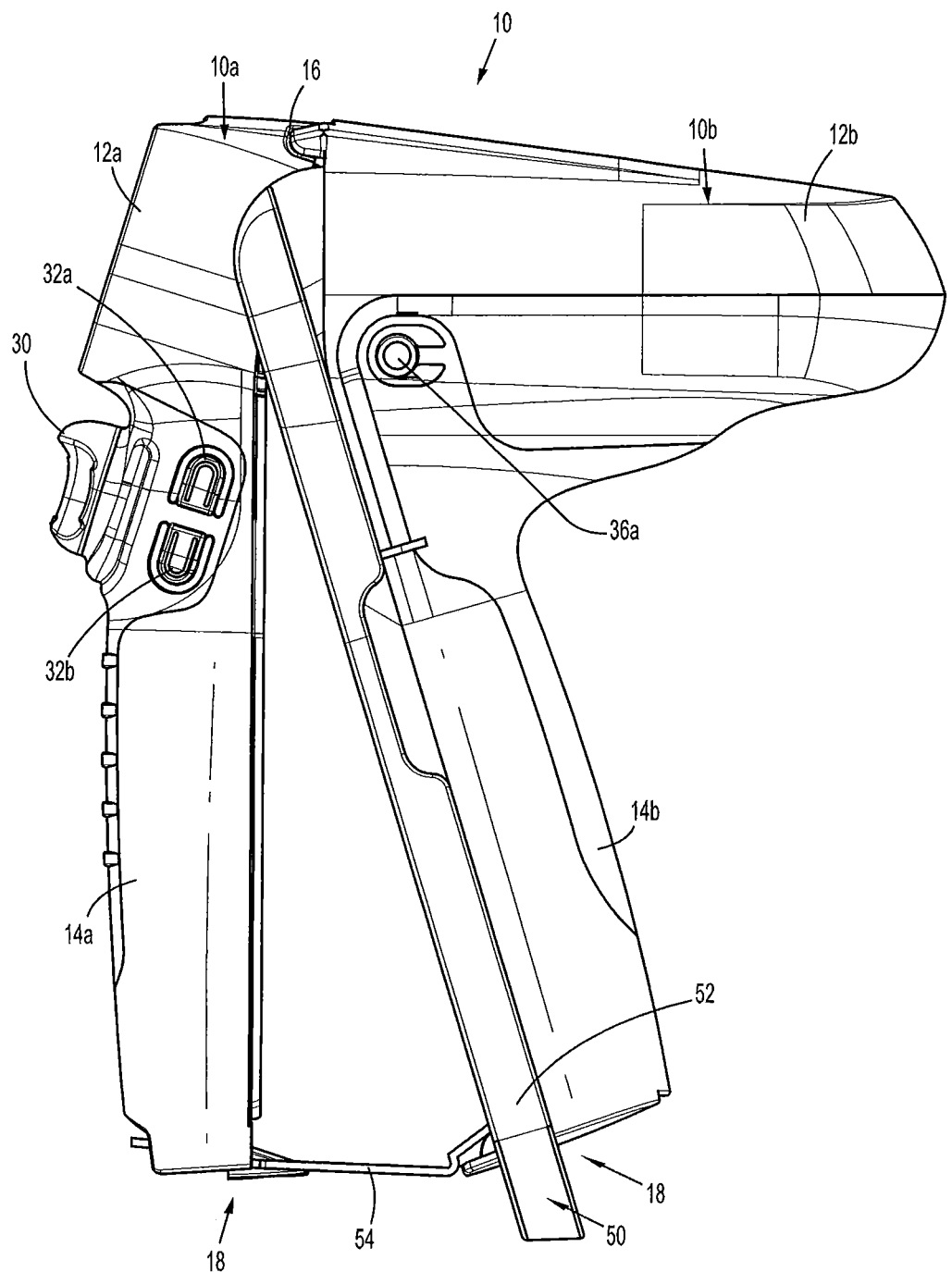
FIG. 7 is a side elevational view of the outer shell housing of the handheld surgical device.
Figure 9:
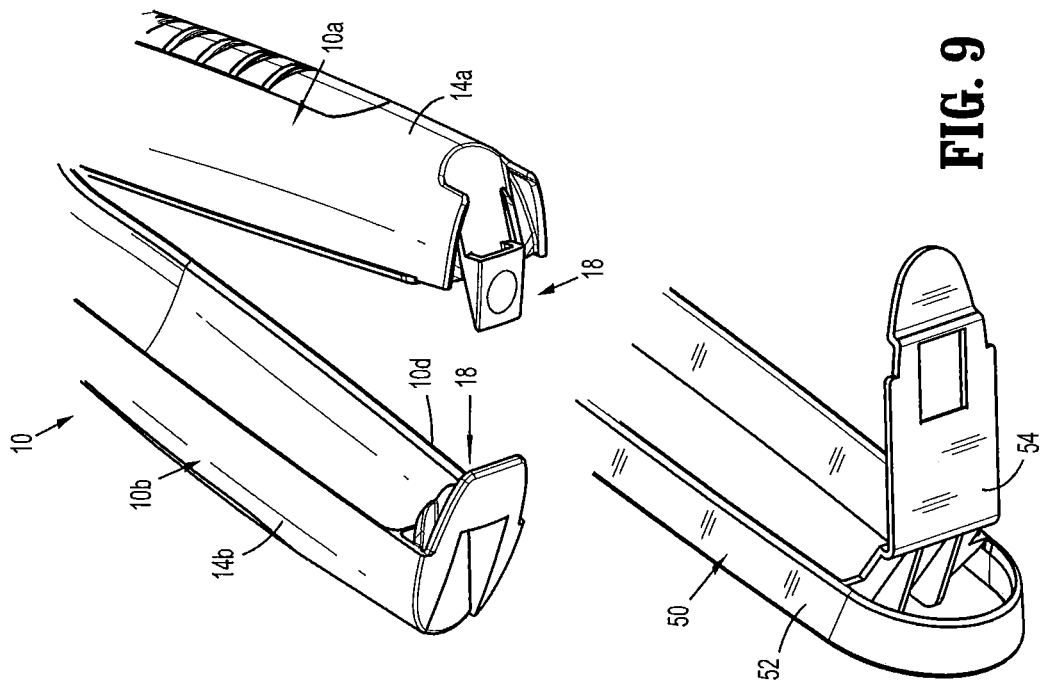
FIG. 9 is an enlarged, bottom perspective view of the outer shell housing of the handheld surgical device with the insertion guide separated therefrom.
Figure 8:
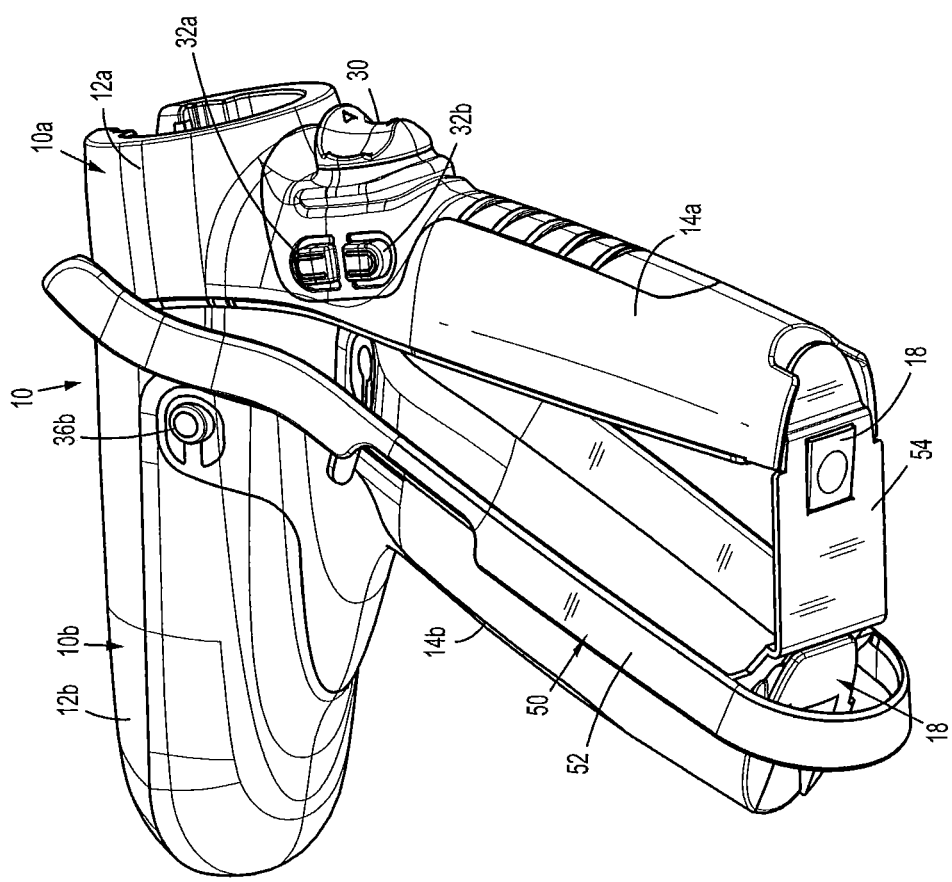
FIG. 8 is a bottom perspective view of the outer shell housing of the handheld surgical device, and an insertion guide thereof.
Figure 10:
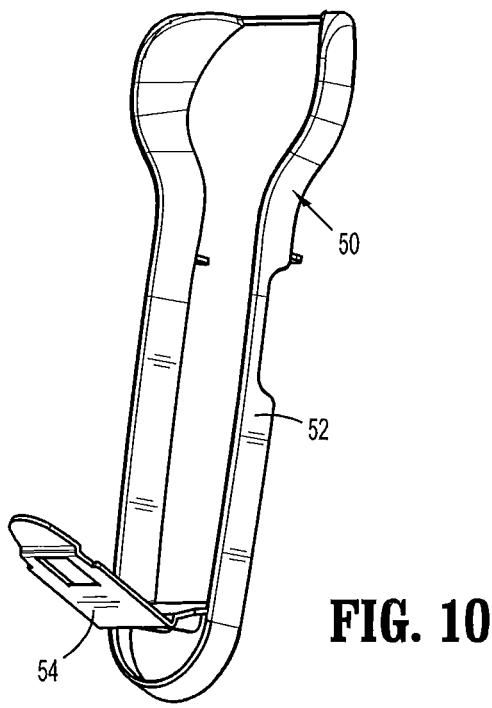
FIG. 10 is a first perspective view of the insertion guide.
Figure 11:
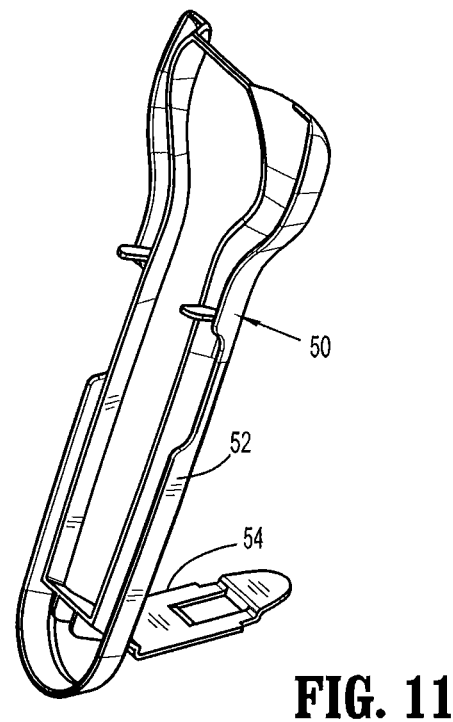
FIG. 11 is a second perspective view of the insertion guide.

With reference to FIGS. 2-4, outer shell housing 10 includes a sterile barrier plate assembly 60 selectively supported in distal half-section 10a. Specifically, sterile barrier plate assembly 60 is disposed behind connecting portion 20 of distal half-section 10a and within shell cavity 10c of outer shell housing 10. Plate assembly 60 includes a plate 62 rotatably supporting three coupling shafts 64a, 64b, 64c. Each coupling shaft 64a, 64b, 64c extends from opposed sides of plate 62 and has a tri-lobe transverse cross-sectional profile. Each coupling shaft 64a, 64b, 64c extends through a respective aperture 22a, 22b, 22c of connecting portion 20 of distal half-section 10a when sterile barrier plate assembly 60 is disposed within shell cavity 10c of outer shell housing 10.

Plate assembly 60 further includes an electrical pass-through connector 66 supported on plate 62. Pass-through connector 66 extends from opposed sides of plate 62. Each coupling shaft 64a, 64b, 64c extends through aperture 24 of connecting portion 20 of distal half-section 10a when sterile barrier plate assembly 60 is disposed within shell cavity 10c of outer shell housing 10. Pass-through connector 66 defines a plurality of contact paths each including an electrical conduit for extending an electrical connection across plate 62. The various communications relayed across pass-through connector 66 are described in detail below with respect to FIGS. 70-82.

When plate assembly 60 is disposed within shell cavity 10c of outer shell housing 10, distal ends of coupling shaft 64a, 64b, 64c and a distal end of pass-through connector 66 are disposed or situated within connecting portion 20 of distal half-section 10a of outer shell housing 10, and electrically and/or mechanically engage respective corresponding features of adapter 200, as will be described in greater detail below.

In operation, with a new and/or sterile outer shell housing 10 in an open configuration (i.e., distal half-section 10a separated from proximal half-section 10b, about hinge 16), and with insertion guide 50 in place against the distal edge of proximal half-section 10b of outer shell housing 10, power-pack 101 is inserted into shell cavity 10c of outer shell housing 10. With power-pack 101 inserted into shell cavity 10c of outer shell housing 10, insertion guide 50 is removed from proximal half-section 10b and distal half-section 10a is pivoted, about hinge 16, to a closed configuration for outer shell housing 10. In the closed configuration, snap closure feature 18 of lower shell portion 12a of distal half-section 10a engages snap closure feature 18 of lower shell portion 12b of proximal half-section 10b.

In operation, following a surgical procedure, snap closure feature 18 of lower shell portion 12a of distal half-section 10a is disengaged from snap closure feature 18 of lower shell portion 12b of proximal half-section 10b, and distal half-section 10a is pivoted, about hinge 16, away from proximal half-section 10b to open outer shell housing 10. With outer shell housing 10 open, power-pack 101 is removed from shell cavity 10c of outer shell housing 10 (specifically from proximal half-section 10b of outer shell housing 10), and outer shell housing 10 is discarded. Power-pack 101 is then disinfected and cleaned. Power-pack 101 is not to be submerged or sterilized.

Outer shell housing 10, in addition to aseptically sealing power-pack 101 when engaged thereabout, providing an operational interface for enabling operation of surgical device 100 from the exterior of outer shell housing 10, and including electrical and mechanical pass-through features for transmitting control and drive signals between power-pack 101 and the other components of surgical device 100, further includes a memory chip, e.g., a 1-wire chip, embedded therein. The memory chip includes a memory that stores a unique ID associated with outer shell housing 10 and is capable of being updated to mark outer shell housing 10 as "used." The unique ID of outer shell housing 10 allows for exclusive pairing of outer shell housing 10 with a power-pack 101, while the ability to mark outer shell housing 10 as "used" inhibits reuse of outer shell housing 10, even with the same power-pack 101. Electrical contacts associated with the outer shell housing 10 form part of a 1-wire bus 171 (FIG. 70), or other suitable communication channel, that enables communication between power-pack 101 and the 1-wire chip of outer shell housing 10. These features will be described in greater detail below with reference to FIGS. 70-82. The 1-wire chip of outer shell housing 10, for example, may be disposed on or within plate assembly 60 thus enabling access thereto via one of the contact paths defined via pass-through connector 66. Although other locations and/or electrical couplings for enabling communication between the 1-wire chip of outer shell housing 10 and power-pack 101 are also contemplated.

Referring to FIGS. 3-6 and FIGS. 12-19, power-pack 101 includes an inner handle housing 110 having a lower housing portion 104 and an upper housing portion 108 extending from and/or supported on lower housing portion 104. Lower housing portion 104 and upper housing portion 108 are separated into a distal half-section 110a and a proximal half-section 110b connectable to distal half-section 110a by a plurality of fasteners. When joined, distal and proximal half-sections 110a, 110b define an inner handle housing 110 having an inner housing cavity 110c therein in which a power-pack core assembly 106 is situated.

Power-pack core assembly 106 is configured to control the various operations of surgical device 100, as will be set forth in additional detail below.

Distal half-section 110a of inner handle housing 110 defines a distal opening 111a therein which is configured and adapted to support a control plate 160 of power-pack core assembly 106. Control plate 160 of power-pack 101 abuts against a rear surface of plate 62 of sterile barrier plate assembly 60 of outer shell housing 10 when power-pack 101 is disposed within outer shell housing 10.

Figure 12:
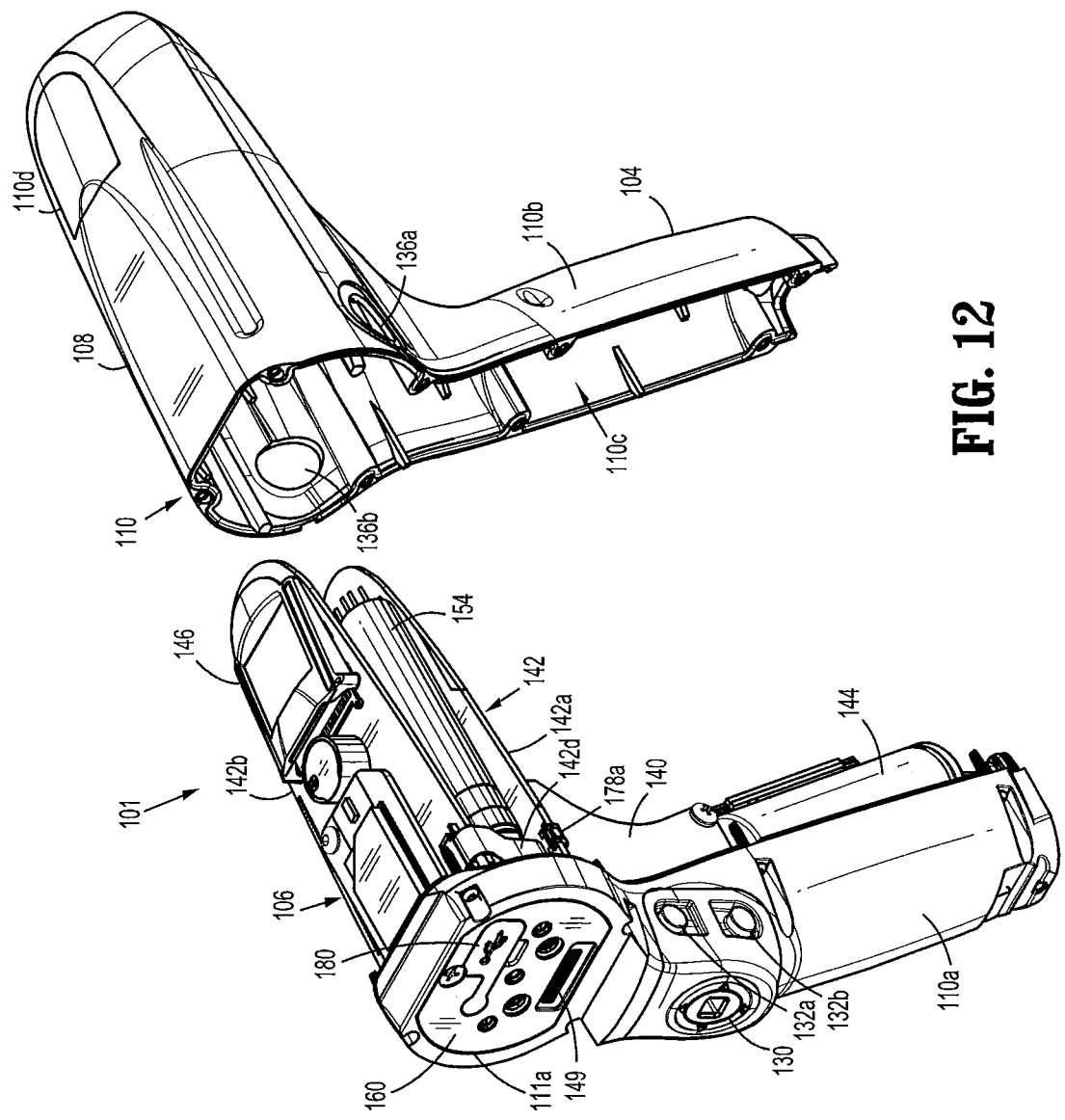
FIG. 12 is a front, perspective view of the power-pack with an inner rear housing separated therefrom.
Figure 13:
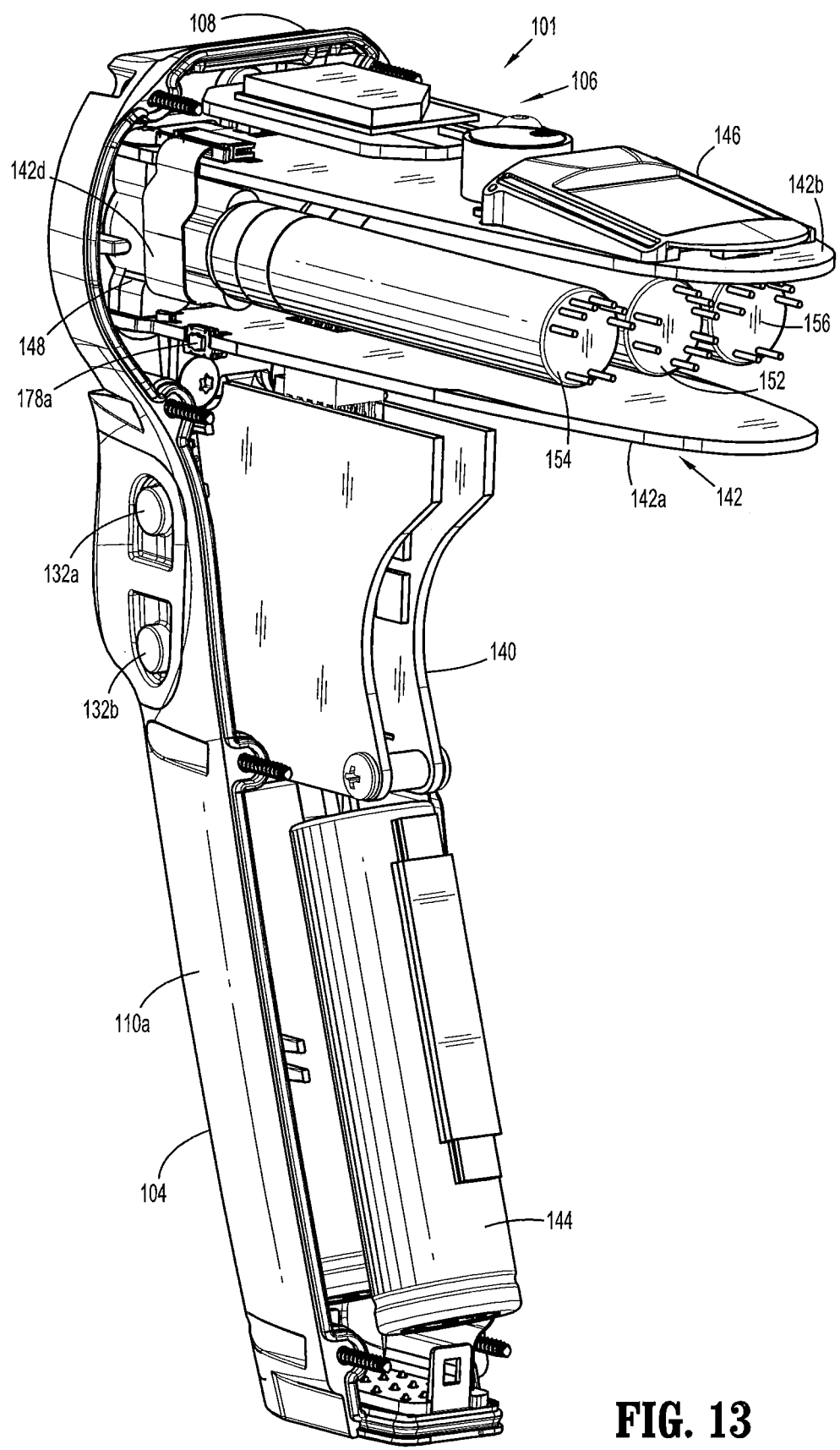
FIG. 13 is a rear, perspective view of the power-pack with the inner rear housing removed therefrom.

With reference to FIG. 12, distal half-section 110a of inner handle housing 110 supports a distal toggle control interface 130 that is in operative registration with distal toggle control button 30 of outer shell housing 10. In use, when power-pack 101 is disposed within outer shell housing 10, actuation of toggle control button 30 exerts a force on toggle control interface 130.

Distal half-section 110a of inner handle housing 110 also supports a right-side pair of control interfaces 132a, 132b, and a left-side pair of control interfaces 134a, 134b. In use, when power-pack 101 is disposed within outer shell housing 10, actuation of one of the right-side pair of control buttons 32a, 32b or the left-side pair of control button 34a, 34b of distal half-section 10a of outer shell housing 10 exerts a force on a respective one of the right-side pair of control interfaces 132a, 132b or the left-side pair of control interfaces 134a, 134b of distal half-section 110a of inner handle housing 110.

In use, right-side pair of control interfaces 132a, 132b or the left-side pair of control interfaces 134a, 134b of distal half-section 110a of inner handle housing 110 will be deactivate or fail to function unless outer shell housing 10 has been validated.

Proximal half-section 110b of inner handle housing 110 defines a right-side control aperture 136a and a left-side control aperture 136b. In use, when power-pack 101 is disposed within outer shell housing 10, actuation of one of the right-side control button 36a or the left-side control button 36b of proximal half-section 10b of outer shell housing 10 extends the right-side control button 36a or the left-side control button 36b into and across the right-side control aperture 136a or the left-side control aperture 136b of the proximal half-section 110b of inner handle housing 110.

With reference to FIGS. 12-19, inner handle housing 110 provides a housing in which power-pack core assembly 106 is situated. Power-pack core assembly 106 includes a rechargeable battery 144 configured to supply power to any of the electrical components of surgical device 100, a battery circuit board 140, and a controller circuit board 142. Controller circuit board 142 includes a motor controller circuit board 142a, a main controller circuit board 142b, and a first ribbon cable 142c interconnecting motor controller circuit board 142a and main controller circuit board 142b. The motor controller circuit board 142a is communicatively coupled with the battery circuit board 140 enabling communication therebetween and between the battery circuit board 140 and the main controller circuit board 142b.

Power-pack core assembly 106 further includes a display screen 146 supported on main controller circuit board 142b. Display screen 146 is visible through a clear or transparent window 110d (see FIGS. 12 and 17) provided in proximal half-section 110b of inner handle housing 110. It is contemplated that at least a portion of inner handle housing 110 may be fabricated from a transparent rigid plastic or the like. It is further contemplated that outer shell housing 10 may either include a window formed therein (in visual registration with display screen 146 and with window 110d of proximal half-section 110b of inner handle housing 110, and/or outer shell housing 10 may be fabricated from a transparent rigid plastic or the like.

Power-pack core assembly 106 further includes a first motor 152, a second motor 154, and a third motor 156 each electrically connected to controller circuit board 142 and battery 144. Motors 152, 154, 156 are disposed between motor controller circuit board 142a and main controller circuit board 142b. Each motor 152, 154, 156 includes a respective motor shaft 152a, 154a, 156a extending therefrom. Each motor shaft 152a, 154a, 156a has a tri-lobe transverse cross-sectional profile for transmitting rotative forces or torque. As an alternative to motors 152, 154, 156, it is envisioned that more or fewer motors be provided or that one or more other drive components be utilized, e.g., a solenoid, and controlled by appropriate controllers. Manual drive components are also contemplated.

Each motor 152, 154, 156 is controlled by a respective motor controller "MC0," MC1," "MC2." Motor controllers "MC0," MC1," "MC2" are disposed on the motor controller circuit board 142a. The motor controllers are disposed on motor controller circuit board 142a and are, for example, A3930/31K motor drivers from Allegro Microsystems, Inc. The A3930/31K motor drivers are designed to control a 3-phase brushless DC (BLDC) motor with N-channel external power MOSFETs, such as the motors 152, 154, 156. Each of the motor controllers is coupled to a main controller or master chip 157 disposed on the main controller circuit board 142b via first ribbon cable 142c which connects the motor controller circuit board 142a with the main controller circuit board 142b. The main controller 157 communicates with motor controllers "MC0," MC1," "MC2" through a field-programmable gate array (FPGA) 162, which provides control logic signals (e.g., coast, brake, etc.). The control logic of motor controllers "MC0," MC1," "MC2" then outputs corresponding energization signals to respective motor 152, 154, 156 using fixed-frequency pulse width modulation (PWM). The main controller 157 is also coupled to memory 165, which is also disposed on the main controller circuit board 142b. The main controller 157 is, for example, an ARM Cortex M4 processor from Freescale Semiconductor, Inc, which includes 1024 kilobytes of internal flash memory.

Figure 16:
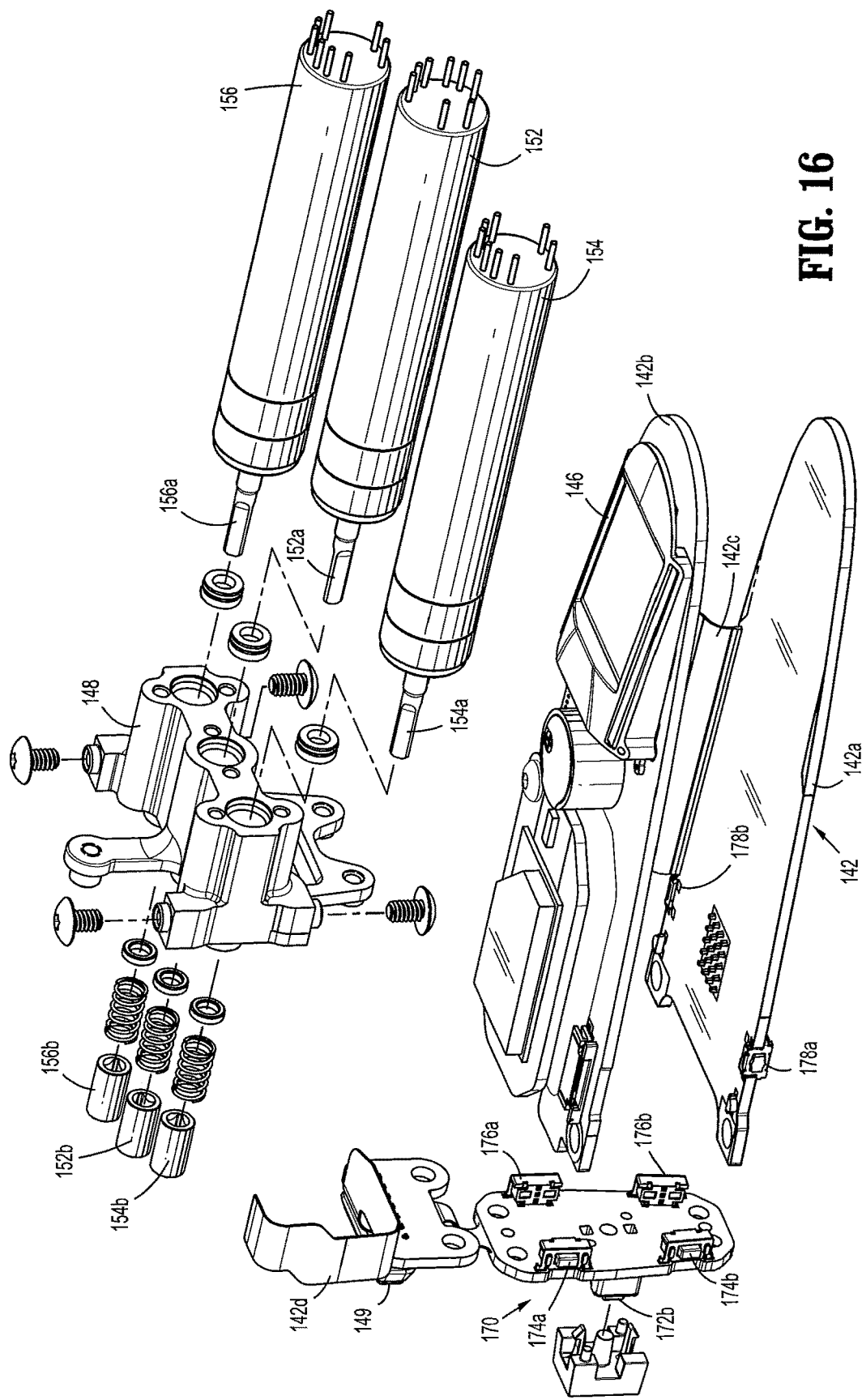
FIG. 16 is a rear, perspective view, with parts separated, of the motor assembly and the control assembly of FIG. 15.
Figure 17:
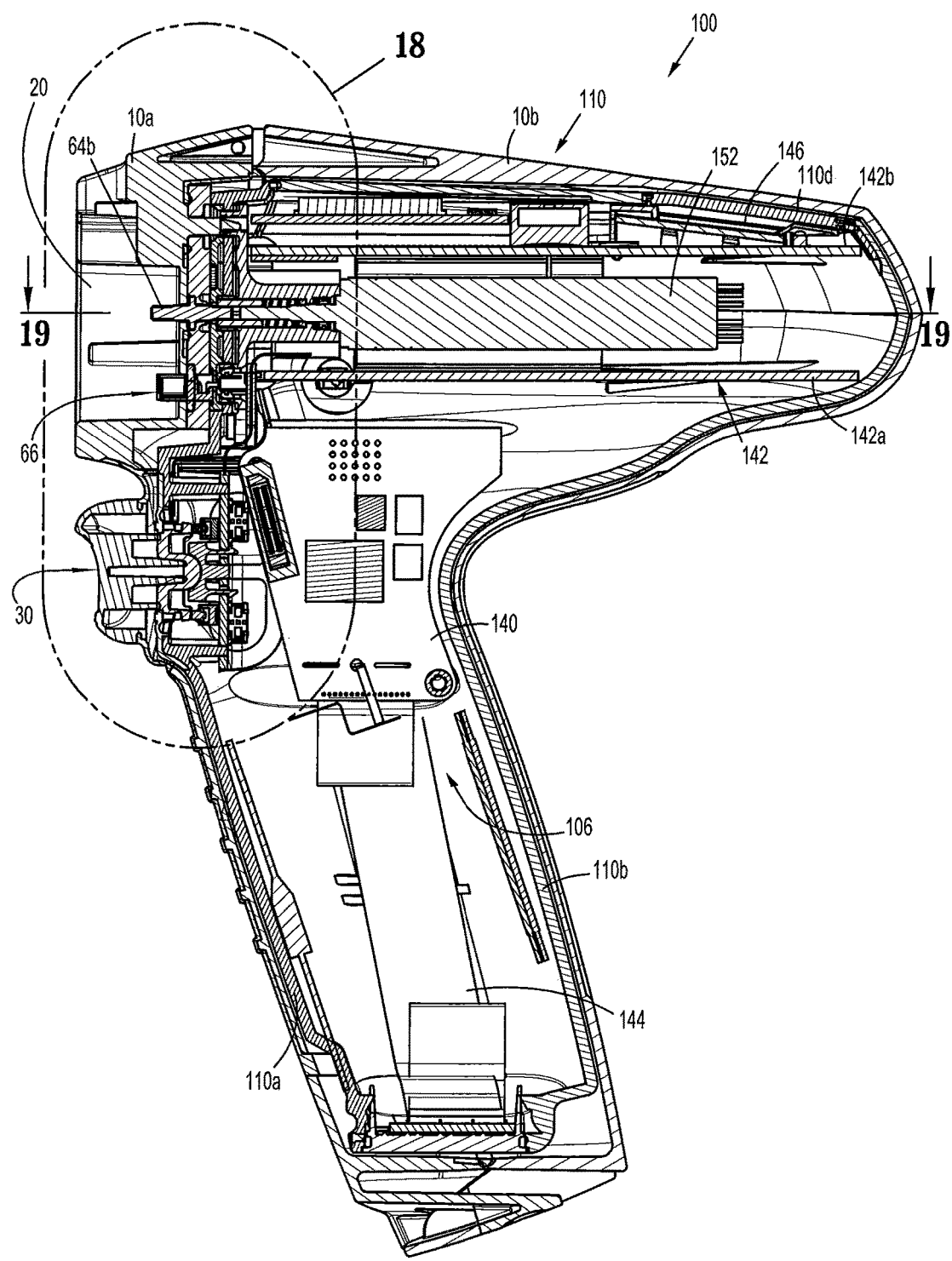
FIG. 17 is a longitudinal, cross-sectional view of the handheld surgical device of FIG. 2.
Figure 18:
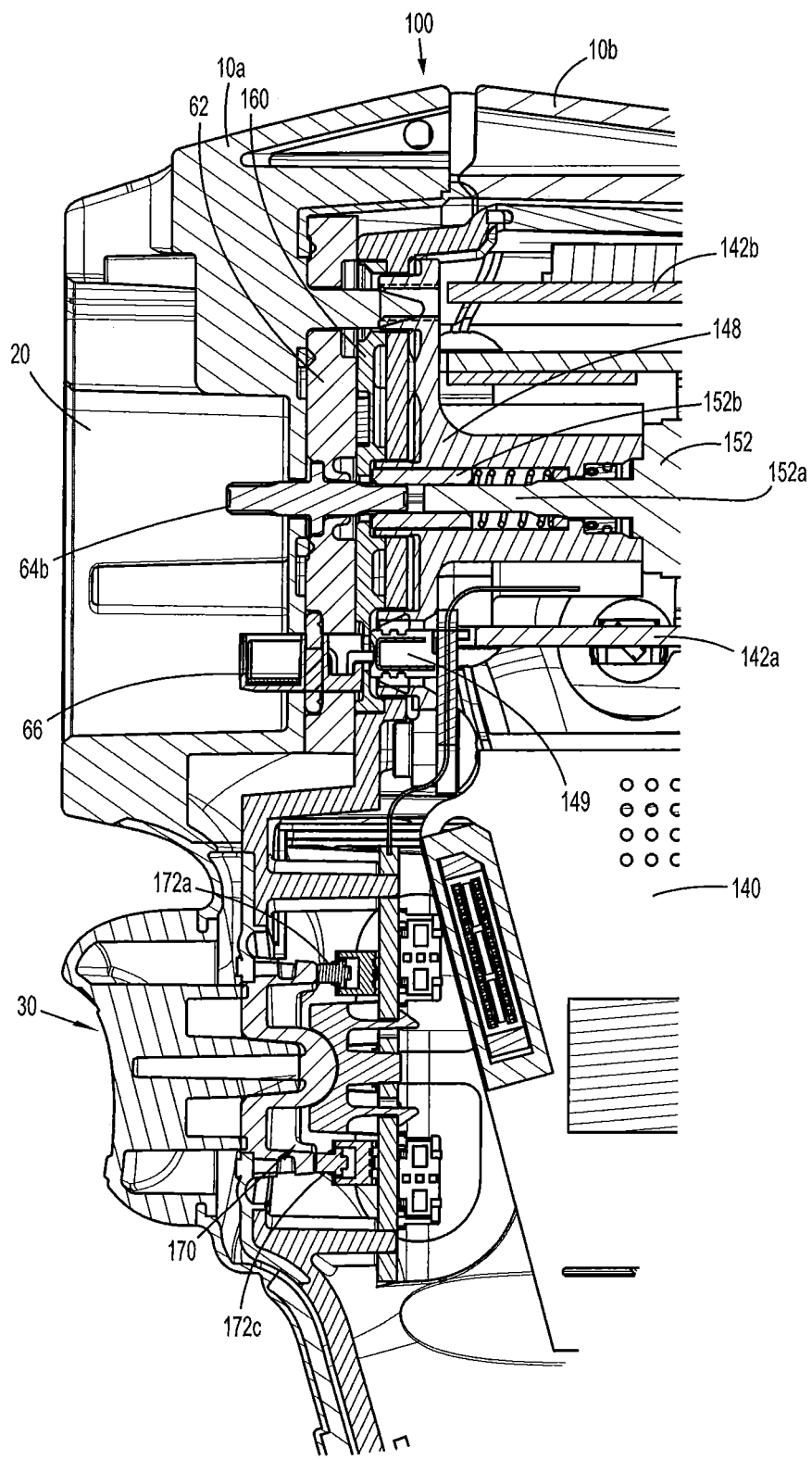
FIG. 18 is an enlarged view of the indicated area of detail of FIG. 17.
Figure 19:
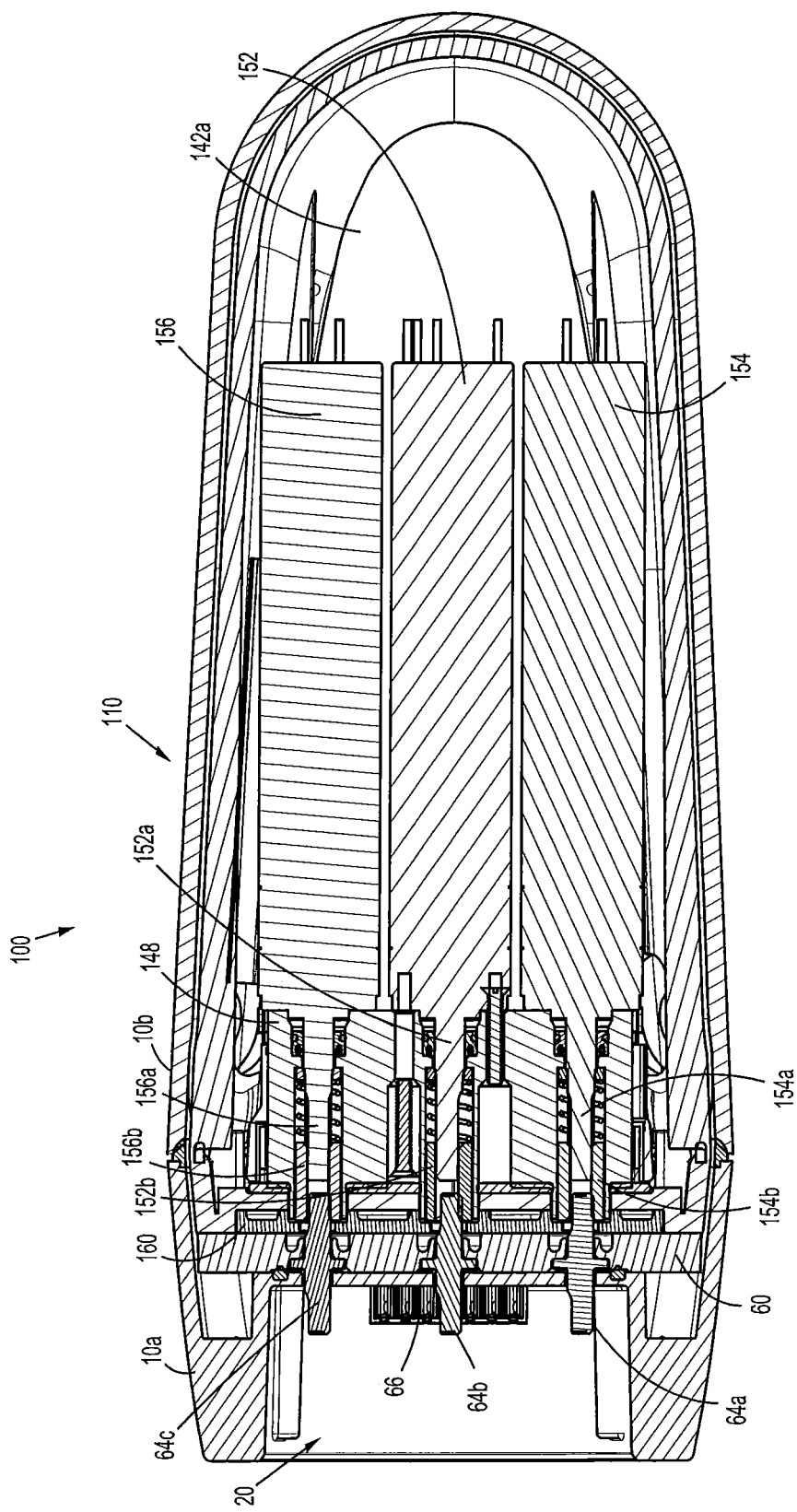
FIG. 19 is a cross-sectional view of the handheld surgical device as taken through 19-19 of FIG. 17.

Each motor 152, 154, 156 is supported on a motor bracket 148 such that motor shaft 152a, 154a, 156a are rotatably disposed within respective apertures of motor bracket 148. As illustrated in FIGS. 16 and 19, motor bracket 148 rotatably supports three rotatable drive connector sleeves 152b, 154b, 156b that are keyed to respective motor shafts 152a, 154a, 156a of motors 152, 154, 156. Drive connector sleeves 152b, 154b, 156b non-rotatably receive proximal ends of respective coupling shaft 64a, 64b, 64c of plate assembly 60 of outer shell housing 10, when power-pack 101 is disposed within outer shell housing 10. Drive connector sleeves 152b, 154b, 156b are each spring biased away from respective motors 152, 154, 156.

Rotation of motor shafts 152a, 154a, 156a by respective motors 152, 154, 156 function to drive shafts and/or gear components of adapter 200 in order to perform the various operations of surgical device 100. In particular, motors 152, 154, 156 of power-pack core assembly 106 are configured to drive shafts and/or gear components of adapter 200 in order to selectively move tool assembly 404 of SULU 400 relative to proximal body portion 402 of SULU 400, to rotate SULU 400 about a longitudinal axis "X," to move cartridge assembly 408 relative to anvil assembly 406 of SULU 400, and/or to fire staples from within cartridge assembly 408 of SULU 400.

Motor bracket 148 also supports an electrical adapter interface receptacle 149. Electrical receptacle 149 is in electrical connection with main controller circuit board 142b by a second ribbon cable 142d. Electrical receptacle 149 defines a plurality of electrical slots for receiving respective electrical contacts or blades extending from pass-through connector 66 of plate assembly 60 of outer shell housing 10.

Figure 22:
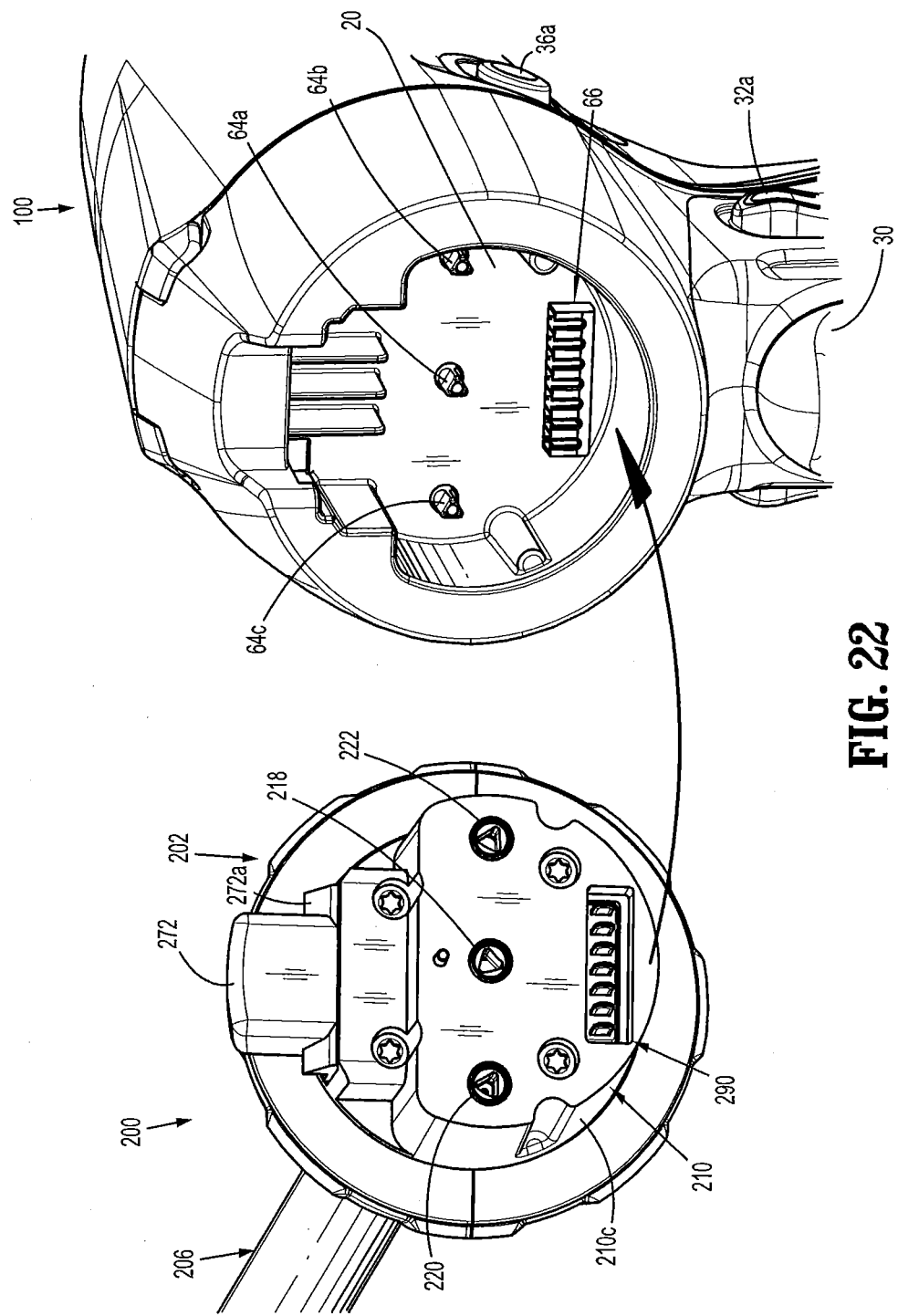
FIG. 22 is a perspective view illustrating a connection of the adapter assembly and the handheld surgical device.
Figure 25:
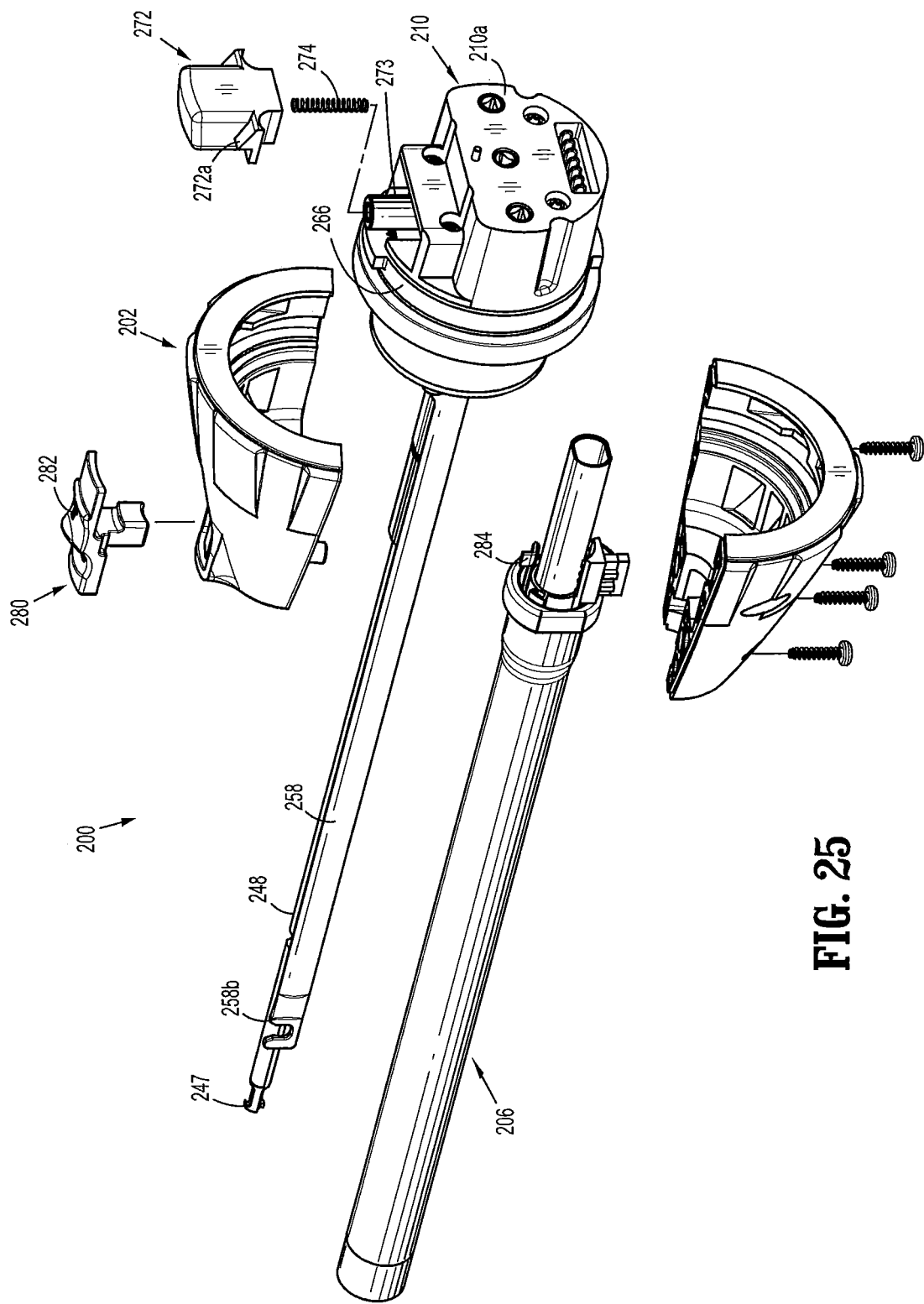
FIG. 25 is a perspective view, with parts separated, of the adapter assembly of FIGS. 1 and 20-24.

In use, when adapter 200 is mated to surgical device 100, each of coupling shaft 64a, 64b, 64c of plate assembly 60 of outer shell housing 10 of surgical device 100 couples with a corresponding rotatable connector sleeves 218, 220, 222 of adapter 200 (see FIG. 22). In this regard, the interface between corresponding first coupling shaft 64a and first connector sleeve 218, the interface between corresponding second coupling shaft 64b and second connector sleeve 220, and the interface between corresponding third coupling shaft 64c and third connector sleeve 222 are keyed such that rotation of each of coupling shafts 64a, 64b, 64c of surgical device 100 causes a corresponding rotation of the corresponding connector sleeve 218, 220, 222 of adapter 200. The identification, verification, and other communications between power-pack 101 and adapter 200 upon engagement therebetween are detailed below with respect to FIGS. 70-82.

The mating of coupling shafts 64a, 64b, 64c of surgical device 100 with connector sleeves 218, 220, 222 of adapter 200 allows rotational forces to be independently transmitted via each of the three respective connector interfaces. The coupling shafts 64a, 64b, 64c of surgical device 100 are configured to be independently rotated by respective motors 152, 154, 156.

Since each of coupling shafts 64a, 64b, 64c of surgical device 100 has a keyed and/or substantially non-rotatable interface with respective connector sleeves 218, 220, 222 of adapter 200, when adapter 200 is coupled to surgical device 100, rotational force(s) are selectively transferred from motors 152, 154, 156 of surgical device 100 to adapter 200.

The selective rotation of coupling shaft(s) 64a, 64b, 64c of surgical device 100 allows surgical device 100 to selectively actuate different functions of SULU 400. As will be discussed in greater detail below, selective and independent rotation of first coupling shaft 64a of surgical device 100 corresponds to the selective and independent opening and closing of tool assembly 404 of SULU 400, and driving of a stapling/cutting component of tool assembly 404 of SULU 400. Also, the selective and independent rotation of second coupling shaft 64b of surgical device 100 corresponds to the selective and independent articulation of tool assembly 404 of SULU 400 transverse to longitudinal axis "X" (see FIG. 21). Additionally, the selective and independent rotation of third coupling shaft 64c of surgical device 100 corresponds to the selective and independent rotation of SULU 400 about longitudinal axis "X" (see FIG. 21) relative to surgical device 100.

With reference to FIGS. 12-19, power-pack core assembly 106 further includes a switch assembly 170 supported within distal half-section 110a of inner handle housing 110, at a location beneath and in registration with toggle control interface 130, the right-side pair of control interfaces 132a, 132b, and the left-side pair of control interfaces 134a, 134b. Switch assembly 170 includes a first set of four push-button switches 172a-172d arranged around stem 30a of toggle control button 30 of outer shell housing 10 when power-pack 101 is disposed within outer shell housing 10. Switch assembly 170 also includes a second pair of push-button switches 174a, 174b disposed beneath right-side pair of control interfaces 132a, 132b of distal half-section 110a of inner handle housing 110 when power-pack 101 is disposed within outer shell housing 10. Switch assembly 170 further includes a third pair of push-button switches 176a, 176b disposed beneath left-side pair of control interfaces 134a, 134b of distal half-section 110a of inner handle housing 110 when power-pack 101 is disposed within outer shell housing 10.

Power-pack core assembly 106 includes a single right-side push-button switch 178a disposed beneath right-side control aperture 136a of proximal half-section 110b of inner handle housing 110, and a single left-side push-button switch 178b disposed beneath left-side control aperture 136b of proximal half-section 110b of inner handle housing 110. Push-button switches 178a, 178b are supported on controller circuit board 142. Push-button switches 178a, 178b are disposed beneath right-side control button 36a and left-side control button 36b of proximal half-section 10b of outer shell housing 10 when power-pack 101 is disposed within outer shell housing 10. Actuation of right or left-side control button 36a, 36b actuates the respective right or left safety switches or keys 178a, 178b to permit entry of power-pack core assembly 106 into the firing state. Entry into the firing state instructs surgical device 100 that SULU 400 is ready to expel fasteners therefrom.

The actuation of push button switch 172c, corresponding to a downward actuation of toggle control button 30, causes controller circuit board 142 to provide appropriate signals to motor 152 to close a tool assembly 404 of SULU 400 and/or to fire staples from within cartridge assembly 408 of SULU 400.

The actuation of push button switch 172a, corresponding to an upward actuation of toggle control button 30, causes controller circuit board 142 to provide appropriate signals to motor 152 to retract a staple sled and open tool assembly 404 of SULU 400.

The actuation of push button 172d, corresponding to an actuation of toggle control button 30 to the right, causes controller circuit board 142 to provide appropriate signals to motor 152 to articulate tool assembly 404 to the right relative to body portion 402 of SULU 400. Similarly, the actuation of push button 172b, corresponding to an actuation of toggle control button 30 to the left, causes controller circuit board 142 to provide appropriate signals to motor 152 to articulate tool assembly 404 to the left relative to body portion 402 of SULU 400.

The actuation of switches 174a, 174b (by right-hand thumb of user) or switches 176a, 176b (by left-hand thumb of user), corresponding to respective actuation of right-side pair of control buttons 32a, 32b or left-side pair of control button 34a, 34b, causes controller circuit board 142 to provide appropriate signals to motor 154 to rotate SULU 400 relative to surgical device 100. Specifically, actuation of control button 32a or 34a causes SULU 400 to rotate relative to surgical device 100 in a first direction, while actuation of control button 32b or 34b causes SULU 400 to rotate relative to surgical device 100 in an opposite, e.g., second, direction.

In use, tool assembly 404 of SULU 400 is actuated between opened and closed conditions as needed and/or desired. In order to fire SULU 400, to expel fasteners therefrom, when tool assembly 404 of SULU 400 is in a closed condition, safety switch 178a or 178b is depressed thereby instructing surgical device 100 that SULU 400 is ready to expel fasteners therefrom.

Figure 14:
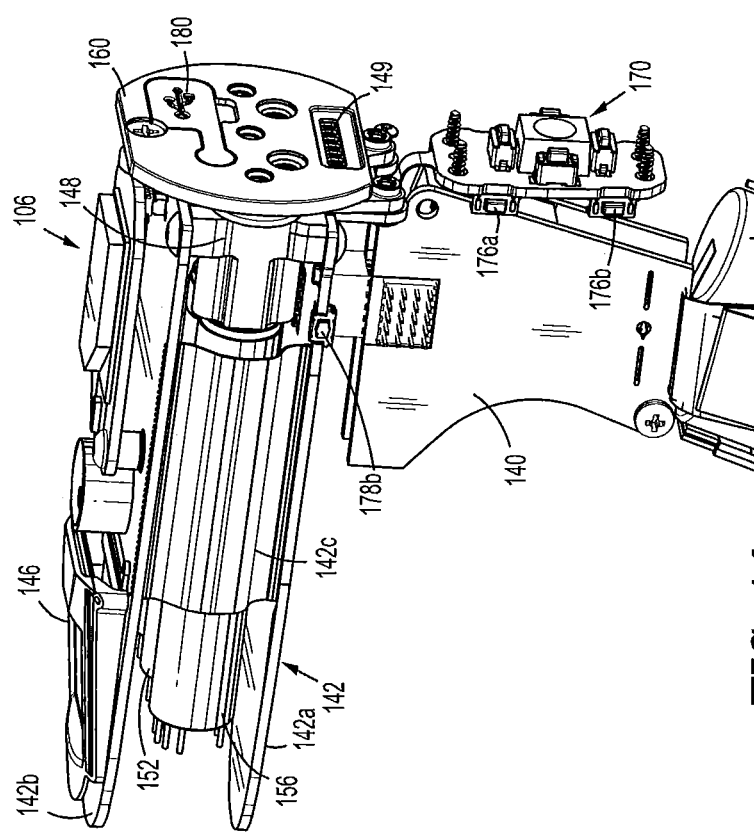
FIG. 14 is a perspective view of a power-pack core assembly of the power-pack.

With reference to FIGS. 12 and 14, power-pack core assembly 106 of surgical device 100 includes a USB connector 180 supported on main controller circuit board 142b of controller circuit board 142. USB connector 180 is accessible through control plate 160 of power-pack core assembly 106. When power-pack 101 is disposed within outer shell housing 10, USB connector 180 is covered by plate 62 of sterile barrier plate assembly 60 of outer shell housing 10.

As illustrated in FIG. 1 and FIGS. 20-52, surgical device 100 is configured for selective connection with one or more different types of adapters, e.g., adapter 200, and, in turn, the adapter 200 is configured for selective connection with one or more different types of loading units, e.g., SULU 400, a loading unit 900 (FIG. 69), a multi-use loading unit (MULU) having a configuration similar to that of SULU 400 or loading unit 900 (FIG. 69), etc.

Figure 54:
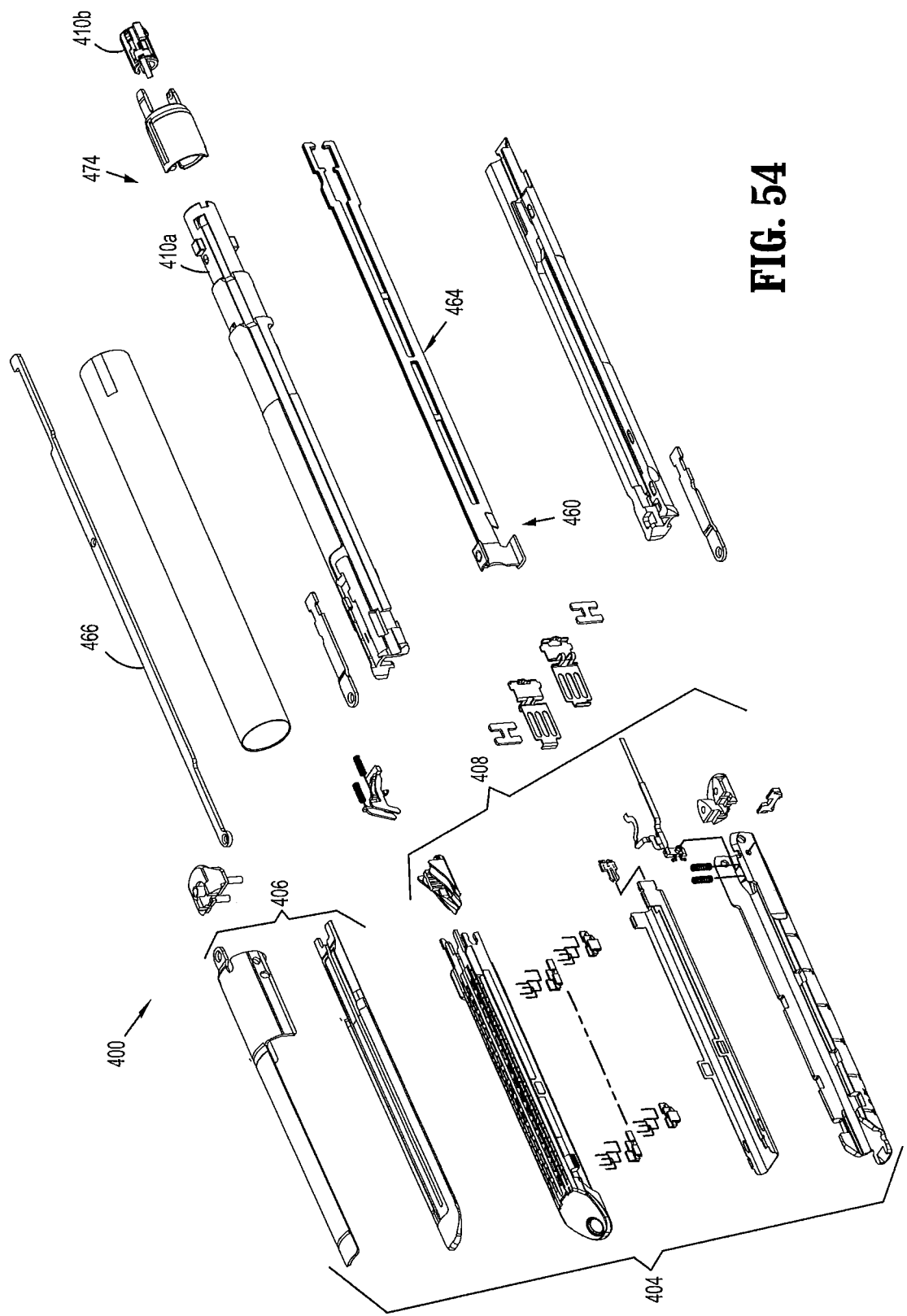
FIG. 54 is a perspective view, with parts separated, of the loading unit of FIGS. 1 and 53.
Figure 55:
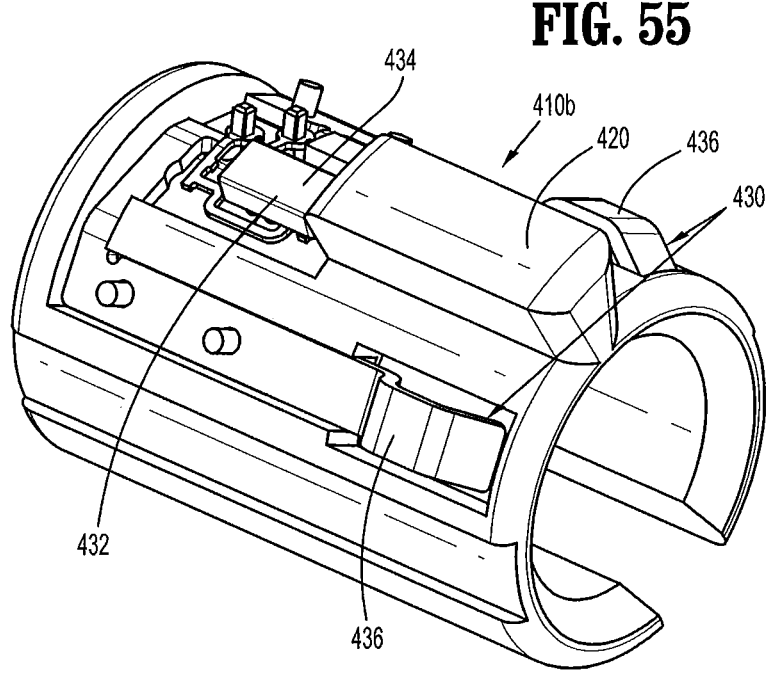
FIGS. 55 and 56 are alternate perspective views of an inner housing of the loading unit shown in FIGS. 1 and 53-54.
Figure 56:
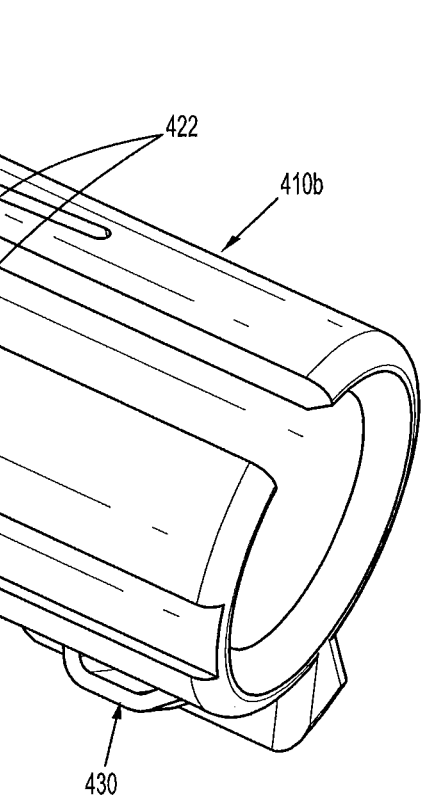

Adapter 200 is configured to convert a rotation of either of drive connector sleeve 152b or 156b of surgical device 100 into axial translation useful for operating a drive assembly 460 and an articulation link 466 of SULU 400, as illustrated in FIG. 54, and as will be discussed in greater detail below.

Adapter 200 includes a first drive transmitting/converting assembly for interconnecting first drive connector sleeve 152a of surgical device 100 and a first axially translatable drive member of SULU 400, wherein the first drive transmitting/converting assembly converts and transmits a rotation of first drive connector sleeve 152a of surgical device 100 to an axial translation of the first axially translatable drive assembly 460 of SULU 400 for firing.

Adapter 200 includes a second drive transmitting/converting assembly for interconnecting third drive connector sleeve 156b of surgical device 100 and a second axially translatable drive member of SULU 400, wherein the second drive transmitting/converting assembly converts and transmits a rotation of third drive connector sleeve 156b of surgical device 100 to an axial translation of articulation link 466 of SULU 400 for articulation.

Turning now to FIGS. 21-47, adapter 200 includes an outer knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, that outer tube is passable through a typical trocar port, cannula or the like. Knob housing 202 is dimensioned to not enter the trocar port, cannula of the like. Knob housing 202 is configured and adapted to connect to connecting portion 108 of handle housing 102 of surgical device 100.

Adapter 200 is configured to convert a rotation of either of first or second coupling shafts 64a, 64b of surgical device 100 into axial translation useful for operating a drive assembly 460 and an articulation link 466 of SULU 400, as illustrated in FIG. 54 and as will be described in greater detail below. As illustrated in FIGS. 26 and 38-47, adapter 200 includes a proximal inner housing assembly 204 rotatably supporting a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective coupling shafts 64a, 64b and 64c of surgical device 100, as described in greater detail below.

As described briefly above, drive coupling assembly 210 of adapter 200 is also configured to rotatably support first, second and third connector sleeves 218, 222 and 220, respectively, arranged in a common plane or line with one another. Each of connector sleeves 218, 222, 220 is configured to mate with respective first, second and third coupling shafts 64a, 64c and 64b of surgical device 100, as described above. Each of connector sleeves 218, 222, 220 is further configured to mate with a proximal end of respective first, second and third proximal drive shafts 212, 214, 216 of adapter 200.

Drive coupling assembly 210 of adapter 200 also includes, as illustrated in FIGS. 26, 38 and 41-44, a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 222 and 220 to help maintain connector sleeves 218, 222 and 220 engaged with the distal end of respective coupling shafts 64a, 64c and 64b of surgical device 100 when adapter 200 is connected to surgical device 100.

In particular, first, second and third biasing members 224, 226 and 228 function to bias respective connector sleeves 218, 222 and 220 in a proximal direction. In this manner, during connection of surgical device 100 when adapter 200 to surgical device 100, if first, second and or third connector sleeves 218, 222 and/or 220 is/are misaligned with coupling shafts 64a, 64c and 64b of surgical device 100, first, second and/or third biasing member(s) 224, 226 and/or 228 are compressed. Thus, when surgical device 100 is operated, coupling shafts 64a, 64c and 64b of surgical device 100 will rotate and first, second and/or third biasing member(s) 224, 226 and/or 228 will cause respective first, second and/or third connector sleeve(s) 218, 222 and/or 220 to slide back proximally, effectively connecting coupling shafts 64a, 64c and 64b of surgical device 100 to first, second and/or third proximal drive shaft(s) 212, 214 and 216 of drive coupling assembly 210.

Adapter 200 includes a plurality of force/rotation transmitting/converting assemblies, each disposed within inner housing assembly 204 and outer tube 206. Each force/rotation transmitting/converting assembly is configured and adapted to transmit/convert a speed/force of rotation (e.g., increase or decrease) of first, second and third rotatable coupling shafts 64a, 64c and 64b of surgical device 100 before transmission of such rotational speed/force to SULU 400.

Figure 26:
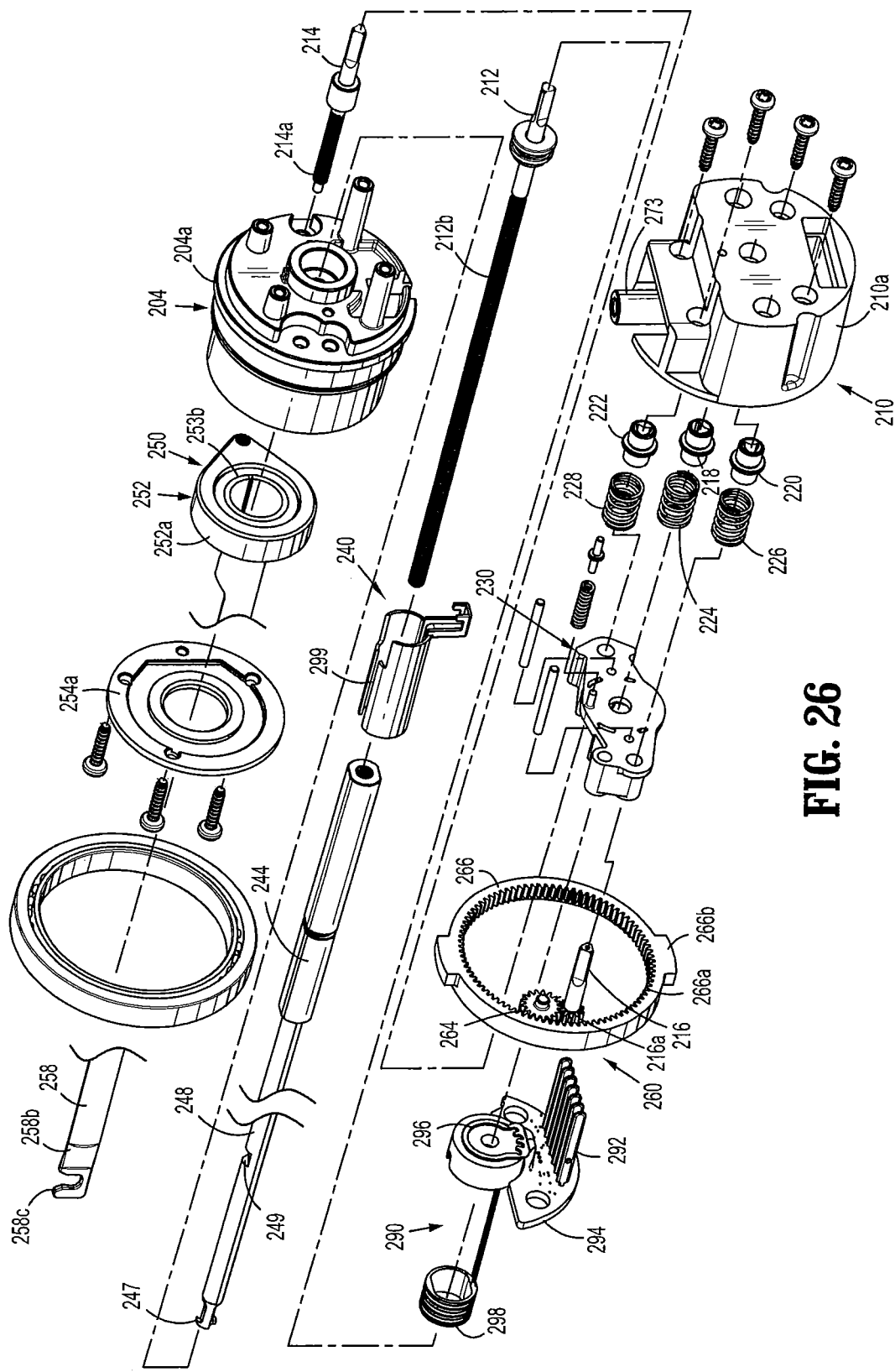
FIG. 26 is a rear, perspective view of the adapter assembly of FIGS. 1 and 20-25, with most parts thereof separated.
Figure 27:
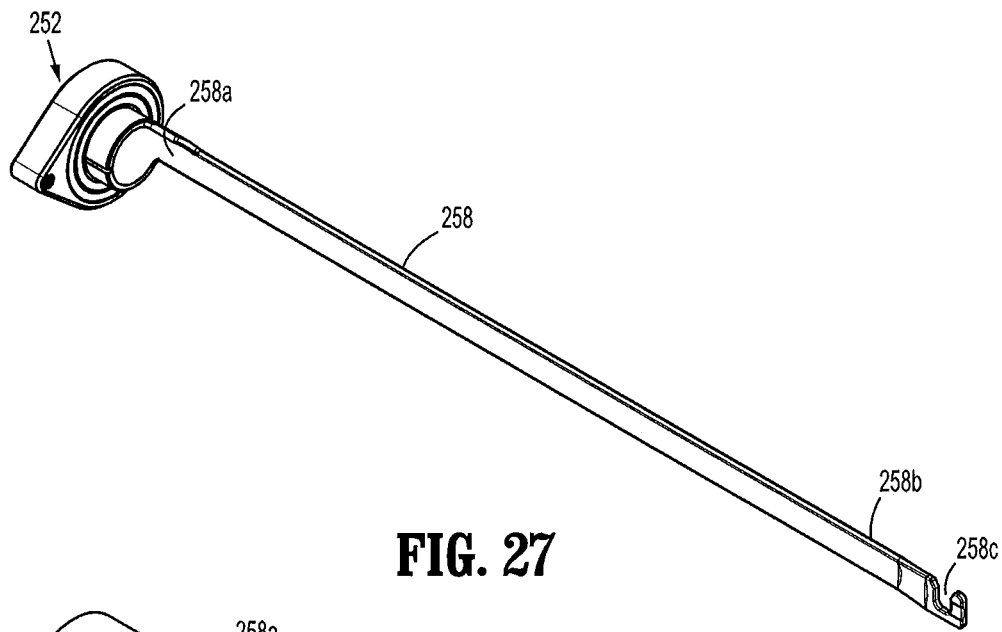
FIG. 27 is a perspective view of an articulation assembly of the adapter assembly of FIGS. 1 and 20-26.
Figure 28:
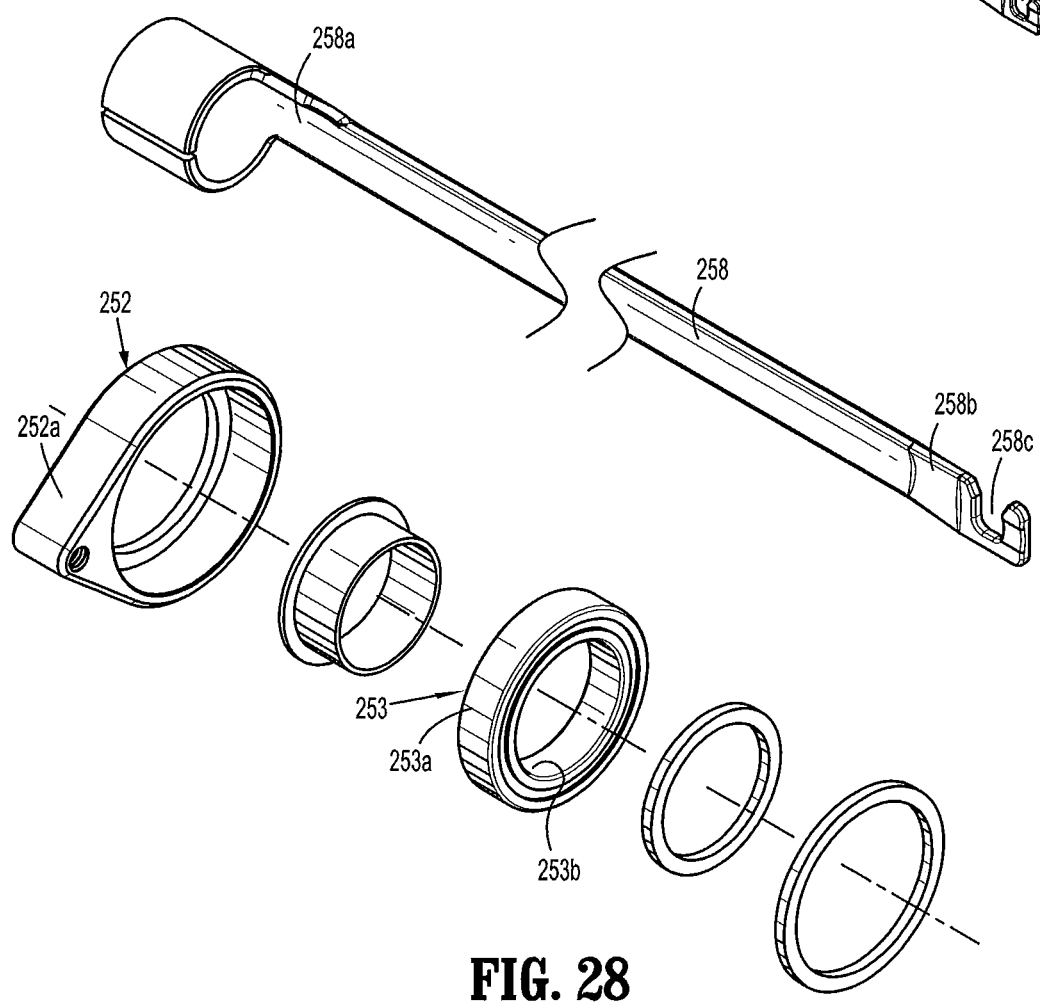
FIG. 28 is an enlarged, perspective view, with parts separated, of the articulation assembly of FIG. 27.
Figure 29:
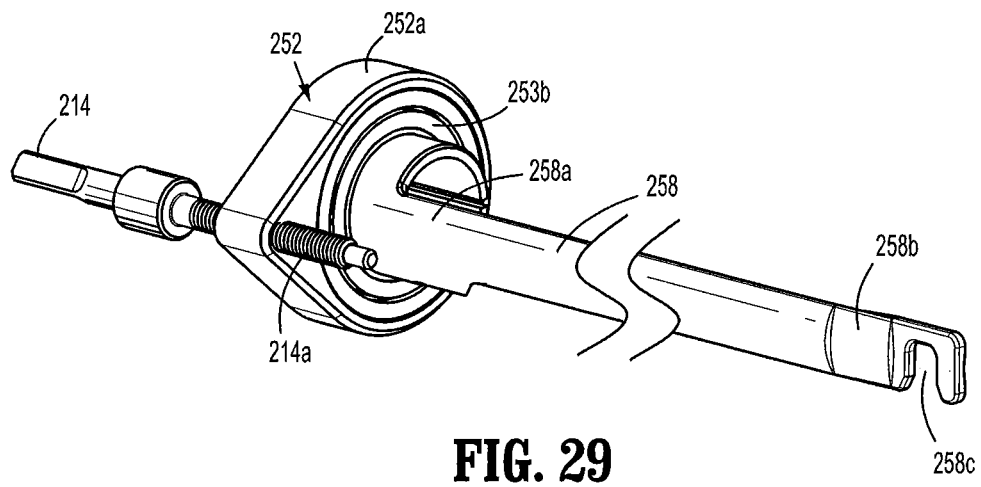
FIG. 29 is a perspective view of the articulation assembly of FIG. 27, shown in a first orientation.
Figure 30:
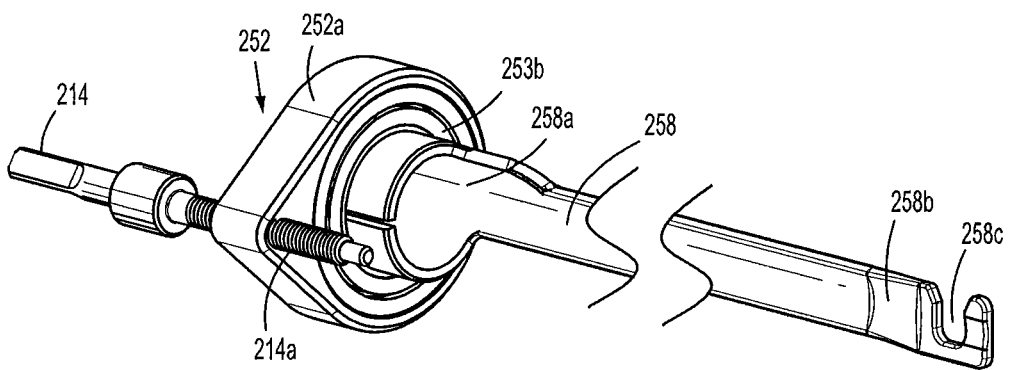
FIG. 30 is a perspective view of the articulation assembly of FIG. 27, shown in a second orientation.
Figure 31:
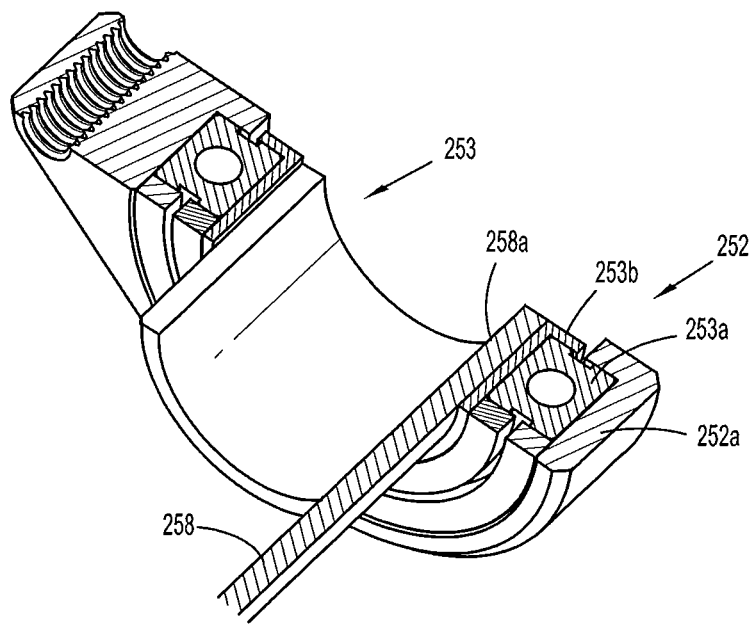
FIG. 31 is a cross-sectional view of the articulation assembly of FIG. 29.

Specifically, as illustrated in FIG. 26, adapter 200 includes a first, a second and a third force/rotation transmitting/converting assembly 240, 250, 260, respectively, disposed within inner housing assembly 204 and outer tube 206. Each force/rotation transmitting/converting assembly 240, 250, 260 is configured and adapted to transmit or convert a rotation of a first, second and third coupling shafts 64a, 64c and 64b of surgical device 100 into axial translation of articulation bar 258 of adapter 200, to effectuate articulation of SULU 400; a rotation of a ring gear 266 of adapter 200, to effectuate rotation of adapter 200; or axial translation of a distal drive member 248 of adapter 200 to effectuate closing, opening and firing of SULU 400.

As shown in FIGS. 26 and 41-45, first force/rotation transmitting/converting assembly 240 includes first rotatable proximal drive shaft 212, which, as described above, is rotatably supported within inner housing assembly 204. First rotatable proximal drive shaft 212 includes a non-circular or shaped proximal end portion configured for connection with first connector 218 which is connected to respective first coupling shaft 64a of surgical device 100. First rotatable proximal drive shaft 212 includes a distal end portion 212b having a threaded outer profile or surface.

First force/rotation transmitting/converting assembly 240 further includes a drive coupling nut 244 rotatably coupled to threaded distal end portion 212b of first rotatable proximal drive shaft 212, and which is slidably disposed within outer tube 206. Drive coupling nut 244 is slidably keyed within proximal core tube portion of outer tube 206 so as to be prevented from rotation as first rotatable proximal drive shaft 212 is rotated. In this manner, as first rotatable proximal drive shaft 212 is rotated, drive coupling nut 244 is translated along threaded distal end portion 212b of first rotatable proximal drive shaft 212 and, in turn, through and/or along outer tube 206.

First force/rotation transmitting/converting assembly 240 further includes a distal drive member 248 that is mechanically engaged with drive coupling nut 244, such that axial movement of drive coupling nut 244 results in a corresponding amount of axial movement of distal drive member 248. The distal end portion of distal drive member 248 supports a connection member 247 configured and dimensioned for selective engagement with a drive member 474 of drive assembly 460 of SULU 400 (FIG. 54). Drive coupling nut 244 and/or distal drive member 248 function as a force transmitting member to components of SULU 400, as described in greater detail below.

In operation, as first rotatable proximal drive shaft 212 is rotated, due to a rotation of first connector sleeve 218, as a result of the rotation of first coupling shaft 64a of surgical device 100, drive coupling nut 244 is caused to be translated axially along first distal drive shaft 242. As drive coupling nut 244 is caused to be translated axially along first distal drive shaft 242, distal drive member 248 is caused to be translated axially relative to outer tube 206. As distal drive member 248 is translated axially, with connection member 247 connected thereto and engaged with drive member 474 of drive assembly 460 of SULU 400 (FIG. 54), distal drive member 248 causes concomitant axial translation of drive member 474 of SULU 400 to effectuate a closure of tool assembly 404 and a firing of tool assembly 404 of SULU 400.

With reference to FIGS. 26-31, 45 and 46, second drive converter assembly 250 of adapter 200 includes second proximal drive shaft 214 rotatably supported within inner housing assembly 204. Second rotatable proximal drive shaft 214 includes a non-circular or shaped proximal end portion configured for connection with second connector or coupler 222 which is connected to respective second coupling shaft 64c of surgical device 100. Second rotatable proximal drive shaft 214 further includes a distal end portion 214b having a threaded outer profile or surface.

Distal end portion 214a of proximal drive shaft 214 is threadably engaged with an articulation bearing housing 252a of an articulation bearing assembly 252. Articulation bearing assembly 252 includes a housing 252a supporting an articulation bearing 253 having an inner race 253b that is independently rotatable relative to an outer race 253a. Articulation bearing housing 252a has a non-circular outer profile, for example tear-dropped shaped, that is slidably and non-rotatably disposed within a complementary bore 204c (FIGS. 45 and 46) of inner housing hub 204a.

Second drive converter assembly 250 of adapter 200 further includes an articulation bar 258 having a proximal portion 258a secured to inner race 253b of articulation bearing 253. A distal portion 258b of articulation bar 258 includes a slot 258c therein, which is configured to accept a flag of the articulation link 466 (FIG. 54) of SULU 400. Articulation bar 258 functions as a force transmitting member to components of SULU 400, as described in greater detail below.

With further regard to articulation bearing assembly 252, articulation bearing assembly 252 is both rotatable and longitudinally translatable. Additionally, it is envisioned that articulation bearing assembly 252 allows for free, unimpeded rotational movement of SULU 400 when its jaw members 406, 408 are in an approximated position and/or when jaw members 406, 408 are articulated.

In operation, as second proximal drive shaft 214 is rotated due to a rotation of second connector sleeve 222, as a result of the rotation of the second coupling shaft 64c of surgical device 100, articulation bearing assembly 252 is caused to be translated axially along threaded distal end portion 214b of second proximal drive shaft 214, which in turn causes articulation bar 258 to be axially translated relative to outer tube 206. As articulation bar 258 is translated axially, articulation bar 258, being coupled to articulation link 466 of SULU 400, causes concomitant axial translation of articulation link 466 of SULU 400 to effectuate an articulation of tool assembly 404. Articulation bar 258 is secured to inner race 253b of articulation bearing 253 and is thus free to rotate about the longitudinal axis X-X relative to outer race 253a of articulation bearing 253.

As illustrated in FIGS. 26, 38, 39, 43, 44 and 47, and as described, adapter 200 includes a third force/rotation transmitting/converting assembly 260 supported in inner housing assembly 204. Third force/rotation transmitting/converting assembly 260 includes a rotation ring gear 266 fixedly supported in and connected to outer knob housing 202. Ring gear 266 defines an internal array of gear teeth 266a (FIG. 26). Ring gear 266 includes a pair of diametrically opposed, radially extending protrusions 266b (FIG. 26) projecting from an outer edge thereof. Protrusions 266b are disposed within recesses defined in outer knob housing 202, such that rotation of ring gear 266 results in rotation of outer knob housing 202, and vice a versa.

Third force/rotation transmitting/converting assembly 260 further includes third rotatable proximal drive shaft 216 which, as described above, is rotatably supported within inner housing assembly 204. Third rotatable proximal drive shaft 216 includes a non-circular or shaped proximal end portion configured for connection with third connector 220 which is connected to respective third connector 122 of surgical device 100. Third rotatable proximal drive shaft 216 includes a spur gear 216a keyed to a distal end thereof. A reversing spur gear 264 inter-engages spur gear 216a of third rotatable proximal drive shaft 216 to gear teeth 266a of ring gear 266.

In operation, as third rotatable proximal drive shaft 216 is rotated, due to a rotation of third connector sleeve 220, as a result of the rotation of the third coupling shaft 64b of surgical device 100, spur gear 216a of third rotatable proximal drive shaft 216 engages reversing gear 264 causing reversing gear 264 to rotate. As reversing gear 264 rotates, ring gear 266 also rotates thereby causing outer knob housing 202 to rotate. As outer knob housing 202 is rotated, outer tube 206 is caused to be rotated about longitudinal axis "X" of adapter 200. As outer tube 206 is rotated, SULU 400, that is connected to a distal end portion of adapter 200, is also caused to be rotated about a longitudinal axis of adapter 200.

Adapter 200 further includes, as seen in FIGS. 22-25, an attachment/detachment button 272 supported thereon. Specifically, button 272 is supported on a stem 273 (FIGS. 25, 26, 41 and 42) projecting from drive coupling assembly 210 of adapter 200, and is biased by a biasing member 274, disposed within or around stem 273, to an un-actuated condition. Button 272 includes a lip or ledge 272a formed therewith that is configured to snap behind a corresponding lip or ledge 108b defined along recess 108a of connecting portion 108 of handle housing 102 of surgical device 100. While stem 273 is illustrated as having a relatively longer length to improve/increase stability of button 272 during actuation, it is envisioned that stem 273 may have a relatively shorter length than the length depicted.

In use, when adapter 200 is connected to surgical device 100, lip 272a of button 272 is disposed behind lip 108b of connecting portion 108 of handle housing 102 of surgical device 100 to secure and retain adapter 200 and surgical device 100 with one another. In order to permit disconnection of adapter 200 and surgical device 100 from one another, button 272 is depressed or actuated, against the bias of biasing member 274, to disengage lip 272a of button 272 and lip 108b of connecting portion 108 of handle housing 102 of surgical device 100.

With reference to FIGS. 23-25 and 48-52, adapter 200 further includes a lock mechanism 280 for fixing the axial position of distal drive member 248. Lock mechanism 280 includes a button 282 slidably supported on outer knob housing 202. Lock button 282 is connected to an actuation bar 284 that extends longitudinally through outer tube 206. Actuation bar 284 moves upon a movement of lock button 282.

In operation, in order to lock the position and/or orientation of distal drive member 248, a user moves lock button 282 from a distal position to a proximal position (FIGS. 25 and 41), thereby causing the lock out (not shown) to move proximally such that a distal face of the lock out moves out of contact with camming member 288, which causes camming member 288 to cam into recess 249 of distal drive member 248. In this manner, distal drive member 248 is prevented from distal and/or proximal movement. When lock button 282 is moved from the proximal position to the distal position, the distal end of actuation bar 284 moves distally into the lock out (not shown), against the bias of a biasing member (not shown), to force camming member 288 out of recess 249, thereby allowing unimpeded axial translation and radial movement of distal drive member 248.

With reference to FIGS. 32-39, adapter 200 includes an electrical assembly 290 supported on and in outer knob housing 202 and inner housing assembly 204. Electrical assembly 290 includes a plurality of electrical contact blades 292, supported on a circuit board 294, for electrical connection to pass-through connector 66 of plate assembly 60 of outer shell housing 10 of surgical device 100. Electrical assembly 290 serves to allow for calibration and communication information (i.e., identifying information, life-cycle information, system information, force information) to the main controller circuit board 142b of power-pack core assembly 106 via electrical receptacle 149 of power-pack core assembly 106 of surgical device 100. Such communication is described in greater detail below with reference to FIGS. 70-82.

Figure 32:
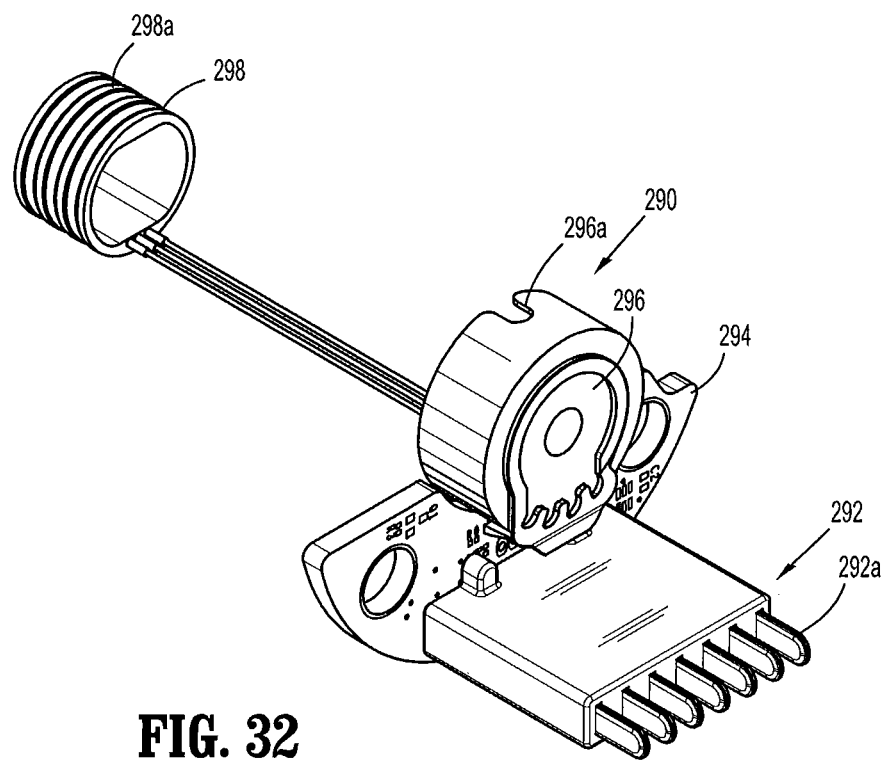
FIG. 32 is a perspective view of an electrical assembly of the adapter assembly of FIGS. 1 and 20-26.
Figure 35:
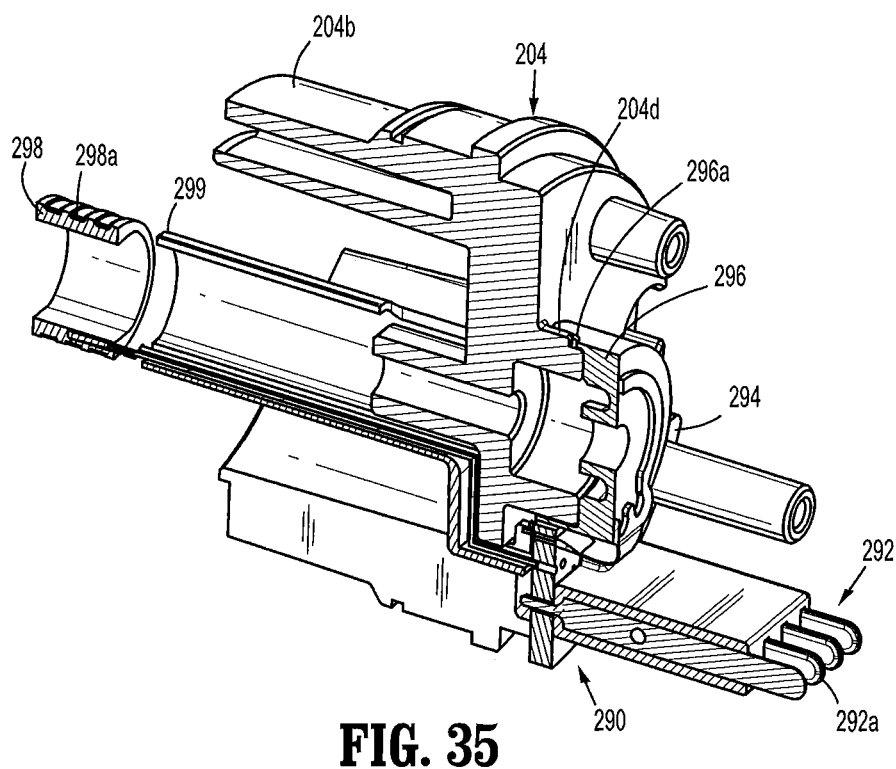
FIG. 35 is a cross-sectional view as taken along section line 35-35 of FIG. 33.
Figure 36:
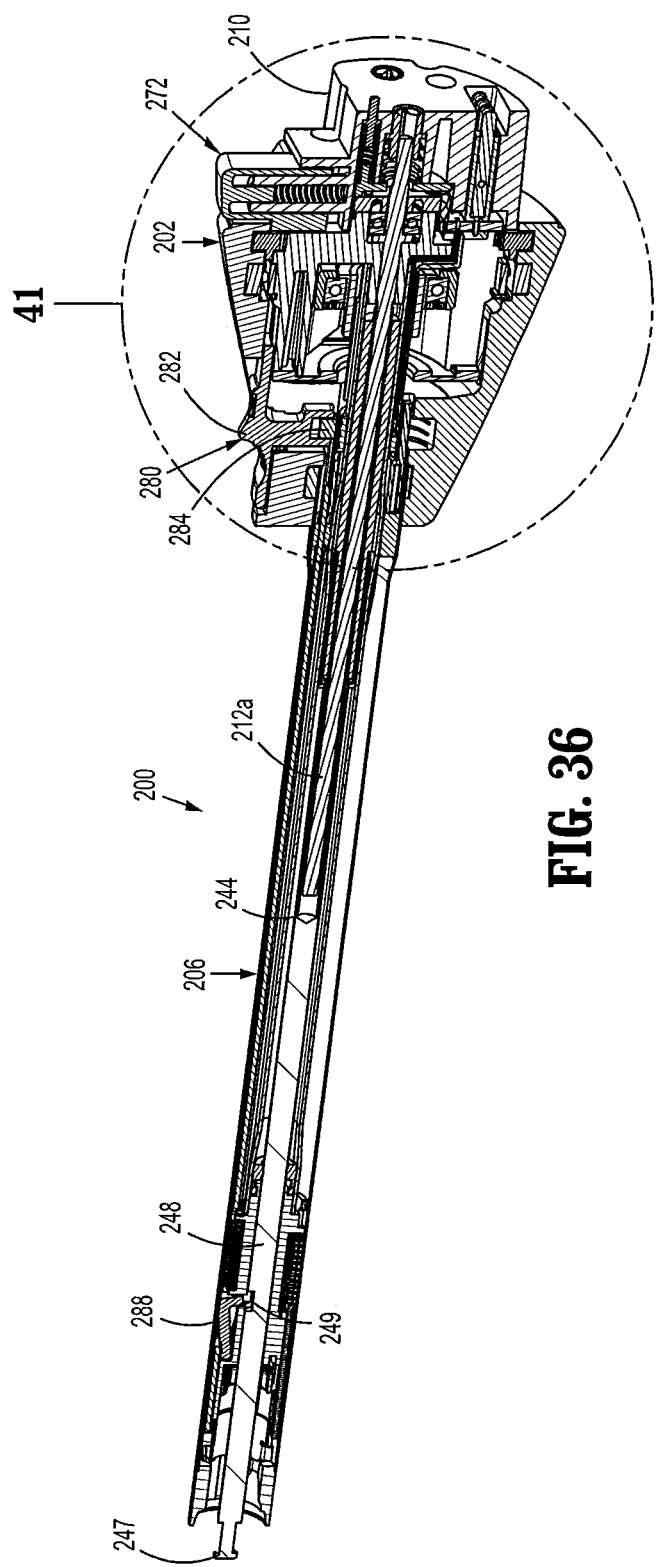
FIG. 36 is a longitudinal, cross-sectional view of the adapter assembly of FIGS. 1 and 20-26.
Figure 37:
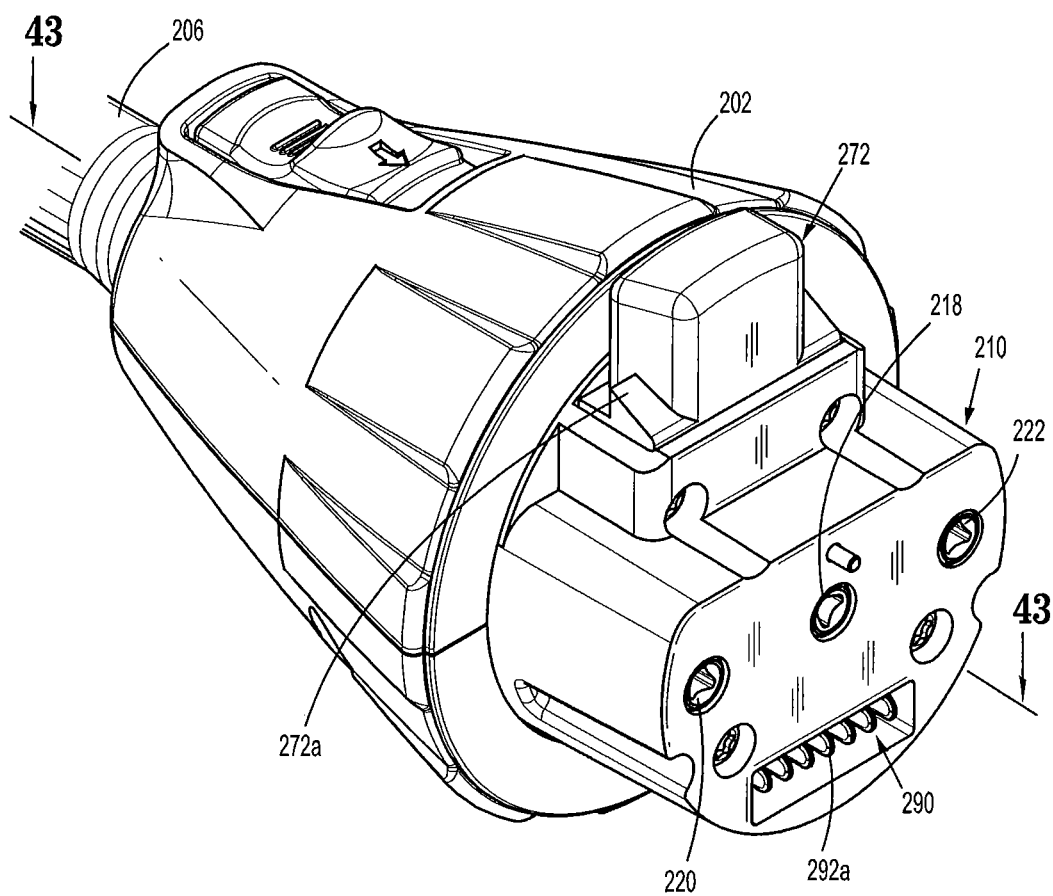
FIG. 37 is an enlarged view of the indicated area of detail of FIG. 21.
Figure 39:
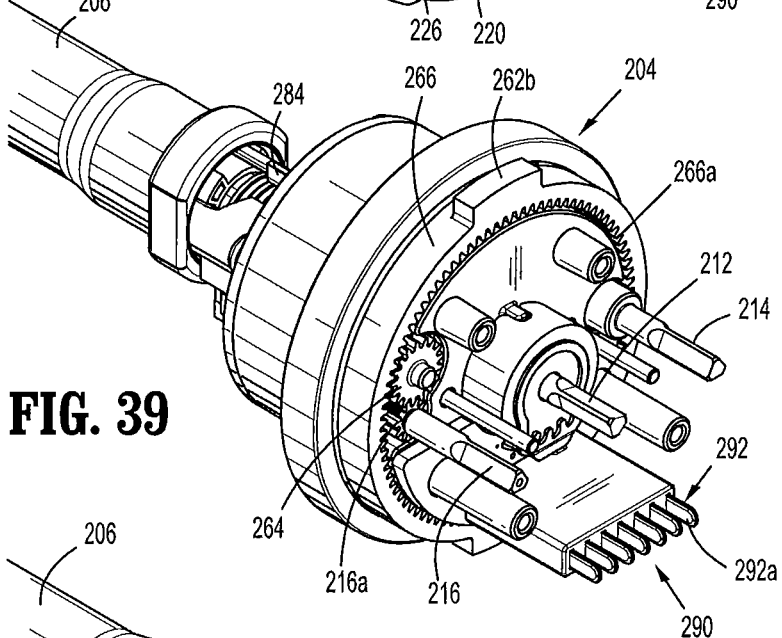
FIG. 39 is a rear, perspective view of the inner housing assembly of the adapter assembly of FIGS. 1 and 20-26, with the outer knob housing, the proximal cap and a bushing plate removed therefrom.
Figure 40:
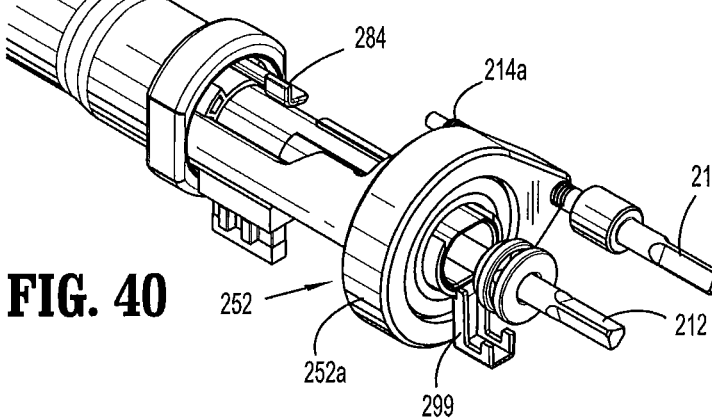
FIG. 40 is a rear, perspective view of the inner housing assembly of the adapter assembly of FIGS. 1 and 20-26, with the outer knob housing, the proximal cap, the bushing plate and an inner housing removed therefrom.
Figure 41:
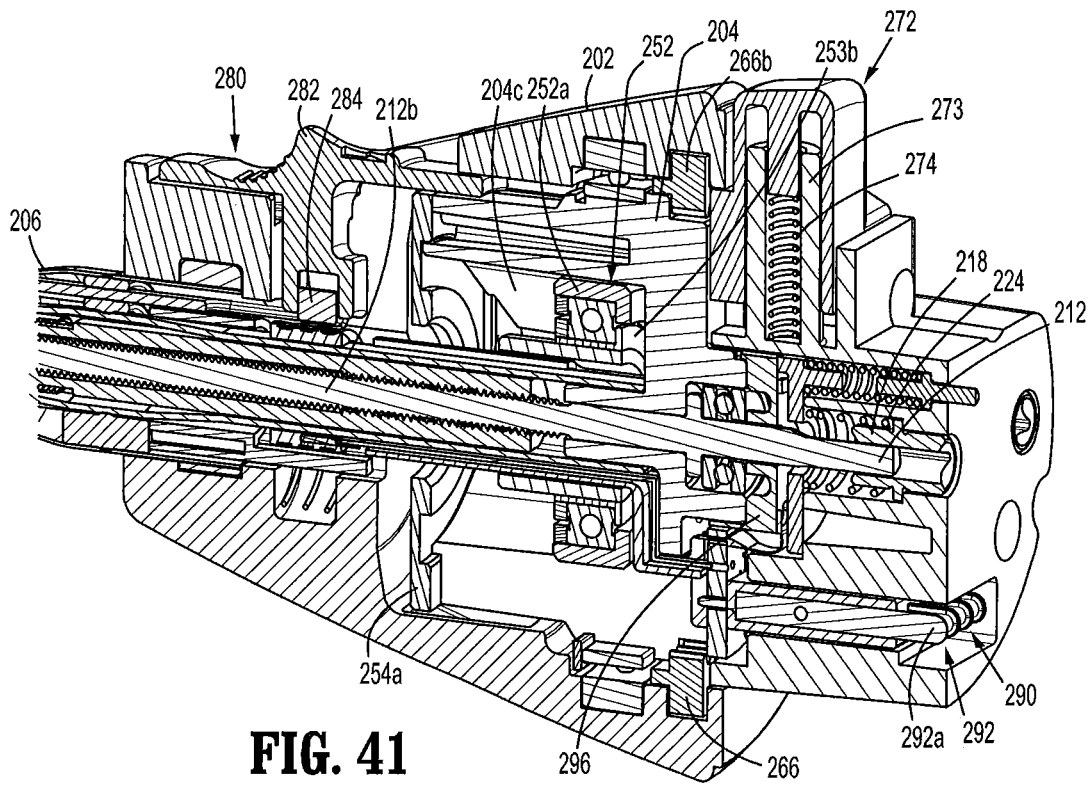
FIG. 41 is an enlarged view of the indicated area of detail of FIG. 36.
Figure 42:
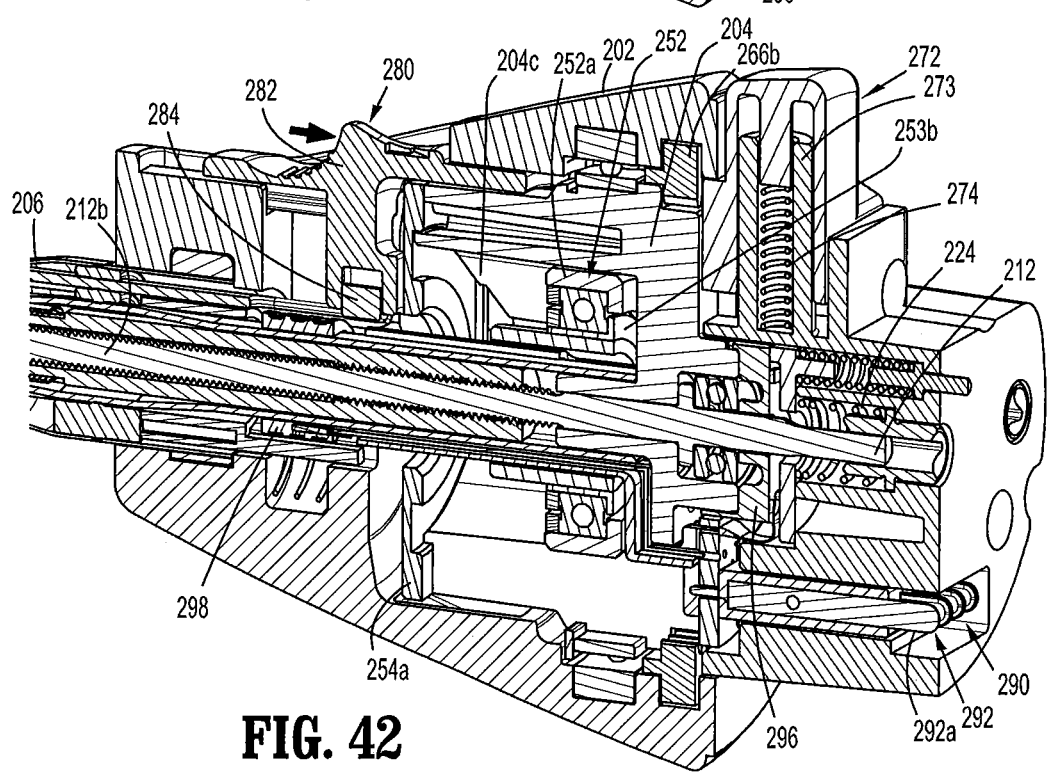
FIG. 42 is an enlarged view of the indicated area of detail of FIG. 36, illustrating a lock button being actuated in a proximal direction.
Figure 43:
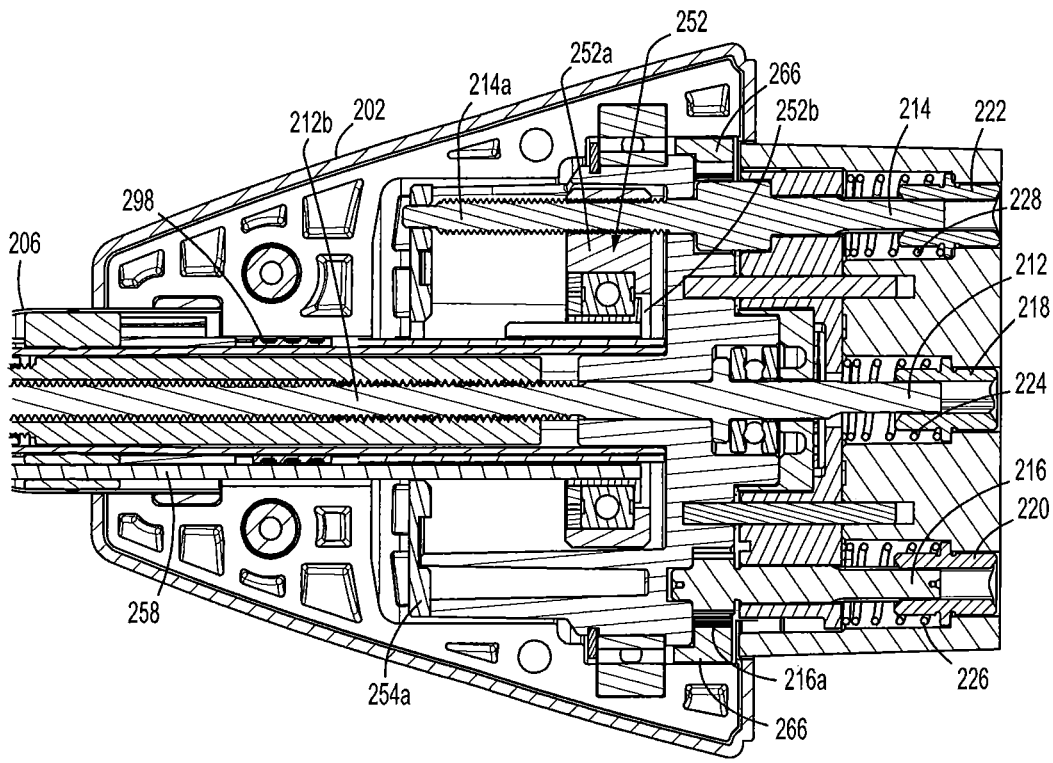
FIG. 43 is a cross-sectional view as taken along section line 43-43 of FIG. 37.
Figure 44:
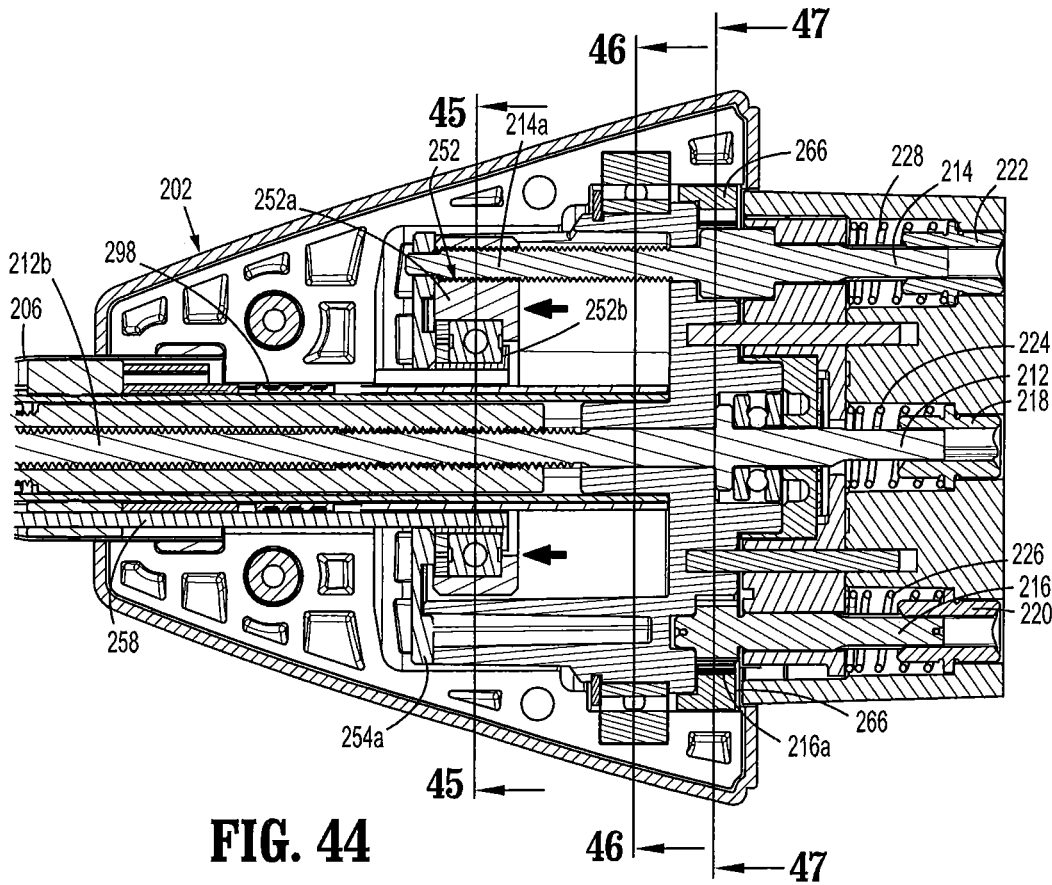
FIG. 44 is a longitudinal, cross-sectional view of the inner and outer knob housing of the adapter assembly, illustrating actuation of the articulation assembly in a distal direction.
Figure 47:
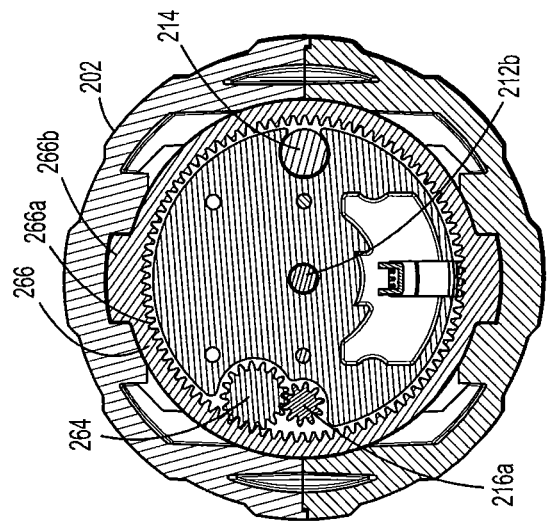
FIG. 47 is a cross-sectional view as taken along section line 47-47 of FIG. 44.
Figure 46:
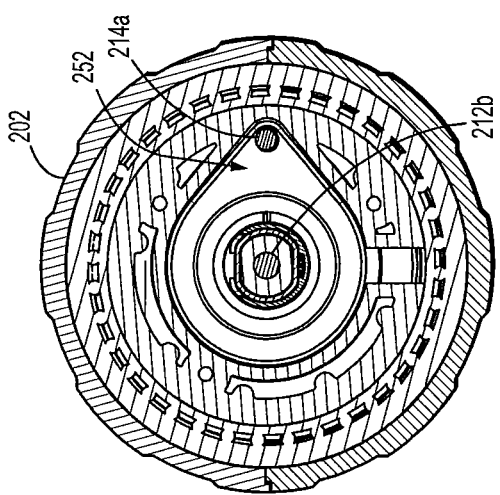
FIG. 46 is a cross-sectional view as taken along section line 46-46 of FIG. 44.
Figure 45:
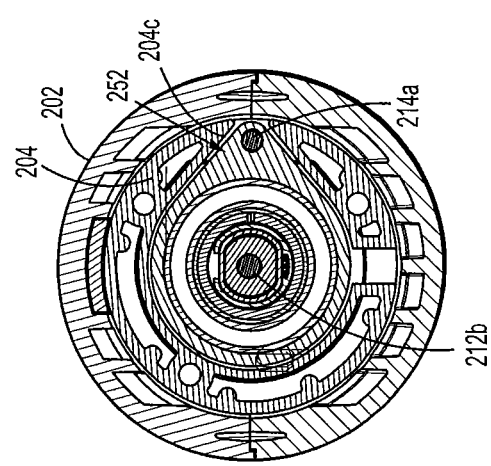
FIG. 45 is a cross-sectional view as taken along section line 45-45 of FIG. 44.

Electrical assembly 290 further includes a strain gauge 296 electrically connected to circuit board 294. Strain gauge 296 is provided with a notch 296a which is configured and adapted to receive stem 204d of hub 204a of inner housing assembly 204. Stem 204d of hub 204a functions to restrict rotational movement of strain gauge 296. As illustrated in FIGS. 32, 35 and 39, first rotatable proximal drive shaft 212 extends through strain gauge 296. Strain gauge 296 provides a closed-loop feedback to a firing/clamping load exhibited by first rotatable proximal drive shaft 212, based upon which power-pack core assembly 106 sets the speed current limit on the appropriate motor 152, 154, 156.

Electrical assembly 290 also includes a slip ring 298 non-rotatably and slidably disposed along drive coupling nut 244 of outer tube 206. Slip ring 298 is in electrical connection with circuit board 294. Slip ring 298 functions to permit rotation of first rotatable proximal drive shaft 212 and axial translation of drive coupling nut 244 while still maintaining electrical contact of electrical contact rings 298a thereof with at least another electrical component within adapter 200, and while permitting the other electrical components to rotate about first rotatable proximal drive shaft 212 and drive coupling nut 244.

Electrical assembly 290 may include a slip ring cannula or sleeve 299 positioned about drive coupling nut 244 to protect and/or shield any wires extending from slip ring 298.

Figure 33:
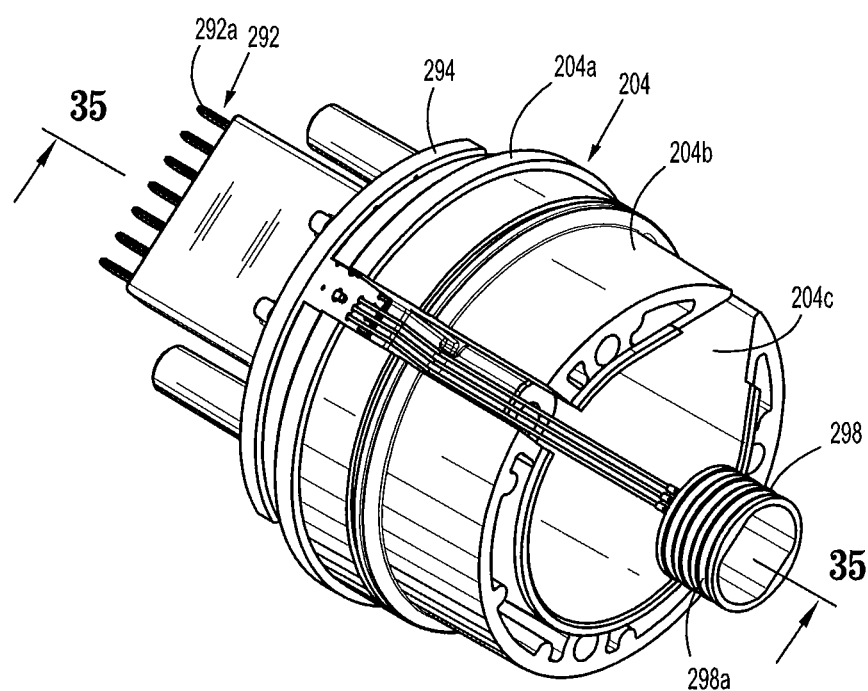
FIG. 33 is a perspective view of the electrical assembly shown supported on a proximal inner housing assembly.
Figure 34:
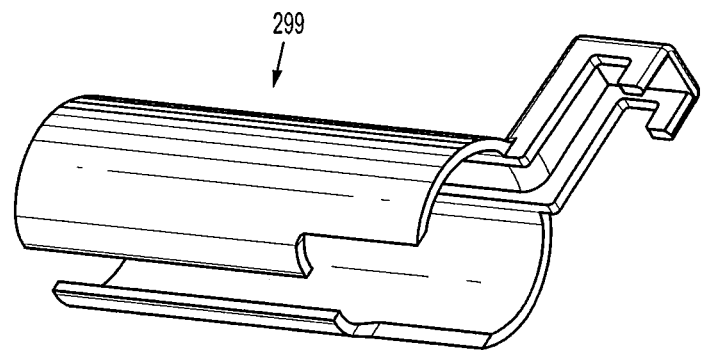
FIG. 34 is a perspective view of a slip ring cannula or sleeve of the adapter assembly of FIGS. 1 and 20-26.

Turning now to FIGS. 26, 33 and 35, inner housing assembly 204 includes a hub 204a having a distally oriented annular wall 204b defining a substantially circular outer profile, and defining a substantially tear-drop shaped inner recess or bore 204c. Bore 204c of hub 204a is shaped and dimensioned to slidably receive articulation bearing assembly 252 therewithin.

Inner housing assembly 204 includes a ring plate 254a (FIG. 26) secured to a distal face of distally oriented annular wall 204b of hub 204a. Plate 254a defines an aperture 254e therethrough that is sized and formed therein so as to be aligned with second proximal drive shaft 214 and to rotatably receive a distal tip 214c of second proximal drive shaft 214. In this manner, distal tip 214c of second proximal drive shaft 214 is supported and prevented from moving radially away from a longitudinal rotational axis of second proximal drive shaft 214 as second proximal drive shaft 214 is rotated to axially translate articulation bearing assembly 252.

As illustrated in FIG. 35, hub 204a defines a feature (e.g., a stem or the like) 204d projecting therefrom which functions to engage notch 296a of strain gauge 296 of electrical assembly 290 to measure forces experienced by shaft 212 as surgical device 100 is operated.

Figure 38:
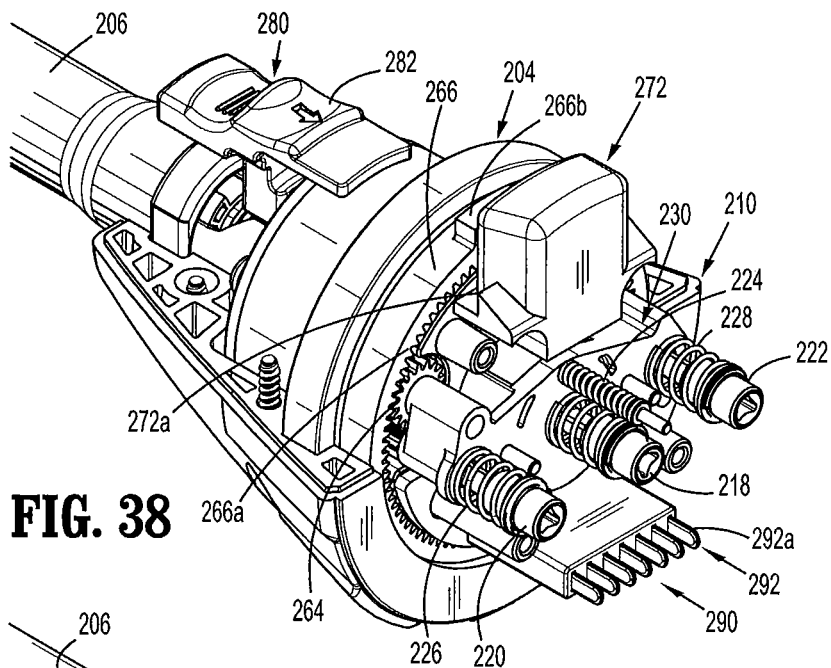
FIG. 38 is a rear, perspective view of the inner housing assembly of the adapter assembly of FIGS. 1 and 20-26, with an outer knob housing half-section and a proximal cap removed therefrom.

With reference to FIGS. 26 and 38, a plate bushing 230 of inner housing assembly 204 is shown and described. Plate bushing 230 extends across hub 204a of inner housing assembly 204 and is secured to hub 204a by fastening members. Plate bushing 230 defines three apertures 230a, 230b, 230c that are aligned with and rotatably receive respective first, second and third proximal drive shafts 212, 214, 216 therein. Plate bushing 230 provides a surface against which first, second and third biasing members 224, 226 and 228 come into contact or rest against.

With reference to FIGS. 48-52, adapter 200 includes a distal cap 208 extending distally from distal portion 206b of outer tube 206. Adapter 200 further includes a switch 320, a sensor link or switch actuator 340, an annular member 360, and actuation bar 284, each being disposed within outer tube 206. Switch 320 is configured to toggle in response to a coupling of SULU 400 to distal portion 206b of outer tube 206. Switch 320 is configured to couple to a memory 432 of SULU 400. The memory 423 of SULU 400 is configured to store data pertaining to SULU 400 and is configured to provide the data to controller circuit board 142 of surgical device 100 in response to SULU 400 being coupled to distal portion 206b of outer tube 206, as detailed below with reference to FIGS. 70-82. Switch 320 is disposed within distal portion 206b of outer tube 206 and is oriented in a proximal direction. Switch 320 is mounted on a printed circuit board 322 that is electrically connected with controller circuit board 142 of power-pack 101. As detailed below, power-pack core assembly 106 monitors the 1-wire communication bus between power-pack core assembly 106 and adapter 200 and is able to detect that SULU 400 is engaged to distal portion 206b of outer tube 206 or that SULU 400 is disengaged from distal portion 206b of outer tube 206 by recognizing that switch 230 has been toggled.

Figure 48:
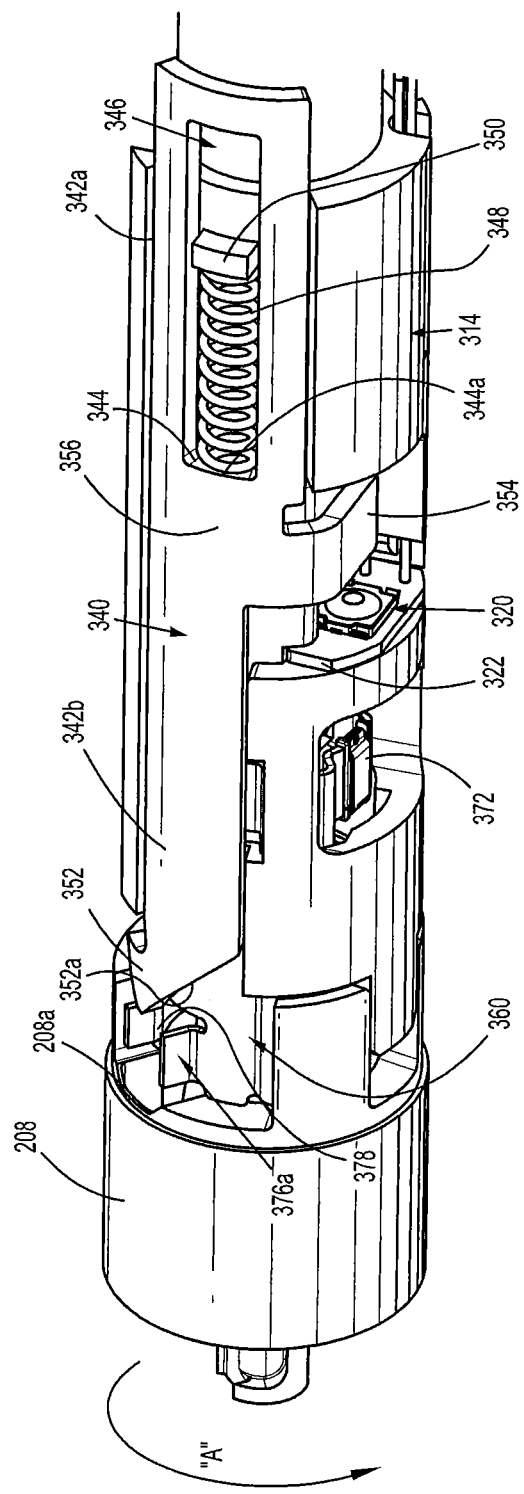
FIG. 48 is a cutaway view of a distal portion of the adapter assembly shown of FIGS. 1 and 20-26, without a loading unit engaged therewith.
Figure 49:
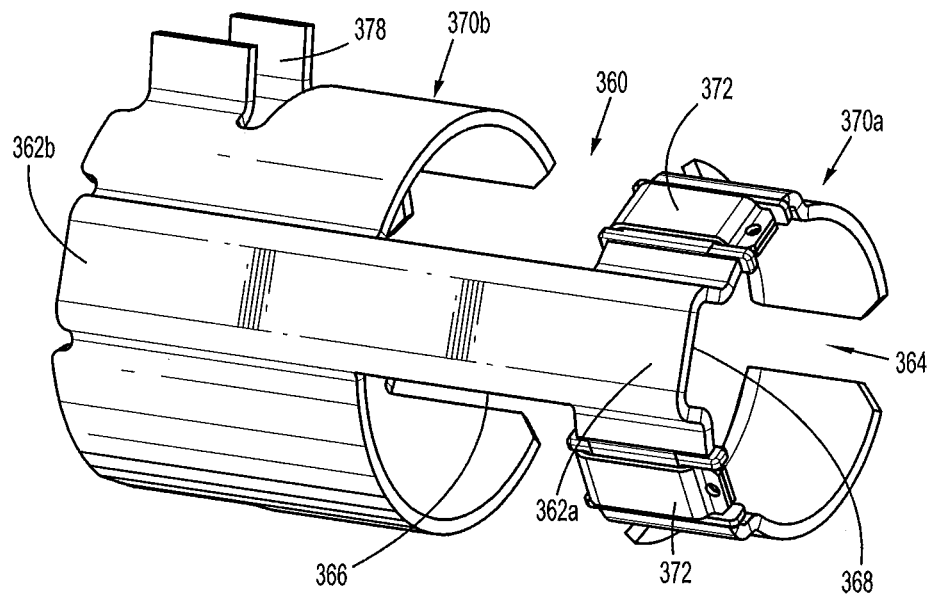
FIG. 49 is a perspective view of an annular member of the adapter assembly of FIGS. 1 and 20-26.
Figure 50:
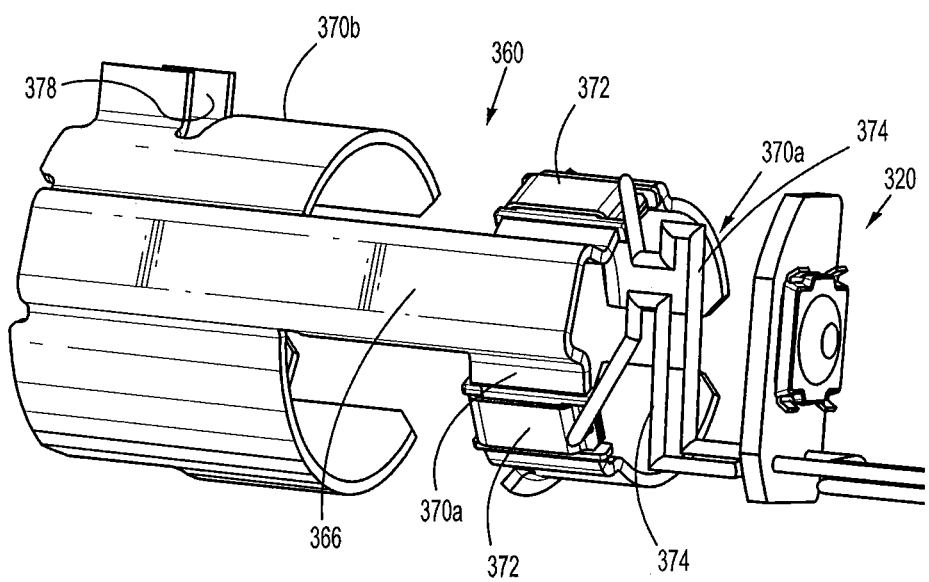
FIG. 50 is a perspective view of the annular member shown in FIG. 49 electrically connected to a switch of the adapter assembly of FIGS. 1 and 20-26.
Figure 51:
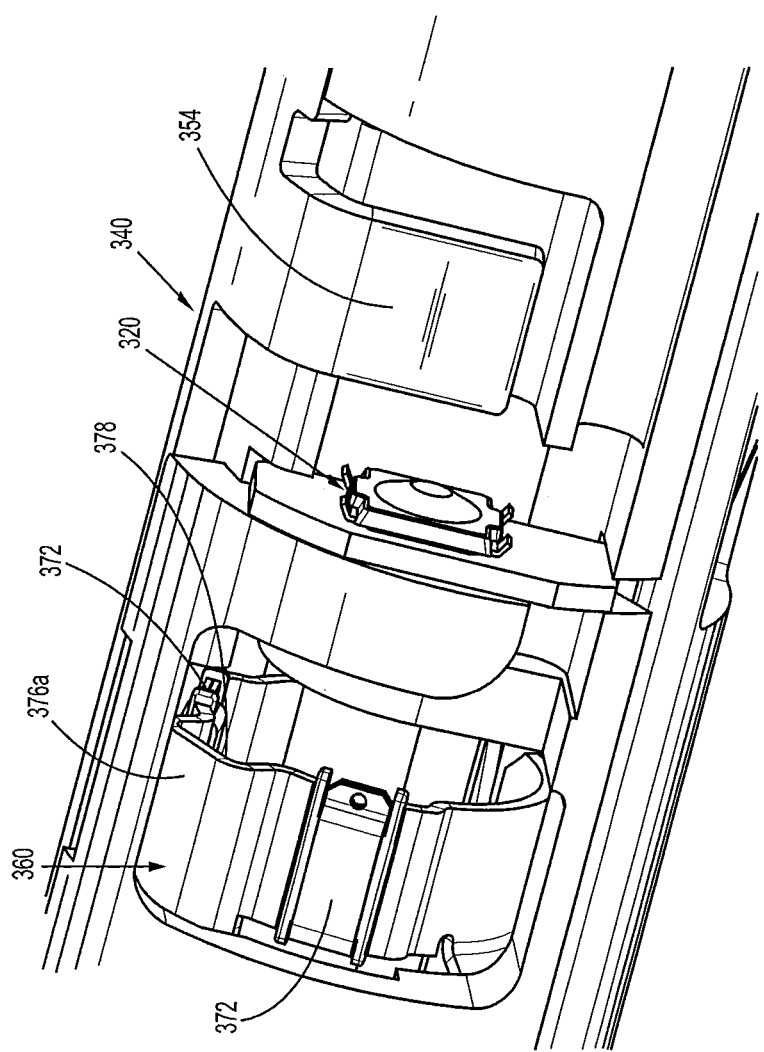
FIG. 51 is an enlarged view of the distal portion of the adapter assembly of FIGS. 1 and 20-26, including the annular member and the switch assembled therein.

Adapter 200 includes, as illustrated in FIGS. 48 and 51, a switch actuator 340 slidably disposed within distal portion 206b of outer tube 206. Switch actuator 340 is longitudinally movable between a proximal position, as shown in FIGS. 48 and 51, and a distal position, as shown in FIG. 63. The switch actuator 340 toggles switch 320 during movement between proximal and distal positions.

Switch actuator 340 has a proximal end portion 342a and a distal end portion 342b. Proximal end portion 342a of switch actuator 340 includes an inner surface 344 that defines an elongated opening 346 having a coil spring 348 disposed therein. Coil spring 348 is secured within opening 346 between a distal end 344a of inner surface 344 and a projection 350 of inner housing 314, which projects through opening 346.

Distal end portion 342b of switch actuator 340 includes an extension 352 having a tapered portion 352a. Extension 352 is engaged to a first surface feature 376a of annular member 360 when annular member 360 is in a selected orientation relative to extension 352, such that switch actuator 340 is maintained in the proximal position. Switch actuator 340 further includes a tab 354 extending from an intermediate portion 356 thereof. Coil spring 348 resiliently biases switch actuator 340 toward the distal position, as shown in FIGS. 48, 61 and 63, in which tab 354 actuates or depresses switch 320.

With reference to FIGS. 48-52, adapter 200 includes an annular member 360, which is rotatably disposed within inner housing 314 of outer tube 206. Annular member 360 extends from a proximal end 362a to a distal end 362b and defines a cylindrical passageway 364 therethrough configured for disposal of an inner housing 410b of SULU 400, as described in greater detail below. Annular member 360 includes a longitudinal bar 366 defining an elongated slot 368 along a length thereof configured for sliding disposal of a fin 420 of inner housing 410b (FIG. 66-68) of SULU 400. Proximal end 362a includes a first ring 370a and distal end 362b includes a second ring 370b, spaced from first ring 370a along longitudinal bar 366. First ring 370a includes a pair of electrical contacts 372 electrically coupled to switch 320 via wires 374. Electrical contacts 372 are configured to engage corresponding electrical contacts 430 of SULU 400, such that switch 320 and annular member 360 are capable of transferring data pertaining to SULU 400 therebetween, ultimately for communication with power-pack core assembly 106, as described in greater detail below. It is contemplated that a portion of annular member 360 is ring-shaped.

Figure 52:
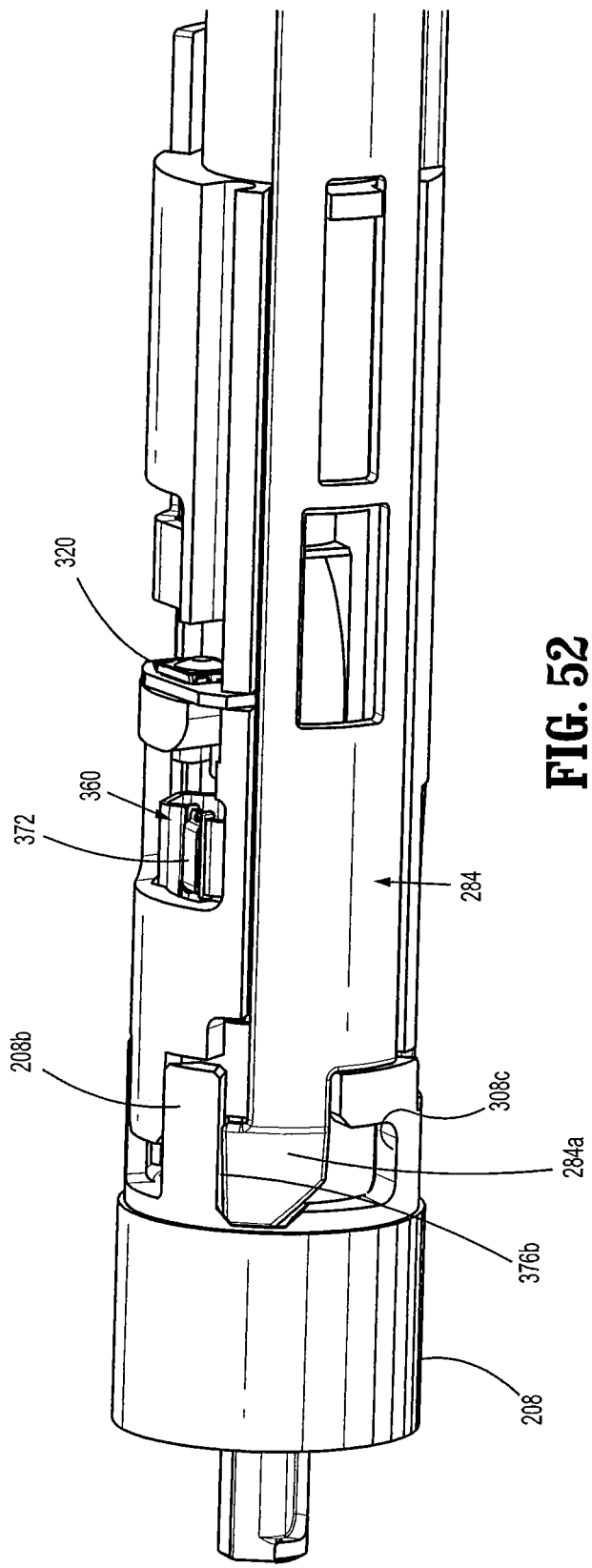
FIG. 52 is another cutaway view of the distal portion of the adapter assembly of FIGS. 1 and 20-26, without a loading unit engaged therewith.
Figure 53:
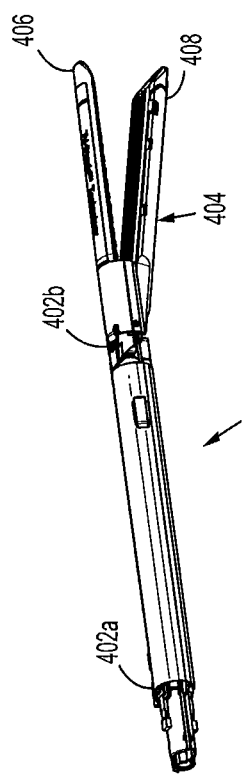
FIG. 53 is a perspective view of the loading unit of FIG. 1.

With specific reference to FIGS. 51 and 52, annular member 360 also includes a first surface feature 376a, and a second surface feature or tab 376b, each extending from second ring 370b. Surface feature 376a of annular member 360 is configured to interface with a first surface feature or first lug 412a (FIGS. 61-64) of SULU 400, such that annular member 360 is rotatable by and with SULU 400. Specifically, surface feature 376a defines a cavity 378 therein having a squared configuration configured for mating engagement with correspondingly shaped first lug 412a of SULU 400. Cavity 378 is shaped and dimensioned to capture first lug 412a (FIGS. 57 and 58) of SULU 400 upon insertion of SULU 400 into adapter 200, such that annular member 360 is rotatable with and by SULU 400. Surface feature 376a of annular member 360 is also configured to abut extension 352 of switch actuator 340 to maintain switch actuator 340 in the proximal position.

Annular member 360 is rotatable between a first orientation and a second orientation. In the first orientation, as shown in FIGS. 51 and 52, surface feature 376a of annular member 360 is captured between a proximal lip 208a of distal cap 208 and extension 352 of switch actuator 340. In this configuration, the surface feature 376a prevents distal movement of switch actuator 340 from the proximal position to the distal position, thereby maintaining tab 354 of switch actuator 340 out of engagement with switch 320. Accordingly, surface feature 376a of annular member 360 has a dual function for both maintaining switch actuator 340 in the proximal position, out of engagement with switch 320, and capturing first lug 412a of SULU 400 in cavity 378 to provide an interface between SULU 400 and annular member 360.

In use, SULU 400 is inserted within the distal end of outer tube 206 of adapter 200 to mate first lug 412a of SULU 400 with first surface feature 376a of annular member 360, as shown in FIG. 61. SULU 400 is rotated, in a direction indicated by arrow "C" (FIG. 63), to drive a rotation of annular member 360 from the first orientation to the second orientation. Rotation of annular member 360 from the first orientation to the second orientation disengages surface feature 376a of annular member 360 from extension 352 of switch actuator 340 such that coil spring 348 of switch actuator 340 biases switch actuator 340 toward the distal position, in which switch 320 is toggled, as shown in FIG. 63.

With continued reference to FIG. 52, annular member 360 further includes a projection or tab 376b extending from second ring 370b. Tab 376b has a planar configuration and is configured to resist and/or prevent inadvertent rotation of annular member 360 within inner housing 314 when SULU 400 is not engaged to adapter 200. With specific reference to FIG. 52, when annular member 360 is in the first orientation, tab 376b is secured between a projection 208b of distal cap 208 and a distal end 284a of actuation bar 284. Rotation of annular member 360 from the first orientation to the second orientation is resisted and/or prevented until actuation bar 284 is moved to a second configuration, as described below. In this way, tab 376b ensures that first surface feature 376a of annular member 360 is maintained in abutment with extension 352 of switch actuator 340 thereby maintaining switch actuator 340 in the proximal position until SULU 400 is engaged to adapter 200.

With reference to FIGS. 52, 62 and 64, and as discussed briefly above, adapter 200 further includes a lock mechanism 280 having a button 282 slidably supported on outer knob housing 202, and an actuation bar 284 extending from button 282. Actuation bar 284 extends longitudinally through outer tube 206. Specifically, actuation bar 284 is slidingly disposed within or along inner housing 314 of adapter 200 and is resiliently biased toward a first configuration, as shown in FIG. 64. In the first configuration, a distal end or extension 284a of actuation bar 284 is engaged with distal cap 208. Extension 284a of actuation bar 284 is configured for engagement with a second lug 412b (FIG. 64) of SULU 400 upon insertion and rotation of SULU 400 into adapter 200. As shown in FIG. 62, SULU 400 engages adapter 200 and actuation bar 284 in the first configuration, second lug 412b of SULU 400 is captured in an enclosure 286 defined by extension 284a of actuation bar 284 and distal cap 208.

As illustrated in FIGS. 1 and 54-56, SULU is designated as 400. SULU 400 includes a proximal body portion 402 and a tool assembly 404. Proximal body portion 402 is releasably attached to a distal cap 208 of adapter 200 and tool assembly 404 is pivotally attached to a distal end of proximal body portion 402. Tool assembly 404 includes an anvil assembly 406 and a cartridge assembly 408. Cartridge assembly 408 is pivotal in relation to anvil assembly 406 and is movable between an open or unclamped position and a closed or clamped position for insertion through a cannula of a trocar. Proximal body portion 402 includes at least a drive assembly 460 and an articulation link 466.

Referring to FIG. 54, drive assembly 460 includes a flexible drive beam 464 having a distal end and a proximal engagement section. A proximal end of the engagement section includes diametrically opposed inwardly extending fingers that engage a hollow drive member 474 to fixedly secure drive member 474 to the proximal end of beam 464. Drive member 474 defines a proximal porthole which receives connection member 247 of drive tube 246 of first drive converter assembly 240 of adapter 200 when SULU 400 is attached to distal cap 208 of adapter 200.

Proximal body portion 402 of SULU 400 includes an articulation link 466 having a hooked proximal end which extends from a proximal end of SULU 400.

As illustrated in FIG. 54, cartridge assembly 408 of tool assembly 404 includes a staple cartridge removably supported in a carrier. The staple cartridge defines a central longitudinal slot, and three linear rows of staple retention slots positioned on each side of the longitudinal slot. Each of the staple retention slots receives a single staple and a portion of a staple pusher. During operation of surgical device 100, drive assembly 460 abuts an actuation sled and pushes actuation sled through the cartridge. As the actuation sled moves through the cartridge, cam wedges of the actuation sled sequentially engage the staple pushers to move the staple pushers vertically within the staple retention slots and sequentially ejects a single staple therefrom for formation against an anvil plate of anvil assembly 406.

To fully disengage SULU 400 from adapter 200, SULU 400 is axially translated, in a distal direction, through distal cap 208, and out of outer tube 206 of adapter 200. It is contemplated that upon surgical device 100 detecting that SULU 400 is not engaged to adapter 200, power may be cut off from adapter 200, and alarm (e.g., audio and/or visual indication) may be issued, and combinations thereof, as detailed below.

With reference to FIGS. 54-60, SULU 400 further includes an outer housing 410a and an inner housing 410b disposed within outer housing 410b. First and second lugs 412a, 412b are each disposed on an outer surface of a proximal end 414 of outer housing 410a. First lug 412a has a substantially rectangular cross-section corresponding to cavity 378 of surface feature 376a of annular member 360 of adapter 200. Second lug 412b has a substantially rectangular cross-section corresponding to inner groove 208c of distal cap 208 of adapter 200. Proximal end 414 of outer housing 410a is sized and dimensioned to be inserted through distal cap 208 to engage adapter 200.

Outer housing 410a defines a first notch 416a and a second notch 416b in a proximal-most edge thereof. First notch 416a is configured for sliding receipt of a tapered fin 420 extending from inner housing 410b. At least a portion of fin 420 is configured for disposal in slot 468 defined in longitudinal bar 366 of annular member 360 to facilitate insertion of inner housing 410b into annular member 360. Second notch 416b is configured for a snap fit engagement with a pair of parallel, resilient fingers 422 of inner housing 410b. Second notch 416b generally has a rectangular configuration with a pair of grooves 418 defined therein. Each finger 422 has a mating part 424 configured for mating engagement with one respective groove 418 of second notch 416b. Outer housing 410a further defines a pair of channels 426 defined in an interior surface 428 thereof and disposed on either side of first notch 416a. Each channel 426 of outer housing 410a is configured for disposal of a portion of an electrical contact 430 of inner housing 410b, as described in greater detail below.

In use, fin 420 and fingers 422 of inner housing 410b are aligned with first and second notches 416a, 416b of outer housing 410a, respectively, and inner housing 410b is axially translated within outer housing 410a, until mating parts 424 of fingers 422 are captured in grooves 418 of second notch 416b to capture inner housing 410b within outer housing 410a.

SULU 400 further includes a memory 432 disposed within or on inner housing 410b. Memory 432 includes a memory chip 434 and a pair of electrical contacts 430 electrically connected to memory chip 434. Memory chip 434 is configured to store one or more parameters relating to SULU 400. The parameter includes a serial number of a loading unit, a type of loading unit, a size of loading unit, a staple size, information identifying whether the loading unit has been fired, a length of a loading unit, maximum number of uses of a loading unit, and combinations thereof. Memory chip 434 is configured to communicate to surgical device 100 a presence of SULU 400 and one or more of the parameters of SULU 400 via electrical contacts 430, upon engagement of SULU 400 with adapter 200, as detailed below.

Figure 57:
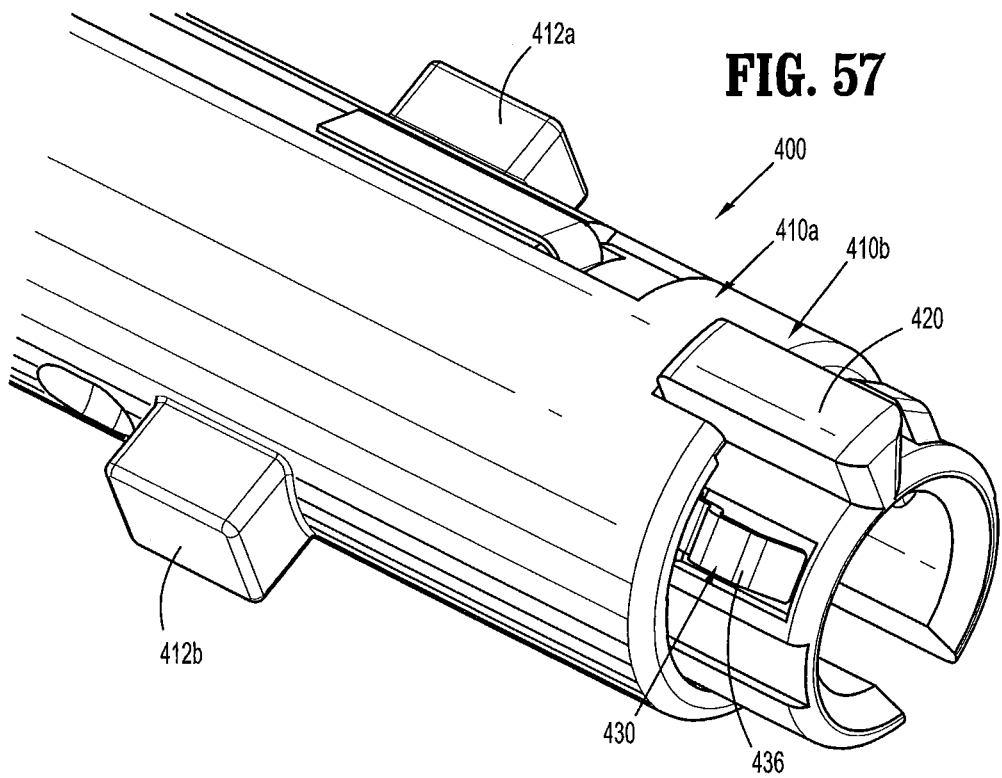
FIGS. 57 and 58 are alternate cutaway views of the loading unit shown in FIGS. 1 and 53-54, with the inner and outer housings assembled.
Figure 58:
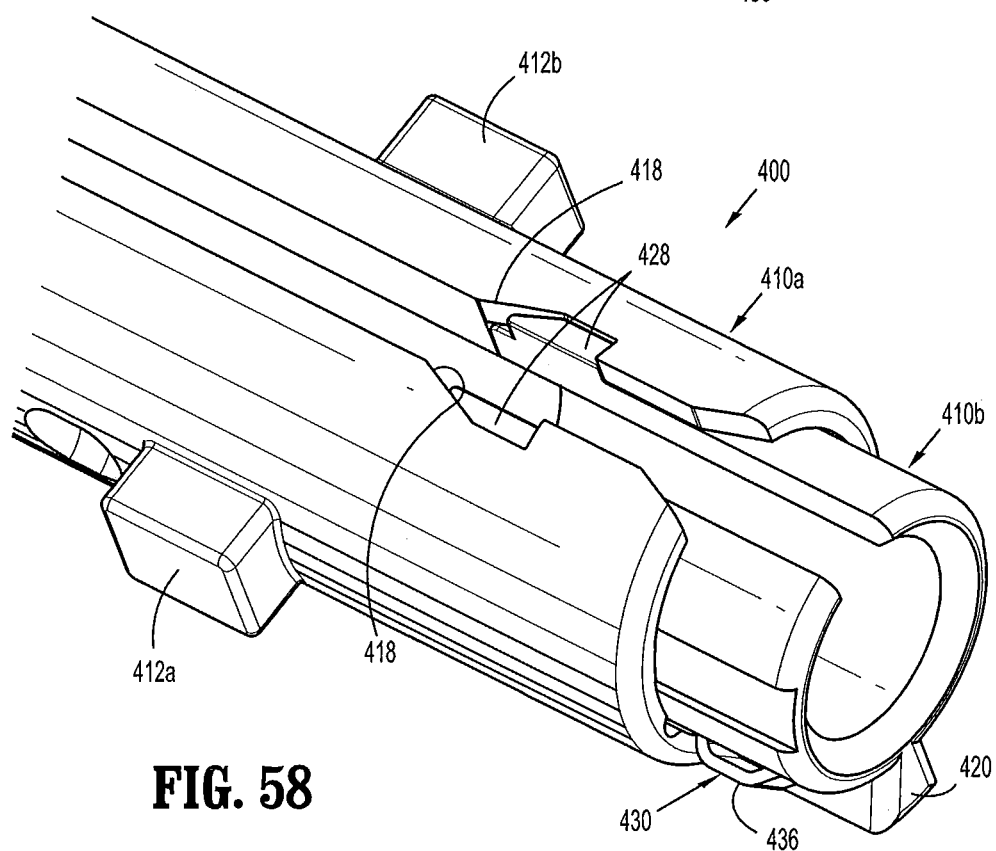
Figure 59:
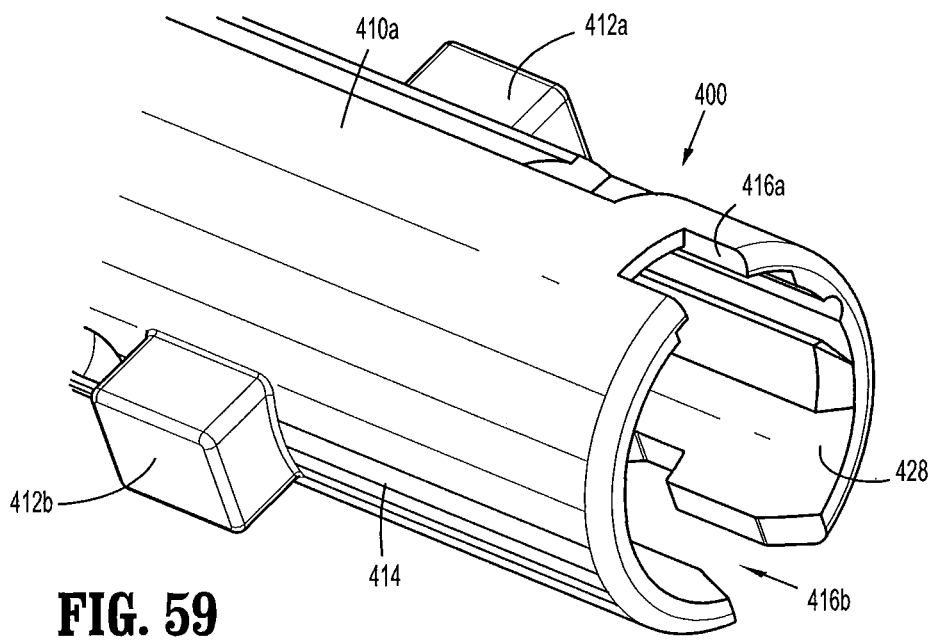
FIGS. 59 and 60 are alternate cutaway views of an outer housing of the loading unit shown in FIGS. 1 and 53-54.
Figure 60:
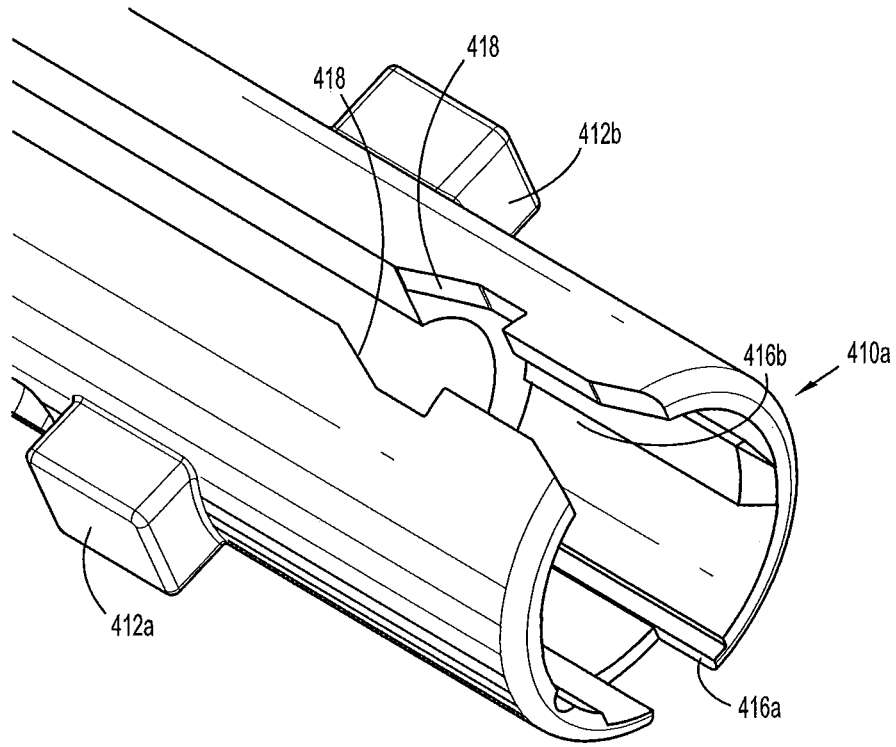
Figure 65:
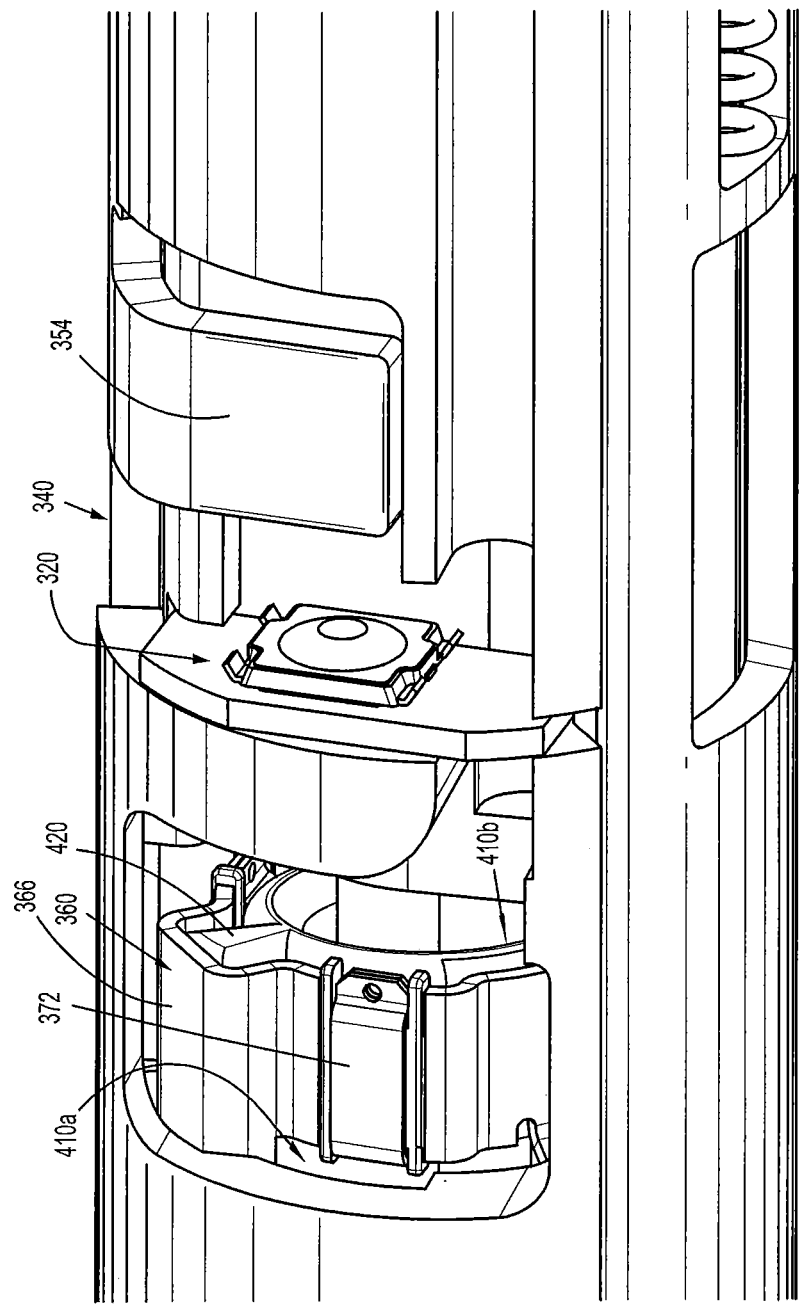
FIG. 65 is an enlarged cutaway view of the distal portion of the adapter assembly of FIGS. 1 and 20-26.
Figure 70:
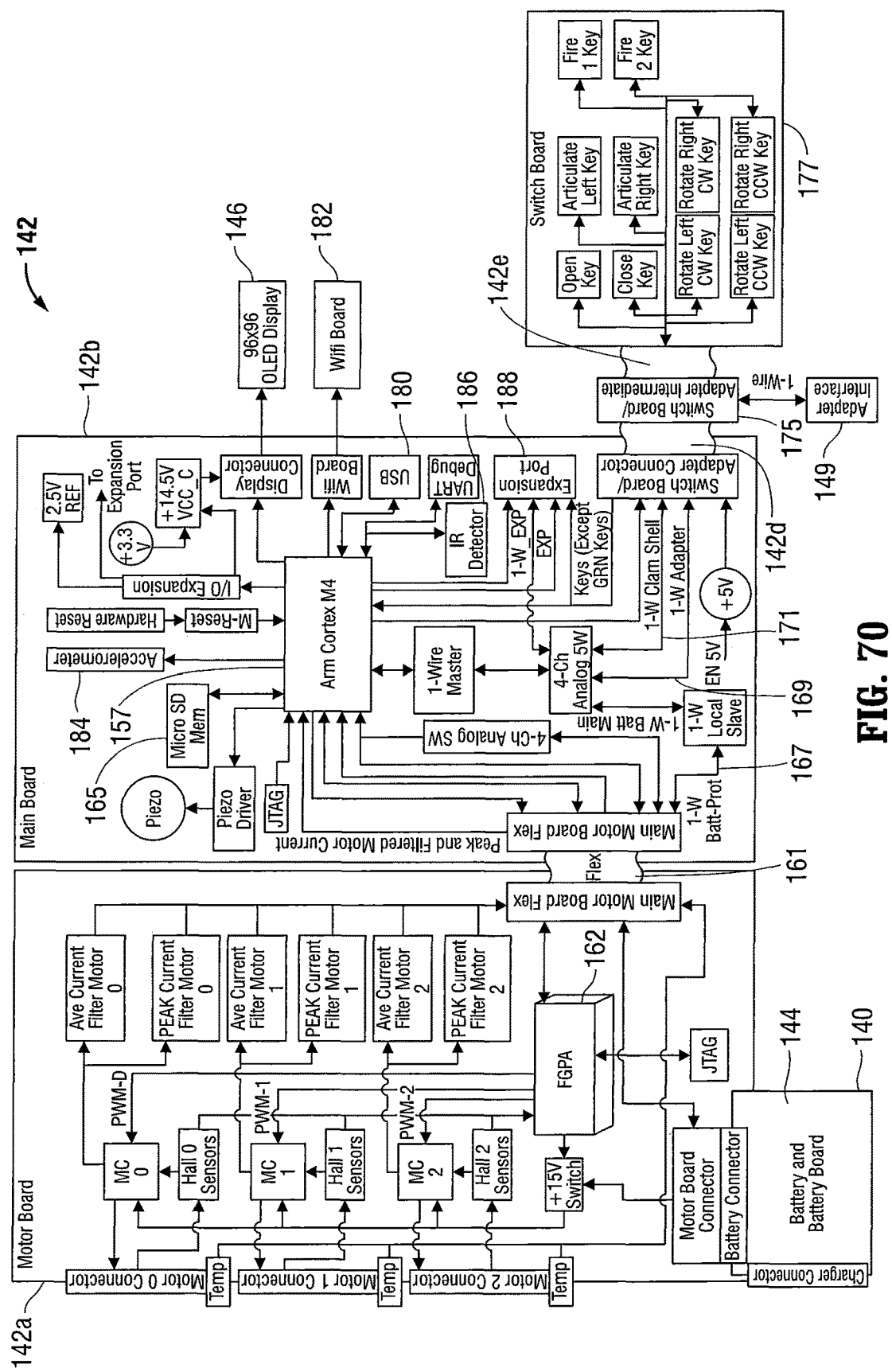
FIG. 70 is a schematic diagram of the circuit board of the power-pack of the handheld surgical device of FIG. 1.

Electrical contacts 430 are disposed on an outer surface of inner housing 410b and are configured to engage electrical contacts 372 of annular member 360 upon insertion of SULU 400 into adapter 200. A proximal end of each electrical contact 430 has a bent portion 436 extending beyond a proximal-most edge of outer housing 410a of SULU 400 when inner housing 410b is secured within outer housing 410a, as shown in FIGS. 57 and 58. Bent portions 436 of electrical contacts 430 of SULU 400 engage electrical contacts 372 of annular member 360 upon insertion of SULU 400 within annular member 360 of adapter 200. This connection between the contacts 372 and 430 allows for communication between memory chip 434 of SULU 400 and controller circuit board 142 of surgical device 100. In particular, controller circuit board 142 of surgical device 100 receives one or more parameters pertaining to SULU 400 and that SULU 400 is engaged to adapter 200.

In operation, SULU 400 is inserted into distal end 206b of outer tube 206 of adapter 200 to matingly engage first lug 412a of SULU 400 within cavity 378 of surface feature 376a of annular member 360, as shown in FIGS. 61-65. The insertion of SULU 400 within adapter 200 also engages second lug 412b with extension 284a of actuation bar 284 to move actuation bar 284 in a proximal direction, as shown in the direction indicated by arrow "B" in FIG. 62, to the second configuration, and out of abutment with tab 376b of annular member 360. In this way, extension 284a of actuation bar 284 no longer prevents annular member 360 from rotating. With SULU 400 in this initial insertion position within adapter 200, switch actuator 340 remains in the proximal position out of engagement with switch 320.

To engage SULU 400 with adapter 200, SULU 400 is rotated, in a direction indicated by arrow "C" in FIG. 63, to drive a rotation of annular member 360, via the mating engagement between first lug 412a of SULU 400 and surface feature 376a of annular member 360, from the first orientation to the second orientation. The rotation of annular member 360 from the first orientation to the second orientation displaces surface feature 376a of annular member 360 away from extension 352 of switch actuator 340. With surface feature 376a out of engagement with extension 352 of switch actuator 340, switch actuator 340 moves from the proximal position, as shown in FIGS. 48 and 51, to the distal position, as shown in FIG. 63, via coil spring 348. As switch actuator 340 moves to the distal position, tab 354 of switch actuator 340 toggles switch 320, e.g., by depressing switch 320, as shown in FIG. 63. Depressing or actuating switch 320 communicates to surgical device 100 that SULU 400 is engaged with adapter 200 and is ready for operation.

The rotation of SULU 400 also moves second lug 412b of SULU 400 into an inner groove 208c defined in distal cap 208 of adapter 200 and out of engagement with extension 284a of actuation bar 284. The resilient bias of actuation bar 284 drives an axial translation of actuation bar 284, in a direction indicated by arrow "D" in FIG. 64, to dispose actuation bar 284 into the first configuration. With actuation bar 284 in the first configuration, second lug 412b of SULU 400 is captured within enclosure 286 defined by extension 284a of actuation bar 284 and inner groove 208c of distal cap 208 of adapter 200. SULU 400 is prevented from moving distally out of enclosure 286 due to an inner ledge 208d of inner groove 208c of distal cap 208 of adapter 200, and is prevented from rotating, in a direction indicated by arrow "E" shown in FIG. 64, due to extension 284a of actuation bar 284. Therefore, SULU 400 is releasably, engaged to adapter 200.

To selectively release SULU 400 from adapter 200, a practitioner translates or pulls actuation bar 284 in a proximal direction, such that extension 284a of actuation bar 284 is no longer blocking second lug 412b of SULU 400 and SULU 400 can be rotated. SULU 400 is rotated, in a direction indicated by arrow "F" in FIG. 63, to move second lug 412b of SULU 400 out of abutment with inner ledge 208d of distal cap 208. The rotation of SULU 400 also drives the rotation of annular member 360 from the second orientation to the first orientation via the mating engagement of first lug 412a of SULU 400 and surface feature 376a of annular member 360. As annular member 360 rotates, surface feature 376a rides along tapered portion 352a of extension 352 of switch actuator 340 to drive switch actuator 340 in a proximal direction until annular member 360 is in the first orientation and switch actuator 340 is in the proximal position, out of engagement with switch 320. Upon tab 354 of switch actuator 340 disengaging switch 320, switch 320 is toggled, which communicates to surgical device 100 that SULU 400 may be pulled out of adapter 200.

In operation, SULU 400, with inner housing 410b disposed within outer housing 410a, is manipulated to align fin 420 of inner housing 410b and electrical contacts 430 of inner housing 410b with longitudinal bar 366 of annular member 360 and electrical contacts 372 of annular member 360, respectively. SULU 400 is inserted within the distal end of adapter 200 thereby engaging first lug 412a of outer housing 410a within surface feature 376a of annular member 360 and forming a wiping contact between electrical contacts 430 of inner housing 410b and electrical contacts 372 of annular member 360, as shown in FIGS. 63 and 64.

As described above with reference to FIGS. 61 and 62, upon the initial insertion of SULU 400 into adapter 200, switch actuator 340 remains disengaged from switch 320. With switch 320 in the unactuated state, there is no electrical connection established between memory chip 434 of SULU 400 and controller circuit board 142 of surgical device 100. As discussed above, upon a rotation of SULU 400, SULU 400 engages adapter 200 and switch actuator 340 toggles switch 320 to actuate switch 320. With switch 320 in the actuated state, an electrical connection is established between memory chip 434 and controller circuit board 142 of surgical device 100, through which information about SULU 400 is communicated to controller circuit board 142 of surgical device 100. Upon both the actuation of switch 320 and the establishment of a wiping contact between electrical contacts 430 of inner housing 410b and electrical contacts 372 of annular member 360, surgical device 100 is able to detect that SULU 400 has been engaged to adapter 200 and to identify one or more parameters of SULU 400.

Referring to FIGS. 53 and 69A-69D, SULU 400, as detailed above, is a single-use, EGIA-type loading unit. However, as noted above, other types of loading units are also capable of being used with surgical device 100 including EEA loading unit 900A, MULU 900B, transverse loading unit 900C, and curved loading unit 900D. As detailed below, the particular loading unit utilized is recognized by power-pack core assembly 106 to enable appropriate operation thereof.

With reference to FIG. 69A, EEA loading unit 900A includes a proximal body portion 902A and tool assembly 904A for circular stapling and cutting, e.g., during the course of an end-to-end anastomosis procedure. Similar to SULU 400 (FIG. 53), EEA loading unit 900A includes an internal memory chip that includes a memory configured to store data pertaining to loading unit 900A. Generally, loading unit 900A is operated when attached to adapter 200 (FIG. 20) in a similar manner as described above with regard to SULU 400 (FIG. 53).

With reference to FIGS. 69B1 and 69B2, MULU 900B is similar to SULU 400 (FIG. 53) and includes a proximal body portion (not shown) and a tool assembly having an anvil assembly 906B and a cartridge assembly 908B. However, MULU 900B differs from SULU 400 (FIG. 53) mainly in that cartridge assembly 908B is configured to removably receive a staple cartridge 910B that, after use, is replaced with a replacement staple cartridge 910B for subsequent use of MULU 900B. Alternatively, MULU 900B may contain multiple staple cartridges disposed therein to enable repeated use without requiring replacement of staple cartridge 910B. Similar to SULU 400 (FIG. 53), MULU 900B includes an internal memory chip that includes a memory configured to store data pertaining to MULU 900B. Generally, MULU 900B is operated when attached to adapter 200 (FIG. 20) in a similar manner as described above with regard to SULU 400 (FIG. 53).

Transverse loading unit 900C and curved loading unit 900D, as illustrated in FIGS. 69C and 69D, respectively, are still further configurations of loading units configured for use with surgical device 100. Similar to SULU 400 (FIG. 53) and the other embodiments of loading units detailed herein, transverse loading unit 900C and curved loading unit 900D each include an internal memory chip having a memory configured to store data pertaining to the respective loading unit 900C, 900D and are generally operated when attached to adapter 200 (FIG. 20) in a similar manner as described above.

Figure 15:
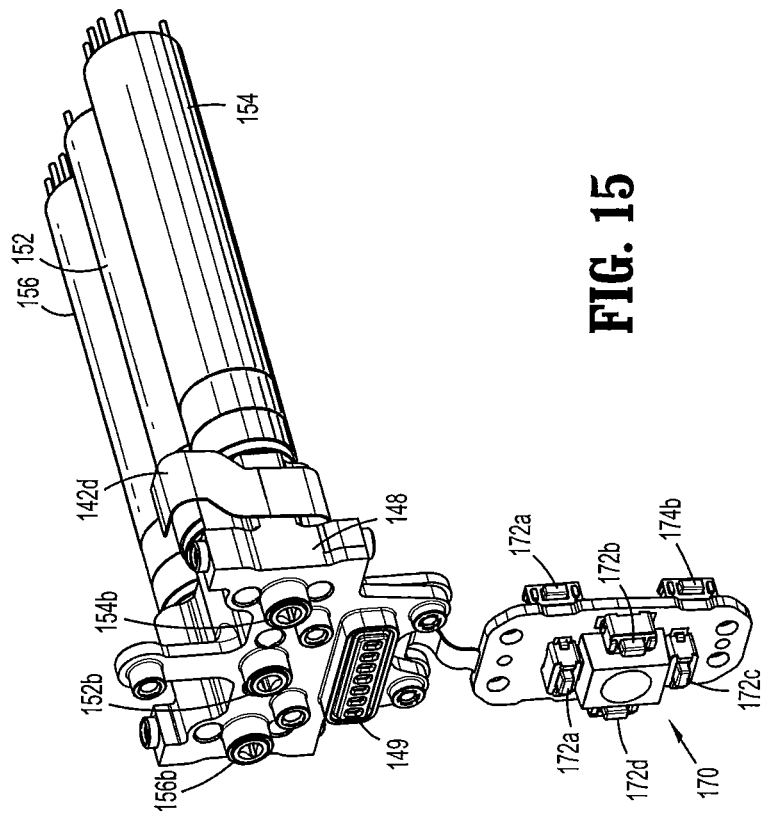
FIG. 15 is a front, perspective view of a motor assembly and a control assembly of the power-pack core assembly of FIG. 14.

Turning now to FIGS. 70-82 the communication, safety, and control features of surgical device 100 are described. As noted above, controller circuit board 142 of power-pack core assembly 106 includes motor controller circuit board 142a and main controller circuit board 142b. Controller circuit board 142 is coupled to battery circuit board 140 and a switch board 177 of switch assembly 170 (FIG. 15).

Main controller circuit board 142b includes master chip 157 and supports memory 165, which in an embodiment, is a micro SD memory. Main controller circuit board 142b further includes a 1-wire communication system including three 1-wire buses. A 1-wire master chip 166 of main controller circuit board 142b controls communications across three 1-wire buses 167, 169, 171. Although described herein as a 1-wire communication system, it is contemplated that other suitable communication systems for enabling the functionality detailed herein may also be provided.

First 1-wire bus 167 establishes a communication line between master chip 157 and motor controller circuit board 142a, which connects to battery circuit board 140 of battery 144 when battery 144 is present, thereby establishing a communication line between power-pack core assembly 106 and battery 144.

Second 1-wire bus 169 establishes a communication line between master chip 157 and a switchboard/adapter intermediate 175, which includes electrical adapter interface receptacle 149, and is configured to connect to a 1-wire memory chip of circuit board 294 of adapter 200 when adapter 200 is present. Switchboard/adapter intermediate 175 also couples switch board 177 with main controller board 142b via a third ribbon cable 142e. Second 1-wire bus 169 establishes a communication line between power-pack core assembly 106 and adapter 200 and also enables information stored in the 1-wire memory chip of circuit board 294 of adapter 200 to be accessed, updated, and/or incremented by power-pack core assembly 106. Circuit board 294 of adapter 200, in addition to having the 1-wire chip, includes a memory and electrical contacts 292 that enable electrical connection to the power-pack core assembly 106 to allow for calibration and communication of data and control signals therebetween. The memory is configured to store data relating to adapter 200 such as unique ID information (electronic serial number); type information; status information; whether a loading unit has been detected, identified, and verified; usage count data; and assumed autoclave count data. Distal electrical contacts 272 of adapter 200, as noted above, are configured to electrically couple with the corresponding electrical contacts 330 of a loading unit engaged therewith, e.g., SULU 400, for communication therewith, while toggle switch 230 permits the power-pack core assembly 106 to detect the presence of SULU 400. The memory of the SULU 400 stores data relating to SULU 400 such as a serial number, the type of the loading unit, the size of the loading unit, the staple size, the length of the loading unit, and an indication of whether the loading unit has been fired. Power-pack core assembly 106 is capable of reading this information stored in the memory of SULU 400 via adapter 200.

Third 1-wire bus 171 enables communication between master chip 157 in power-pack core assembly 106 and the 1-wire memory chip of outer shell housing 10. As detailed above, the 1-wire chip in outer shell housing 10 includes a memory that stores a unique ID of outer shell housing 10 and is capable of being updated to mark outer shell housing 10 as "used." Electrical contacts associated with the outer shell housing 10 form part of third 1-wire bus 171 and enable communication between power-pack core assembly 106 and 1-wire chip of the outer shell housing 10.

Power-pack core assembly 106 further includes and/or is coupled to various hardware components (some of which have been detailed above) that facilitate the various functions of power-pack core assembly 106 including: a Wifi board 182, the display screen 146, an accelerometer 184, the universal serial bus (USB) port 180, an infrared detection module 186, a real-time clock (RTC), an expansion port 188, and the FPGA 162, which as mentioned above enables communication between main controller 157 and motor controllers "MC0," MC1," "MC2" of motor controller circuit board 142a. Wifi board 182 and/or USB port 180 are used for communicating data collected by power-pack core assembly 106, adapter 200, and/or loading unit 300 to an external communication system. Accelerometer 184 enables determination of whether power-pack core assembly 106 has been manipulated, rotated, moved, etc. The RTC provides a reference from which the various time and/or duration-dependent functionality may be established.

Figure 71:
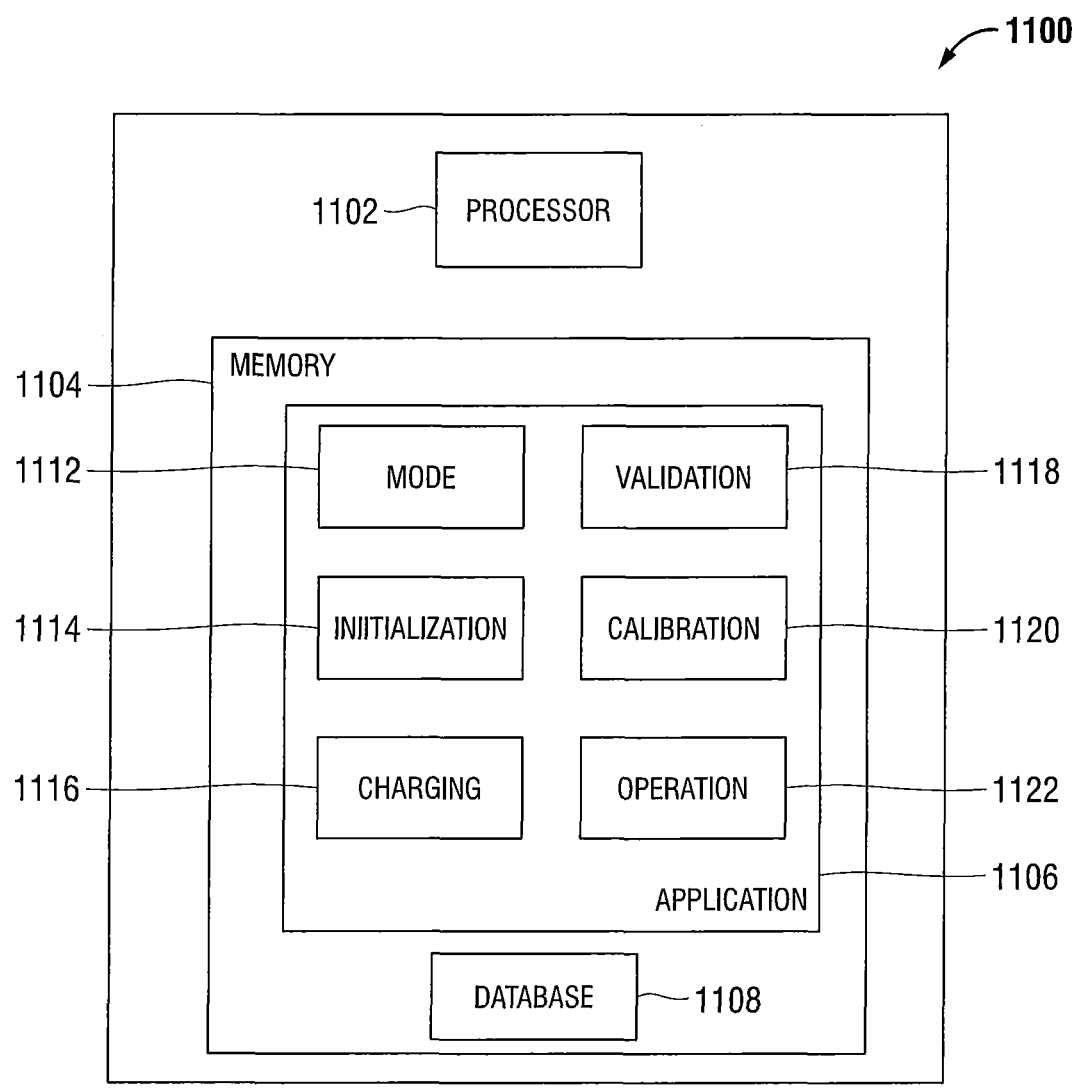
FIG. 71 is a block diagram of a simplified system hardware of the power-pack of the handheld surgical device of FIG. 1.

FIG. 71 is a block diagram of a simplified system architecture 1100 for controlling components of surgical device 100 (FIG. 1). Architecture 1100 includes a processor 1102 in operable communication with a memory 1104, which has various modules that include instructions for surgical device 1000 to operate in a desired manner, based on received user input or detected data. Processor 1102 is included on one or more of the boards of controller circuit board 142 (FIG. 70) and is made up of one or more devices. Here, for example, master chip 157, motor controllers "MC0," "MC1," "MC2," 1-wire master chip 166, and other controllers make up processor 1102 (see FIG. 70). Memory 1104 is computer-readable media and resides in one or more locations, such as, for example, memory 165 of main controller circuit board 142 and the 1-wire memory chips of adapter 200 and outer shell housing 10 (see FIGS. 1 and 70). In an embodiment, memory 1104 may include one or more solid-state storage devices such as flash memory chips. Alternatively or in addition to the one or more solid-state storage devices, memory 1104 may include one or more mass storage devices connected to the processor 1102 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 1102. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by processor 1102.

Memory 1104 includes an application 1106, which stores instructions for the operation of surgical device 100 (FIG. 1), and a database 1108, which stores collected data relating to surgical device 100 (FIG. 1). Application 1106 includes a mode module 1112, an initialization module 1114, a charging module 1116, a validation module 1118, a calibration module 1120, and an operation module 1122. Each of these modules will be described in greater detail below.

Figure 72:
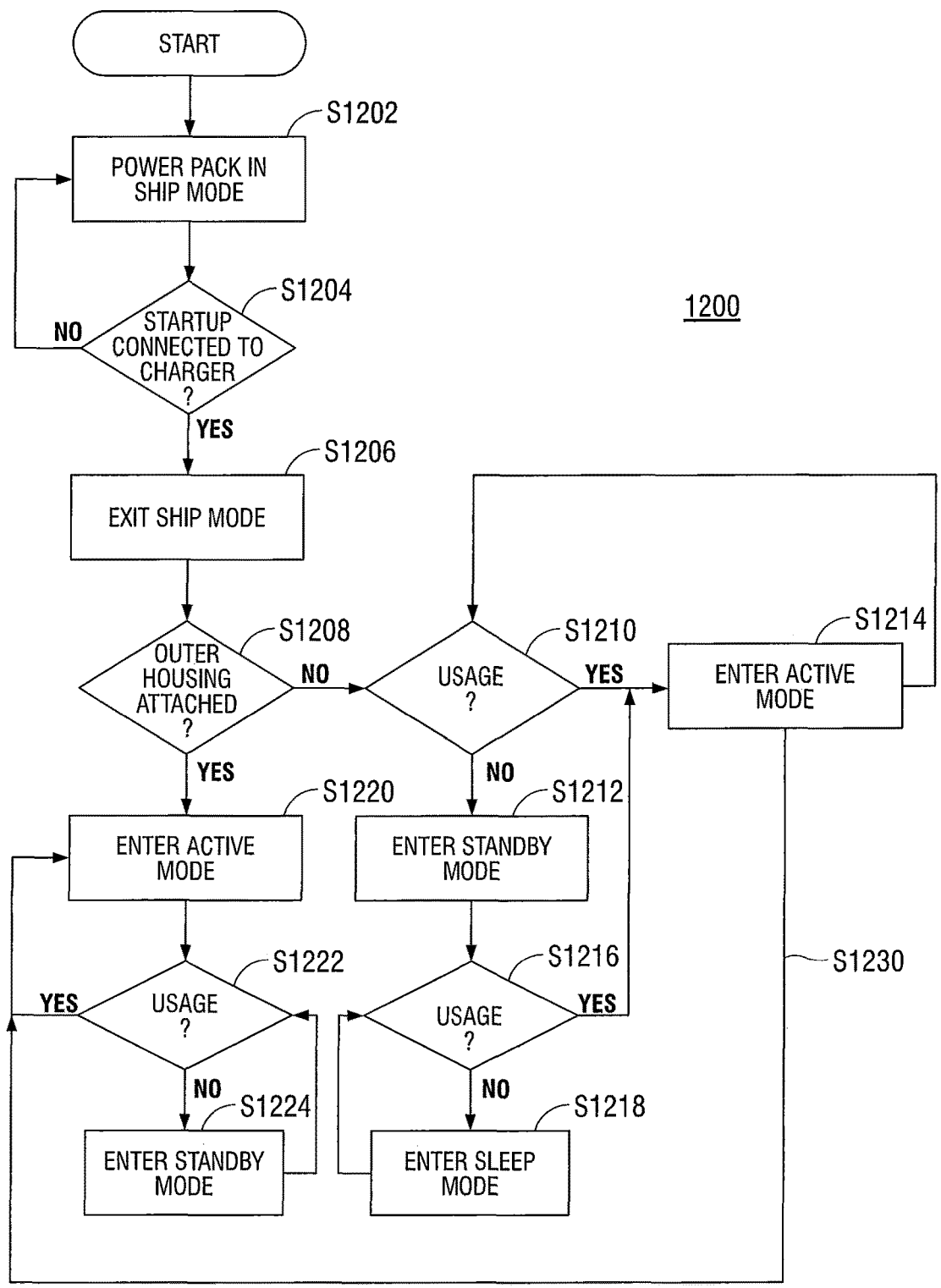
FIG. 72 is a flow diagram of a method for controlling various modes of the power-pack of the handheld surgical device of FIG. 1.

Mode module 1112 instructs a power-pack (e.g., power-pack core assembly 106 (FIG. 13)) to enter or exit operational modes and enters/exits these modes depending upon its condition, last use, motion, whether any components are attached, and/or whether it is connected to a charger. Specifically, the power-pack is transitionable from a ship mode and, thereafter, between a standby mode, a sleep mode, and an active mode. FIG. 72 is a diagram of a method 1200 depicting a flow by which the power-pack enters/exits the various modes thereof. Initially, the power-pack is in the ship mode at S1202. When the power-pack enters initial startup at S1204, it undergoes an initialization wherein the ship mode is permanently exited at S1206. It is contemplated that the battery of the power-pack be provided in an uncharged state and, as such, initialization begins upon connection of the power-pack with the charger. Until such initialization, the power-pack remains in ship mode at S1202. Once the ship mode has been exited, the power-pack is transitional between the standby mode, the sleep mode, and the active mode, and enables and/or disables certain functionality based upon its mode.

Entry into one of the various modes depends on whether the power-pack includes a clamshell, e.g., outer shell housing 10, engaged thereabout. Accordingly, with continued reference to FIG. 72, a determination is made as to whether the outer shell housing is attached to the power-pack at S1208. With respect to surgical device 100, this determination is made by the master chip 157 scanning third 1-wire bus 171 in search of a 1-wire memory chip of outer shell housing 10 (see FIGS. 1 and 70). When no outer shell housing is attached, an "insert clamshell" screen is displayed on a display screen to communicate to the user that no outer shell housing is attached to the power-pack. While the outer shell housing is not attached to the power-pack, button presses do not elicit motor responses. For example, open, close, safety and articulate buttons do not function. However, the power-pack is able to connect to an external communication system, and a screen depicting connection to the external communication system is displayed on the display screen. If a rotate button is pressed, a current power-pack statistics screen is displayed for a desired duration, for example, five (5) seconds.

Next, a determination is made as to whether the power-pack has been used at S1210. Usage includes, for example, placing the power-pack on the charger for recharging the battery, e.g., battery 144 (FIG. 70), pressing any of the various buttons on the power-pack, attaching an outer shell housing to the power-pack, or manipulating the power-pack (as determined by the accelerometer). When the power-pack has been idle for a time period that is greater than a first predetermined threshold duration, e.g., thirty (30) seconds of no usage, the power-pack enters standby mode at S1212. Otherwise, the power-pack enters an active mode at S1214. As indicted by S1230, if entry into the active mode at S1214 is triggered via connection of an outer shell housing to the power-pack, the active mode at S1220, which is detailed below, is achieved.

At S1216, while in standby mode, another determination is made as to whether the power-pack is being used. Here, a determination is made as to whether the power-pack has been idle for a time period that is greater than a second predetermined threshold duration, where the second predetermined threshold duration of step S1216 is greater than the first predetermined threshold duration of step S1210, for example, in a range of five (5) to twenty (20) minutes, e.g., fifteen (15) minutes. If at S1216 the power-pack does not remain idle for a time period that is greater than the predetermined threshold duration, the power-pack enters an active mode at S1214. If the power-pack does remain idle for a time period that is greater than the predetermined threshold duration, the power-pack exits the standby mode and enters a sleep mode at S1218. Method 1200 then proceeds to S1216 to determine whether to exit sleep mode and enter active mode at S1214 or remain in sleep mode at S1218.

Returning to S1208, when an outer shell housing is attached to the power-pack, the active mode is entered at S1220 so that the power-pack is ready for use. For instance, the power-pack monitors 1-wire bus 171 (FIG. 70) at a minimum rate of 1 Hz for the presence of attachment of an outer shell housing 10 (FIG. 1). A determination then is made at S1222 as to whether the power-pack is in use. Usage includes, for example, motion of the power-pack, pressing any of the various buttons, detection of another outer shell housing (e.g., if the outer shell housing is removed and replaced with another outer shell housing), or attachment of an adapter. When the power-pack is in use, the power-pack remains in the active mode and returns to S1220. When the power-pack is not in use after a predetermined threshold duration, for example, after one (1) minute of non-usage, the power-pack enters the standby mode at S1224. During the standby mode, the power-pack returns to S1222 continuing to monitor whether usage occurs. In an embodiment, if the outer shell housing is a demonstration component, motion does not cause the power-pack to exit the standby mode. If an adapter, e.g., adapter 200, is already attached to the power-pack, attachment of a loading unit, e.g., SULU 400 (FIG. 1), loading unit 900A (FIG. 69A), MULU 900B (FIGS. 69B1 and 69B2), loading unit 900C (FIG. 69C), or loading unit 900D (FIG. 69D), to the adapter will also cause the power-pack to exit the standby mode and to enter the active mode at S1220. Multi-use loading units, e.g., MULU 900B (FIGS. 69B1 and 69B2), include replaceable staple cartridges, and hence, may be referred to as a reload. For purposes of consistency in describing the methods performed by application 1106, loading units and reloads for use with multi-use loading units will be referred to below simply as "reloads."

Initialization module 1114 controls initialization of the power-pack. In particular, initialization module 1114 includes instructions for the power-pack to perform a plurality of self-tests at initialization, which occurs when the power-pack exits the ship mode, the power-pack is removed from the charger, the power-pack is woken up from sleep mode, or when initiated by the user. The initialization self-tests include a test of the display screen, a test of the memory of the power-pack, an RTC test, an FPGA communication test, a test of the motor and drive electronics, a test of the accelerometer, a button active test, a plurality of 1-wire tests, and a use-remaining test.

Figure 73:
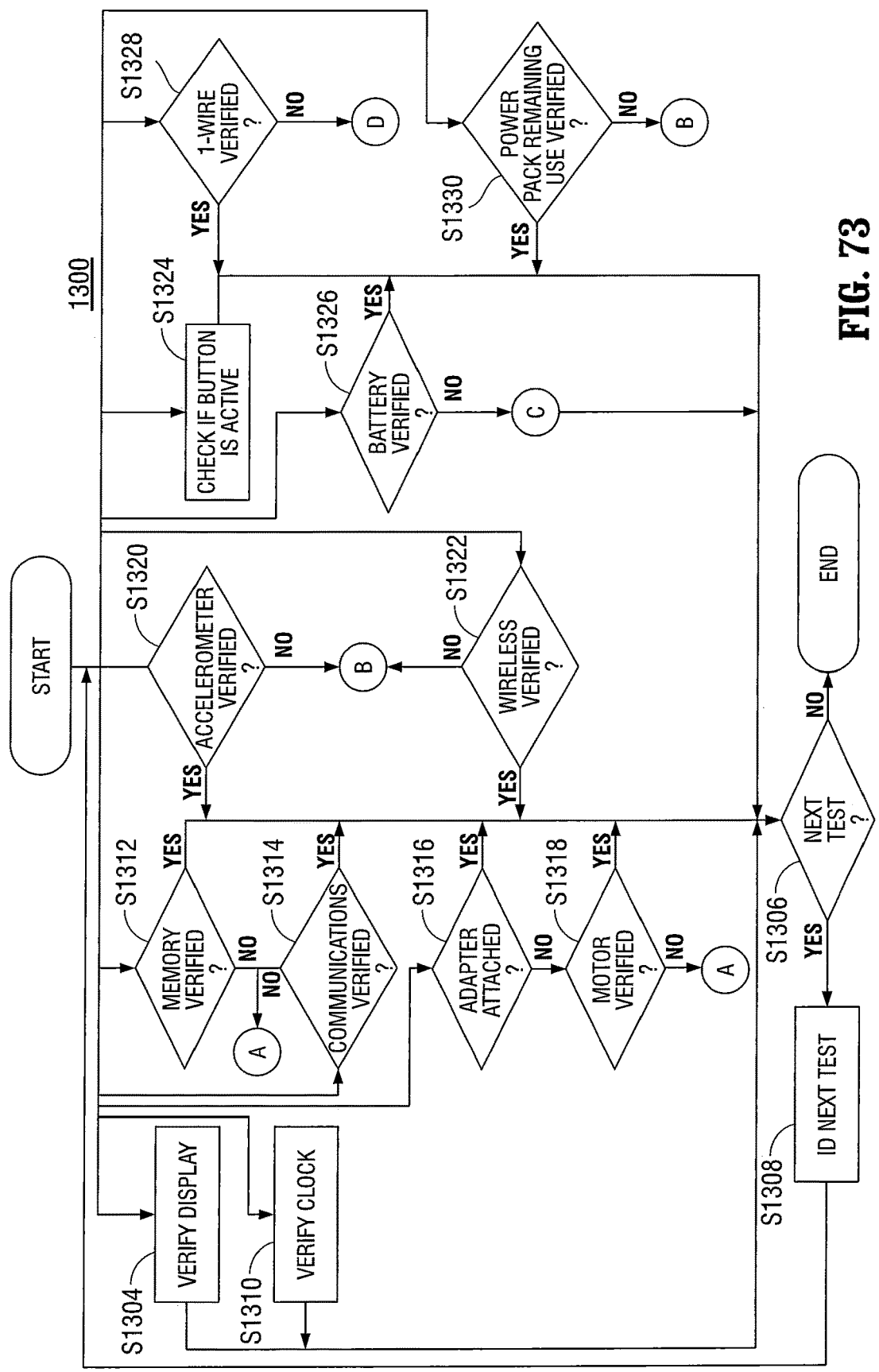
FIG. 73 is a flow diagram of a method of initializing the power-pack of the handheld surgical device of FIG. 1.

Turning now to FIG. 73, a flow diagram is provided depicting a method 1300 for initializing the power-pack. Initialization begins at S1302 when the power-pack exits the ship mode, the power-pack is removed from the charger, the power-pack is woken up from the sleep mode, or when initiated by the user. Although any one of the initialization tests can be initially performed, for the purposes of this description, the display screen is initially tested at S1304. The display test includes verifying communication capability between the power-pack and the display controller, turning on all pixels to the color white for 500 milliseconds (mS), and, upon completion, displaying the "welcome" screen on the display screen. Next, a determination is made at S1306 as to whether any of the initialization tests have not yet been performed. If so, a next test to be performed is identified at S1308. If not, method 1300 ends.

If identified as being next to be performed, the clock is verified at S1310. In an embodiment, testing is performed to determine whether the clock is functional. Next, S1306 is performed, and S1308, if needed, is performed to identify a next test.

Figure 74:
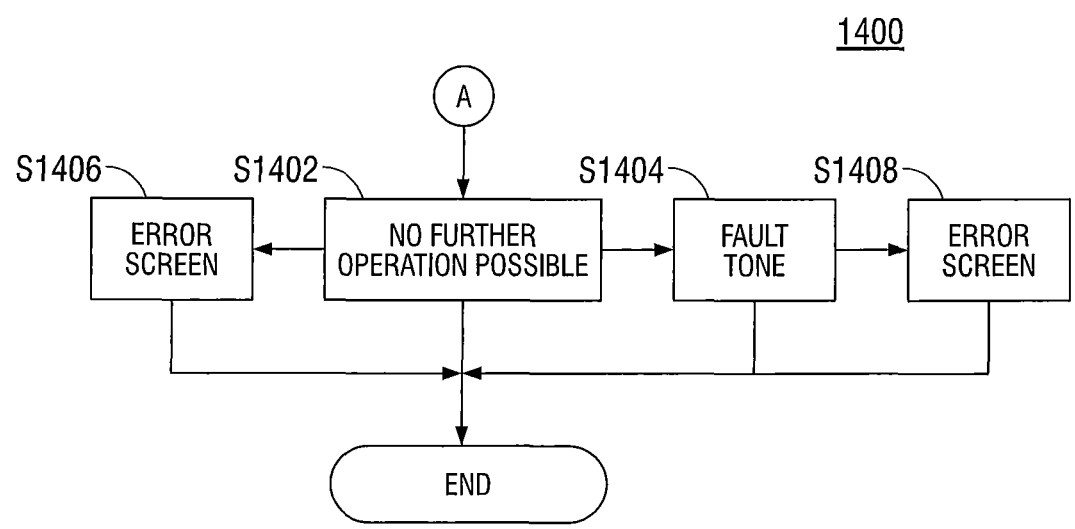
FIG. 74 is a flow diagram of a portion of the method of initializing of FIG. 73.
Figure 75:
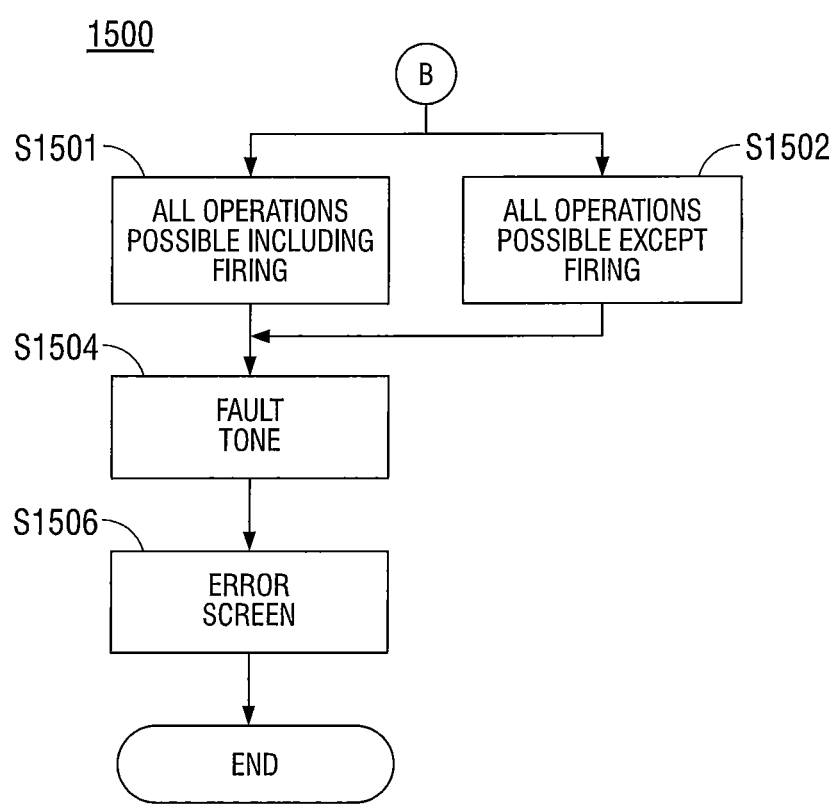
FIG. 75 is a flow diagram of another portion of the method of initializing of FIG. 73.
Figure 76:
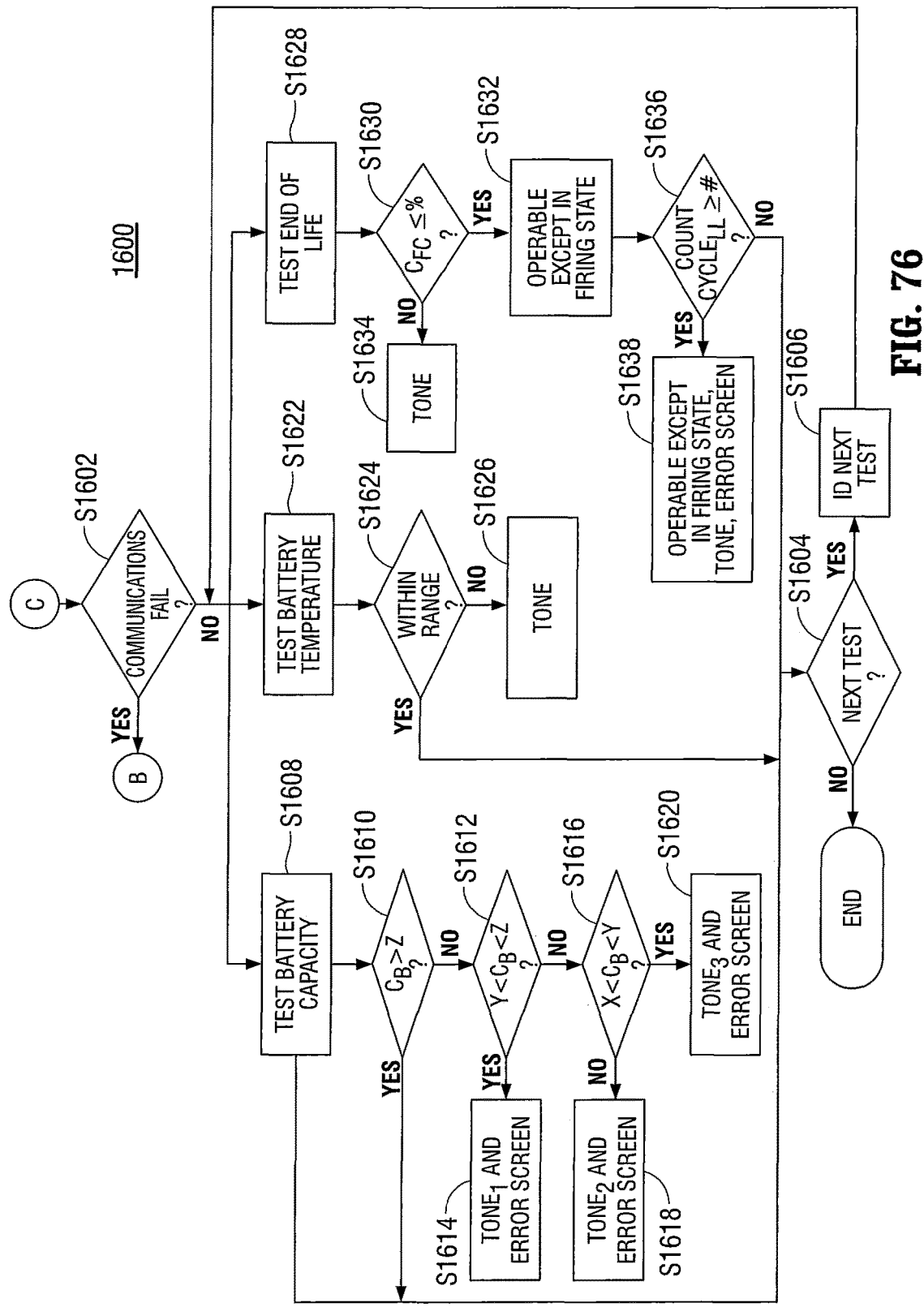
FIG. 76 is a flow diagram of yet another portion of the method of initializing of FIG. 73.

If identified as being the next test to be performed, the memory of the power-pack is verified at S1312. For example, verification includes one or more of verifying the integrity of the code stored in the program memory of the power-pack, the integrity of the external SRAM, the ability to communicate with the SD memory, e.g., memory 165 (FIG. 70), and the integrity of the file system on the SD card. In an embodiment, if the integrity of the code is not verified, method 1400 is performed as shown in FIG. 74. In particular, if verification of the code fails, no further operation is possible at S1402 and method 1400 ends. If the verification operation fails, method 1400 at S1402 is performed (i.e., no further operation is possible) and a fault tone occurs at S1404. If verification of the ability to communicate with the SD memory fails, method 1400 at S1402 is performed (i.e., no further operation is possible) and a fault tone occurs at S1404.

The fault tone is a single tone or a series of tones within a frequency range. For example, the fault tone is a pattern of tones including a tone within a frequency range of 500 Hertz (Hz)±50 Hz with a duration of 225 mS followed by a tone within a frequency range of 250 Hertz (Hz)±25 Hz with a duration of 225 mS and so on. If the integrity of the file system on the SD card is not verified, the fault tone also occurs at S1404. After the memory is tested, method 1300 advances to S1306, where a determination is made as to whether any more of the initialization tests remain to be performed, and, if needed, identifying a next test to be performed at S1308.

In an event in which communication verification is identified as the next test to be performed, step S1314 is performed. In particular, an FPGA communication test is performed to verify that the FPGA is operational. If the FPGA communication test fails, S1402 (no further operation is possible), and S1406 (where an error screen is displayed on the display) are performed. Method 1300 advances to S1306 and S1308, if needed, to identify a next test to be performed.

If not yet already performed, a determination is made as to whether an adapter is attached at S1316, and if not, a test of the motor and drive electronics is performed to verify the motors of the power-pack at S1318. In an event in which any of the motors are unable to attain a commanded position, no further operation is possible as indicated in S1402. If one or more of the motors fail, a fault tone occurs as S1404, and an error screen is displayed at S1408.

If at S1316, the adapter is identified as being attached or the electronics are verified, method 1300 advances to S1306 and, if needed, to S1308 to identify a next test to be performed. If an accelerometer check has not yet been performed, method 1300 advances to S1320, during which verification is made as to whether the accelerometer of the power-pack is functional. If the accelerometer is not functional, method 1300 advances to method 1500 of FIG. 75. In particular, all operations including firing are possible at S1501, a fault tone occurs (S1504), and an error screen is displayed on the power-pack (S1506). If the accelerometer is functional, method 1300 advances to S1306 and, if needed, to S1308 which, as noted above, is performed to identify a next test to be performed.

If identified as the next test to be performed, wireless functionalities are verified at S1322. If the wireless functionalities are verified, method 1300 advances to S1306, and if needed, to S1308 to identify a next test to be performed. If the wireless functionalities are not verified, all operations including firing are possible (S1501), a fault tone occurs (S1504) and an error screen is displayed on the power-pack (S1506).

Verification is made with regard to whether a button is active at S1324, if not already performed. In the event that the button is active during initialization method 1300, user operations are ignored until the button is deactivated. Method 1300 then advances to S1306, where a determination is made as to whether any other initialization test has not been performed. If so, a next test to be performed is identified at S1308. If not, method 1300 ends.

If identified as a next test to be performed, the operability of the battery is verified at S1326. In an embodiment, numerous tests are performed on the battery. A method 1600 for testing the battery is provided in FIG. 76. The battery is initialized by disabling a broadcasting capability of the battery to prevent unsolicited messages from being sent. In the event that communication with the battery fails at 1602, the method 1600 advances to FIG. 75, where all operations except firing are possible (1502), a fault tone occurs (1504), and an error screen is displayed on the power-pack (1506).

If communication does not fail, method 1600 proceeds to perform one of the battery tests. Although any of the tests can be initially performed, for the purposes of this description, method 1600 performs the battery capacity ($C_{Batt}$) test at S1608. The battery capacity may be displayed on the display. In an embodiment, battery capacity testing is performed by determining whether the battery capacity is above a threshold value (e.g., $z<C_{Batt}$) at S1610. If the battery capacity is not above the threshold value, a determination is made as to whether the battery capacity is within a first range (e.g., $y<C_{Batt}<z$), where the threshold value is an upper limit of the first range at S1612. If so, a tone occurs and a "low battery" error screen is displayed at S1614. In an embodiment, the tone is one that is distinguishable from the fault tone and that indicates a low battery. For example, a sequence indicating a low battery occurrence may include a tone at a frequency of 1000 Hz for 50 mS, followed by no tone, followed by a tone at a frequency of 800 Hz for 50 mS, followed by no tone, followed by a tone at a frequency of 600 Hz, followed by no tone, followed by a tone at a frequency of 400 Hz, followed by no tone.

If the battery capacity is not within the first range, a determination is made at S1616 as to whether the battery capacity is within a second range (e.g., $x<C_{Batt}<y$), where an upper limit of the second range is equal to or below a lower limit of the first range. If the battery capacity is within a second range, a tone indicating an insufficient battery occurs and an "insufficient battery" error screen is displayed at S1618. The tone indicating an insufficient battery differs from the tone indicating a low battery. In an embodiment, the low battery tone is a series of tones each at a frequency of 400 Hz±40 Hz in a pattern of on for 50 mS, then off for 50 mS repeated twelve (12) times, and ending with the tone being played for 750 mS.

If the battery capacity is not within the second range and thus, is below a lower limit of the second range (e.g., $C_{Batt}<x$), then a tone indicating a dead battery occurs and a "dead battery" error screen is displayed at S1620. The tone indicating a dead battery differs than the tones indicating an insufficient battery or a low battery. In an embodiment, a dead battery is indicated by a series of tones each at a frequency of 400 Hz±40 Hz in a pattern of on for 100 mS, then off for 50 mS, where the pattern is repeated twelve (12) times, and a last tone in the series is played for 750 mS.

Referring again to S1610, if the battery capacity is above the threshold value (z), method 1600 proceeds to S1604, where a determination is made as to whether any of the battery tests have not yet been performed. If so, a next battery test to be performed is identified at S1606. If not, method 1600 ends.

If not yet already performed, the battery temperature is tested at S1622. A determination is made as to whether the battery temperature is in a desired range at S1624. In an example, the desired range is 15 to 70 degrees Celsius (° C.). In another embodiment, the desired range is wider than or overlaps the aforementioned range. In yet another embodiment, the desired range is above or below the aforementioned range. If the battery temperature is not within the desired range, either exceeding or falling below the range, a fault tone occurs at S1626. If the battery temperature is within the desired range, method 1600 returns to S1604 and S1608 to identify a next test to be performed, if any.

If not already performed, a battery end-of-life test is performed at 1628 to test a battery full charge capacity for end-of-life condition. In this regard, a determination is made as to whether the battery full charge capacity is less than or equal to a predetermined percentage of design capacity at S1630. In an example, the predetermined percentage is about 82%. If the battery full charge capacity is less than or equal to the predetermined percentage, the power-pack is operable except for entering a firing state at S1632. If the battery full charge capacity is greater than the predetermined percentage, the test fails and fault tone occurs along with a display of the error on the error screen at S1634. A battery charge cycle count is also tested. In particular, a determination is made as to whether the battery charge cycle count is equal to or over a predetermined number of charge cycles at S1636. In an embodiment, the predetermined number of charge cycles is three hundred (300) charge cycles. If the battery charge cycle count is equal to or over the predetermined number of charge cycles, the power-pack core assembly 106 can be operated except for entering a firing state, a fault tone occurs, and an error screen is shown on the display at S1638. Otherwise, method 1600 advances to S1604, and to S1606, if needed.

Returning to FIG. 73, after the battery testing, method 1300 proceeds to S1306, to determine whether any of the initialization tests have not yet been performed. If so, a next test to be performed is identified at S1308. If not, method 1300 ends.

In an instance in which wire testing has not yet been performed, a plurality of wire tests are performed at S1328 to verify communication capability between the master chip of the power-pack and the various components of the system along the 1-wire bus system. The tests are also employed to verify and record identifying information of the various components. More specifically, tests on all three buses—one between the power-pack and battery, another between the power-pack and outer shell housing, and another between the power-pack and adapter—are performed, followed by verification and identification along the three buses individually. The power-pack monitors the 1-wire buses at a minimum rate of 1 Hz for the presence of an attached outer shell housing, adapter, and/or reload.

Figure 77:
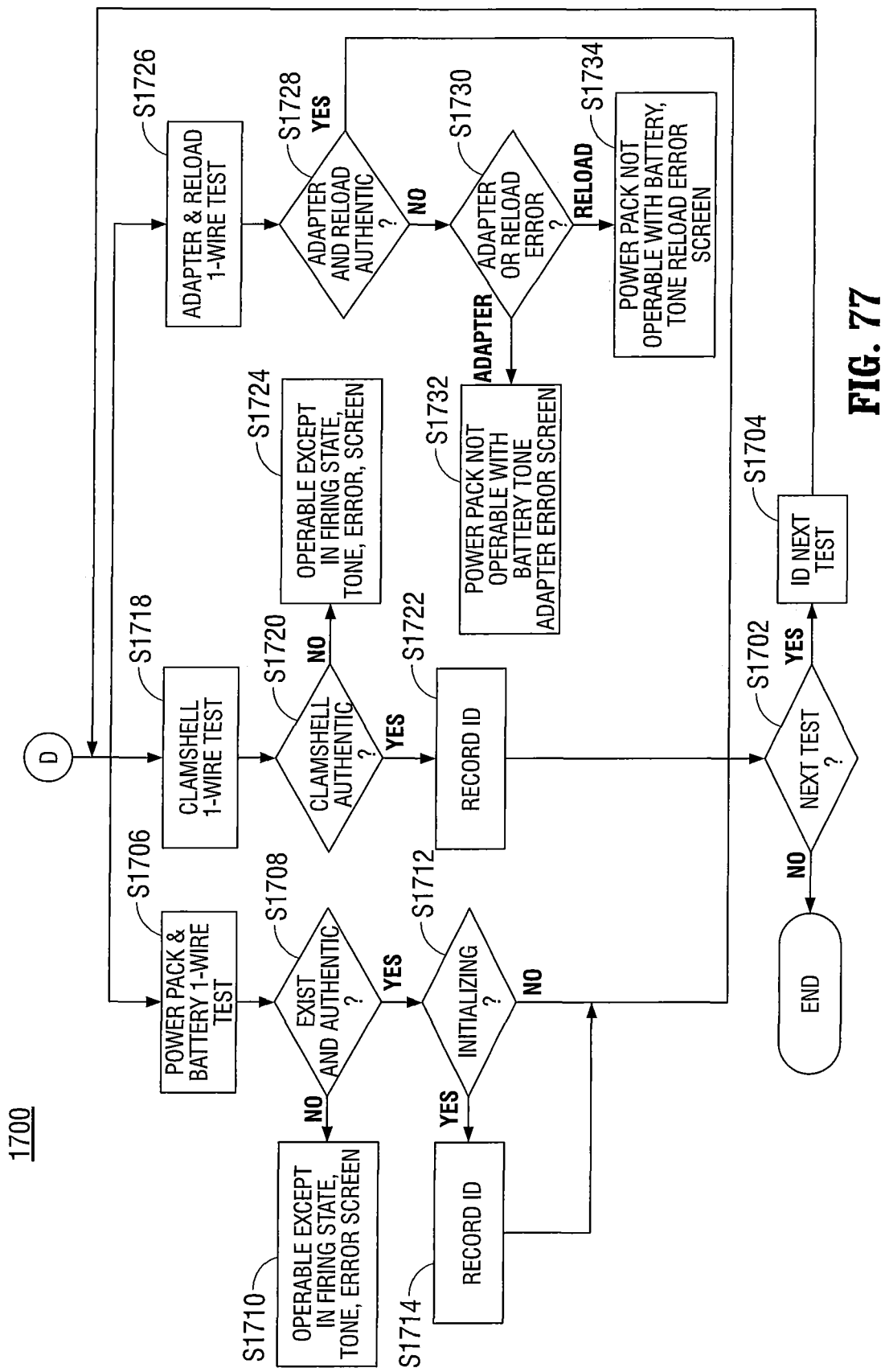
FIG. 77 is a flow diagram of a wire testing method of the method of initializing of FIG. 73.

Turning to FIG. 77, a method 1700 for testing the wires is depicted. Although any one of the wire tests can be initially performed, for the purposes of this description, method 1700 begins with a power-pack and battery 1-wire test at S1706. Here, a determination is made as to whether a connection between the power-pack and battery 1-wire exists and is authentic at S1708. If the connection between the power-pack and battery 1-wire exists but is not authentic (e.g., a 1-wire or authentication error results), use of the power-pack remains available, except for entering the firing state, a fault tone occurs, and an error screen is displayed at S1710. If the connection is authorized, a determination is made at S1712 as to whether the testing is being performed during initialization. If so, a battery identifier (ID) is recorded in the memory at S1714 so that the power-pack recognizes the recorded battery ID. As a result, if another battery with a different battery ID is used with the power-pack, an error screen is displayed and the power-pack is unable to operate with the unidentified battery. If the connection between the power-pack and battery 1-wire exists and is authentic and the test is not performed during initialization or if the ID has been recorded after detecting the initialization, the existence of a next test is determined at S1702, and if the next test exists, the next test is identified at S1704. If not, method 1700 ends.

If identified as being the next test to be performed, a clamshell 1-wire test is performed at S1718. At S1720, a determination is made regarding whether an outer shell housing is connected to the power-pack and whether the outer shell housing is authentic at S1720. In particular, a test across the outer shell housing 1-wire bus is performed to determine whether an outer shell housing is connected to the power-pack. If the outer shell housing is authentic, an identifier (ID) for the outer shell housing is obtained and recorded in the memory and the outer shell housing is marked as "used" in its memory at S1710. If there is an error detected or authentication fails, e.g., where the outer shell housing has previously been marked as "used," use of the power-pack is possible except for entering the firing state, a fault tone occurs, and an error screen is displayed at S1712. Method 1700 advances to S1702, and if needed, S1704.

If not already performed, an adapter and reload 1-wire test is performed at S1726. Here, a test is performed across the adapter 1-wire bus to determine if an adapter and/or a reload is connected and whether they are authentic at S1728. If there is an error detected or authentication fails, a determination is made as to whether the failure is due to the adapter or reload at S1730. If the failure is due to the adapter, use of the power-pack is possible except for entering firing state, a fault tone occurs, and an "adapter" error screen is displayed at S1732. If the failure is due to the reload. Additionally, use of the power-pack is possible except for entering firing state, a fault tone occurs, and a "reload" error screen is displayed at S1734.

With reference again to FIG. 73, after the wire testing, method 1300 advances to S1306, where a determination is made as to whether any of the initialization tests have not been performed. If so, a next test is identified to be performed at S1308. If a number of uses remaining of the power-pack has not yet been verified, such operation is performed at S1330. In particular, a determination is made as to whether a firing counter is equal to or greater than a predetermined value representing a fire limit. The firing counter, stored in the memory of the power-pack, is obtained, and if the firing counter is equal to or greater than the fire limit, method 1500 is performed where the power-pack is operable except for entering firing state (S1502), a fault tone occurs (S1504), and a screen image communicating that no uses left is displayed (S1506). After S1330, method 1300 returns to S1306 and S1308 to identify a next test to be performed, if any. If no test remains to be performed, method 1300 ends.

Prior to use, and in some instances, assembly, the battery of the power-pack is preferably charged, the performance of which is controlled by charging module 1116 (FIG. 71). In an embodiment, upon connection to the charger, charging module 1116 provides instructions to the power-pack to release master control of a bus used to communicate with the battery. Although master control is released, the power-pack receives the time and is capable of updating the clock during connection to the charger. Connection with the charger may be made via electrical contacts associated with the battery circuit board 140, communication therebetween may be accomplished over 1-wire bus 167 (see FIG. 70). In an embodiment, the power-pack is not connected to the external communication system and does not enter the standby mode while charging. Information is available for display. For example, information from a previous procedure, a remaining firing count and/or procedure count, and/or remaining firing and autoclave counts in any attached adapter are available to be read by the user. Upon removal of the power-pack from the charger, the power-pack is restarted.

Figure 78:
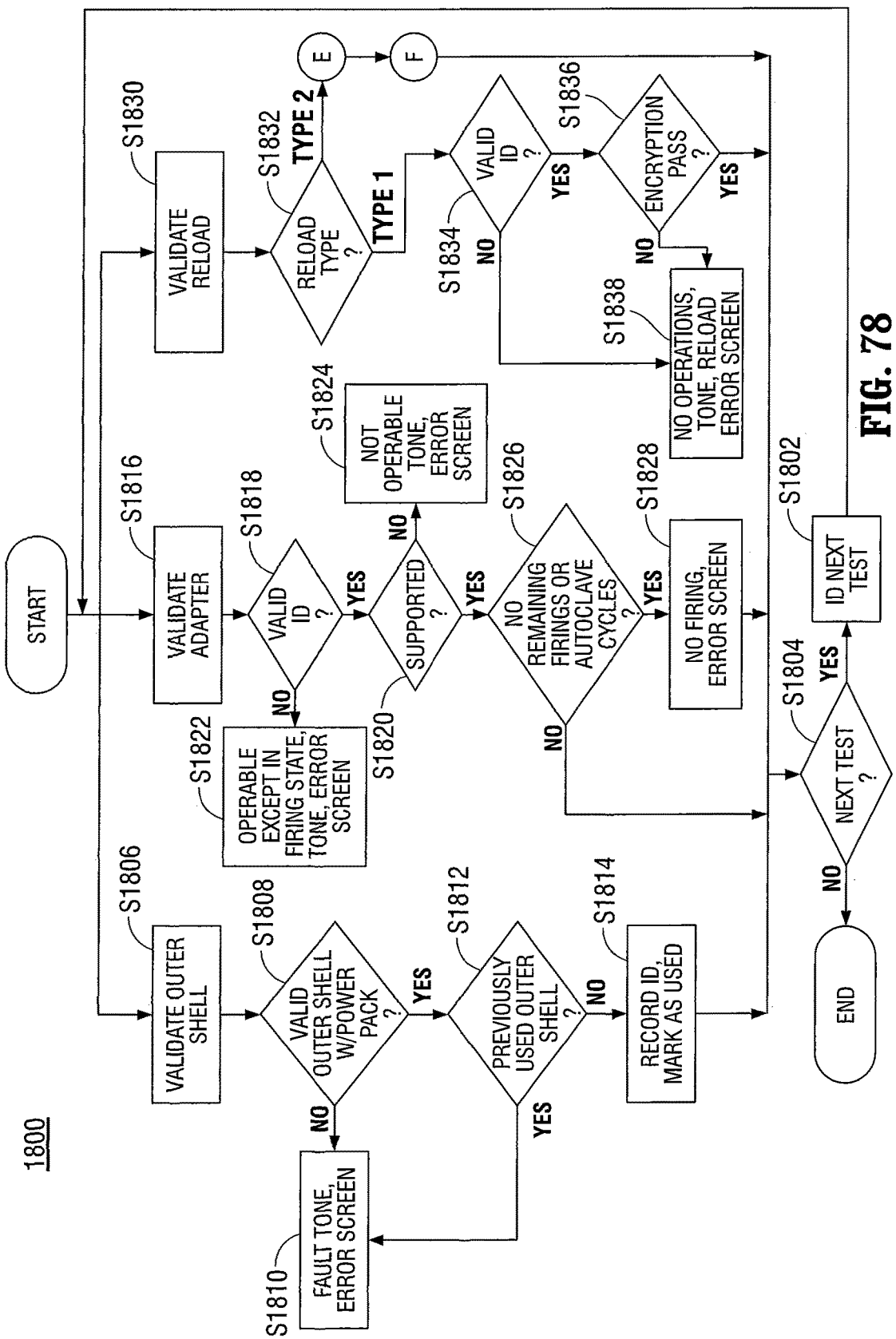
FIG. 78 is a flow diagram of a method of validating components of the handheld surgical device of FIG. 1.

During assembly of the surgical device, validation module 1118 provides instructions for performing testing to detect whether a component (e.g., outer shell housing, adapter, or reload) being connected to the power-pack is valid. FIG. 78 is a flow diagram of a method 1800 of validating the components, in accordance with an embodiment. Although any one of the validation tests can be initially performed, for the purposes of this description, outer shell housing validation with the power-pack is performed at S1806. In response to detecting engagement of an outer shell housing with the power-pack, the power-pack initiates a test, across the corresponding 1-wire bus, to determine whether the outer shell housing is valid at S1808. During the validation, a display screen indicating testing is displayed. If the outer shell housing is invalid or unsupported, a fault tone occurs and a "clamshell error" screen is displayed at S1810. In addition to determining validity, method 1800 includes identifying whether the outer shell housing has been previously used at S1812. In this regard, the memory of the outer shell housing is read for data, and the data is compared to data stored in the memory of the power-pack. If the outer shell housing has been previously used, method 1800 proceeds to S1810 where a fault tone is sounded and an error screen is displayed on the display screen. In an embodiment, the power-pack is also inhibited from entering the firing state.

Returning to S1808 and S1812, if a valid and unused outer shell housing is detected, the power-pack records the ID of the outer shell housing in the memory of the power-pack and marks the outer shell housing as used by writing such to its memory at S1814. Method 1800 then advances to S1802 and, if needed, to S1804 to identify a next test.

If not yet performed, the adapter is validated at S1816. The power-pack monitors the 1-wire bus at a minimum rate of 1 Hz for the presence of an adapter, and a "request adapter" screen is shown while waiting for the adapter, if a power-pack statistics is not already displayed on the display. In response to the detection of the adapter, the power-pack determines whether the adapter has a valid ID at S1818 and is supported at S1820. If the adapter is unable to be identified, an error screen is displayed, a fault tone is sounded, and entering the firing state is inhibited at S1822. If the adapter is found to be unsupported, no further operation is permitted, a fault tone is sounded, and an error screen is displayed at S1824. If the adapter has a valid ID and is supported, the values of the two counters associated with the adapter are examined at S1826. Specifically, the power-pack reads the identifying and counter data from the attached adapter. In an example, with respect to the counters, the power-pack reads the firing count and an assumed autoclave count stored in the memory of the adapter and compares these values to the limits stored in the memory of the power-pack. If the adapter is found to have no remaining firings or no remaining autoclave cycles, a screen indicating the same is displayed and entering the firing state is inhibited at S1828. Otherwise, method 1800 advances to S1802, and if needed, S1804, for the identification of a next test to be performed.

Figure 79:
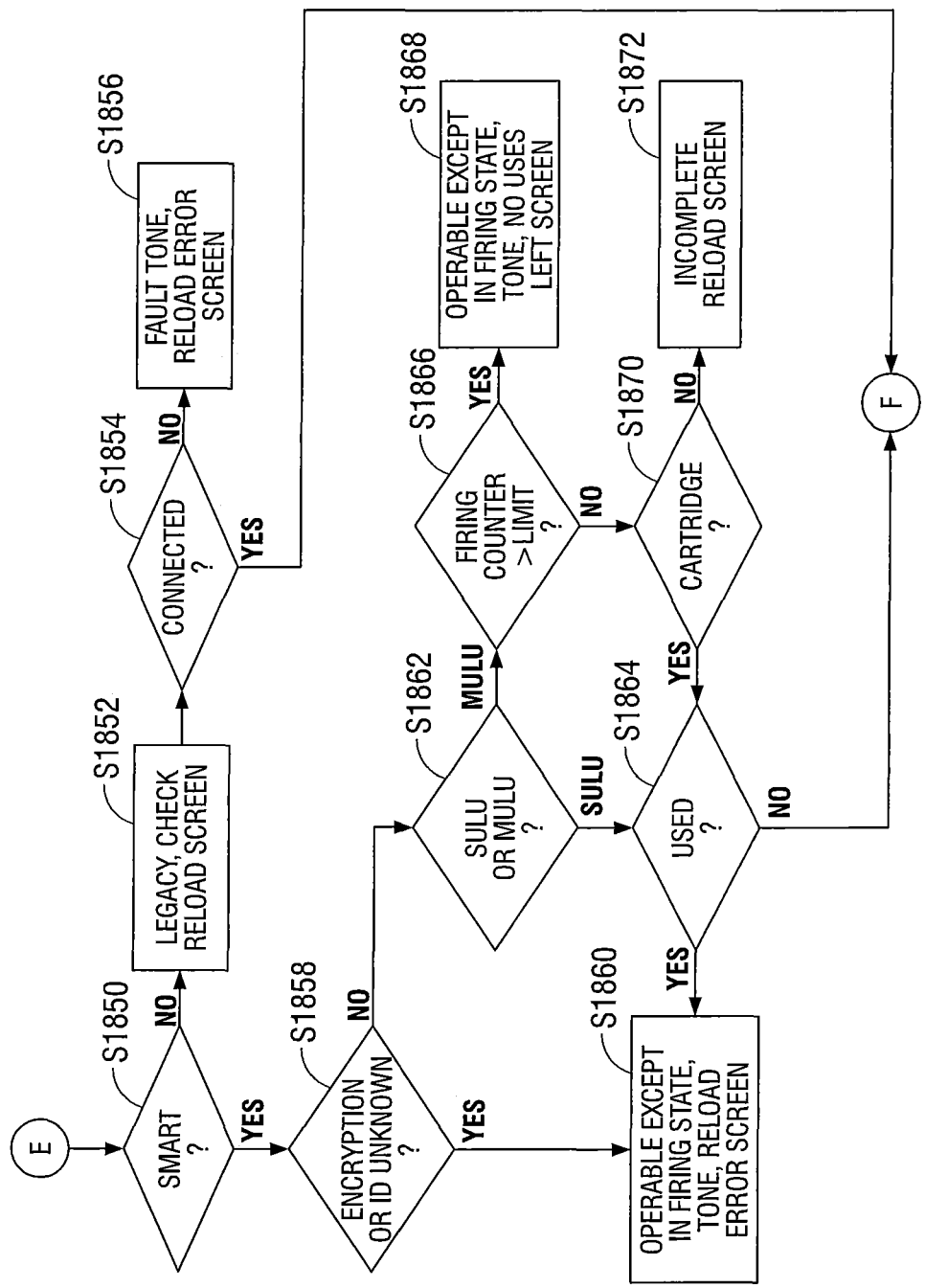
FIG. 79 is a flow diagram of a portion of the method of validating components of FIG. 78.

In an embodiment, the next test to be performed includes validating a reload at S1830. Turning now to FIG. 79, the power-pack monitors the 1-wire communication bus to the adapter to detect whether a reload is attached and the type at S1832. For example, as detailed above, a switch of the adapter is actuated upon coupling of the reload thereto, providing a detectable indication to the power-pack that a reload is attached.

As noted above, different types of reloads can be attached to the adapter. For the purposes of this description, a first type of reload is ones that is not recognized as being a SULU-type reload, e.g., similar to SULU 400 (FIG. 1), or a MULU-type reload, e.g., similar to MULU 900B (FIGS. 69B1 and 69B2). This "first type" reload may be, for example, loading unit 900A (FIG. 69A), loading unit 900C (FIG. 69C), or loading unit 900D (FIG. 69D). SULU-type reloads and MULU-type reloads are considered to be a "second type" of reload. SULUs and MULUs are readily identifiable and distinguishable by power-pack using the 1-wire communication system; however, for purposes of simplicity, both SULUs and MULUs are treated herein as being reloads of the second type. Further, although only two types of reloads, e.g., first types and second types, are detailed herein, it is understood that the power-pack can be configured to recognize any number of reload types.

If the first type of reload is detected, method 1800 advances to S1834, where the power-pack reads the memory of the reload in search of a reload ID. If a reload ID is detected, the power-pack tests the encryption of the reload ID at S1836. If at S1834 or S1836 either the reload ID is not recognized or the reload does not pass encryption, no operations are possible, a fault tone occurs, and a "reload error" screen is displayed at S1838. Otherwise, method 1800 advances to S1802, and if needed, to S1804.

Returning to S1832, if the second type of reload is detected, method 1800 advances to S1850, where a scan is made to determine whether the reload is capable of providing information, e.g., via a memory (with or without a processor) of the reload, RFID chip, barcode, symbolic label, etc., and/or the type of reload that is connected to the adapter. If the reload is determined not to be capable of providing information, the reload is identified as a legacy reload and a "check reload" screen is displayed at S1852. A check of whether the reload is connected properly is performed at S1854. If not connected properly, a fault tone occurs and a "reload error" screen is displayed at S1856. If the reload is connected properly, method 1800 returns to S1802 and S1804 (if needed) for the identification of a next test, if any.

If the reload is determined to be capable of providing information and/or the type of reload connected to the adapter is detected at S1850, the reload is considered a smart reload and an encryption of the smart reload is tested at S1858. If the encryption of the smart reload fails testing, operation can continue, except entering the firing state, the fault tone occurs, and the "reload error" screen is displayed at S1860. Similarly, if an unknown ID of the smart reload is detected or the 1-wire ID is detected by the reload switch is not property recognized, operation can continue, except entering the firing state, the fault tone occurs, and the "reload error" screen is displayed at S1860.

If encryption of the smart reload passes testing at S1858, a detection is made as to whether the second type of loading unit is a SULU, e.g., SULU 400 (FIG. 1), or a MULU, e.g., MULU 900B (FIGS. 69B1 and 69B2), at S1862. If a SULU is detected, the SULU is tested to detect whether it has been used at S1864. If it is determined to be used, the power-pack can be used, except entering firing state, a fault tone occurs, and a "reload error" screen is displayed at S1860. Otherwise, method 1800 returns to S1802 and S1804, if needed.

If a MULU is detected, a firing counter of the MULU is read to determine whether the firing counter is greater than a fire limit at S1866. If the firing counter is greater than a fire limit, the "no uses left" screen is displayed and the power-pack can be used, except entering firing state at S1868. If the firing counter is not greater than the fire limit at 1860, a scan is performed to detect a staple cartridge at S1870. If no staple cartridge is present, an "incomplete reload" screen is displayed at S1872. If a staple cartridge is present, method 1800 advances to S1864, to determine whether the staple cartridge has been used. Depending on the outcome at S1864, method 1800 may advance to S1860 or S1802 as described above.

Upon detection of a valid adapter with at least one use remaining and at least one autoclave cycle remaining, the operation functions are calibrated, instructions for which are provided by calibration module 1120. The calibration process can differ depending on the particular type of adapter attached to the power-pack.

Figure 80:
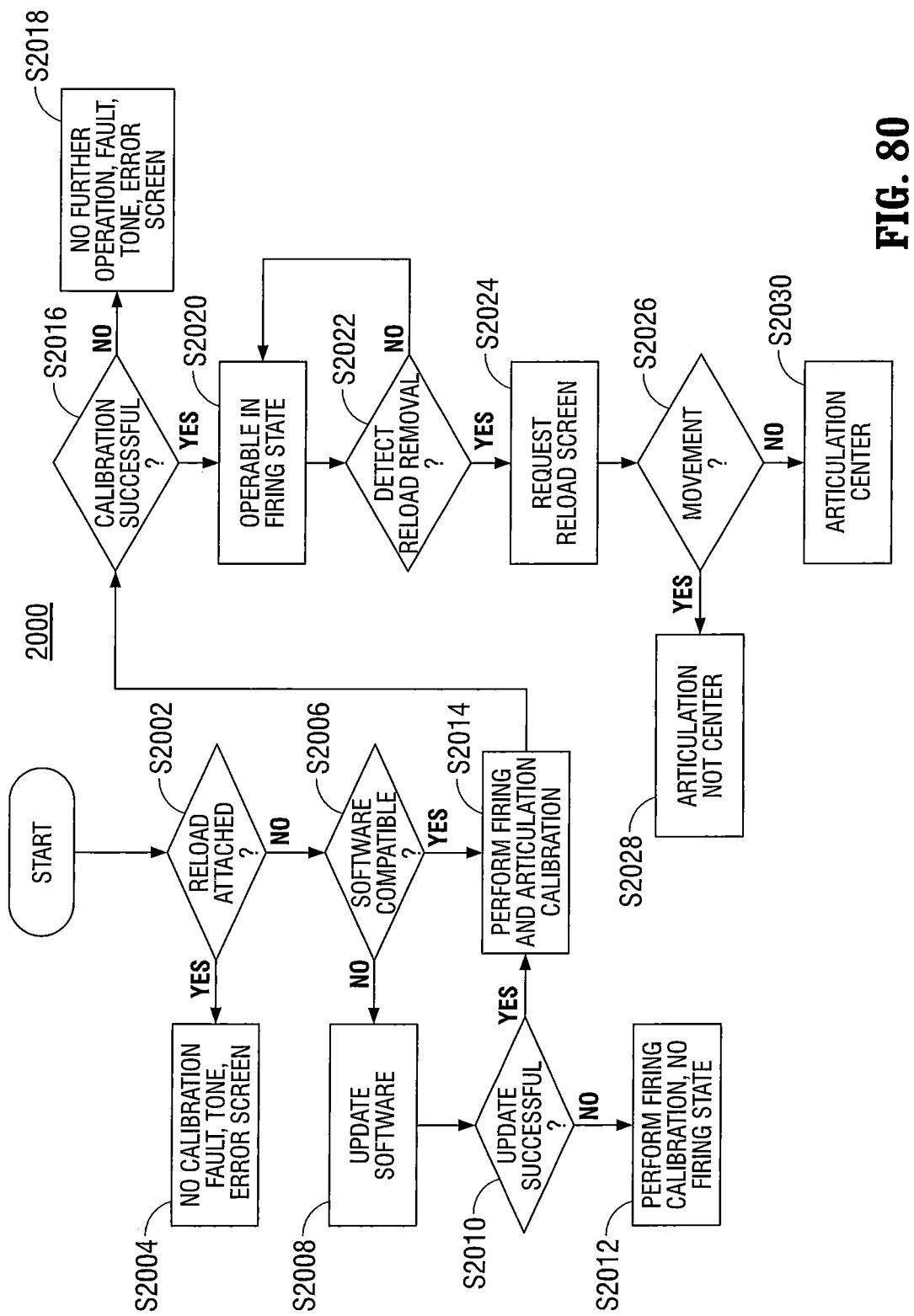
FIG. 80 is a flow diagram of a method of calibrating components of the handheld surgical device of FIG. 1.

FIG. 80 is a flow diagram of a method 2000 of calibrating the articulation and firing functions of an adapter capable of attaching to a reload of the first type. A determination is made as to whether a reload is attached to the adapter at S2002. If a reload is attached to the adapter, calibration does not occur, an error screen is displayed, and a fault tone is sounded at S2004. If a reload is not attached to the adapter, a determination is made as to whether the software version stored in the adapter is compatible with the software of the power-pack at S2006. It will be appreciated that in another embodiment, calibration occurs regardless of whether a reload is attached, and hence in such an embodiment method 2000 begins from S2006. If the software version stored in the adapter is not compatible with the software of the power-pack, the power-pack updates the adapter software before calibration at S2008. At S2010, a determination is made as to whether the update is successful. If such update fails, firing calibration is performed but articulation calibration is not performed and entering the firing state is prohibited at S2012. If the software of the adapter and power-pack are found to be compatible at S2006 or the software update is successful at S2010, calibration of the articulation function and the firing function occurs at S2014. Calibration of the articulation function involves obtaining a reference position by driving the articulation shaft left until it stops at its mechanical limit and then returning the articulation shaft back to the center position. Calibration of the firing function is effected by obtaining a reference position by driving the firing shaft proximally until it stops at its mechanical limit, followed by returning the firing shaft distally to its home position.

After performing the firing and articulation calibrations, a determination is made as to whether the calibration has been successful at S2016. If either the firing or articulation calibration fails at S2016, no further operation is permitted until the adapter is replaced or reconnected and calibration is properly obtained at S2018. If calibration is successful, the adapter is operable in the firing state at S2020. If a reload is subsequently detected as removed at S2022, a request reload screen is displayed at S2024. A determination is made as to whether movement has occurred since a calibration of the adapter at S2026. If so, an articulation centered occurs at S2028. If no movement has occurred since the last calibration at S2026, the firing rod is not moved to a home position and articulation will not be centered at S2030. Returning to S2022, if the reload has not been removed, the adapter remains operable in firing state at S2020. Any buttons pressed during adapter calibration are ignored. In an embodiment, calibration occurs despite the battery having an insufficient charge. In another embodiment, calibration occurs even when the adapter has no uses remaining.

Figure 81:
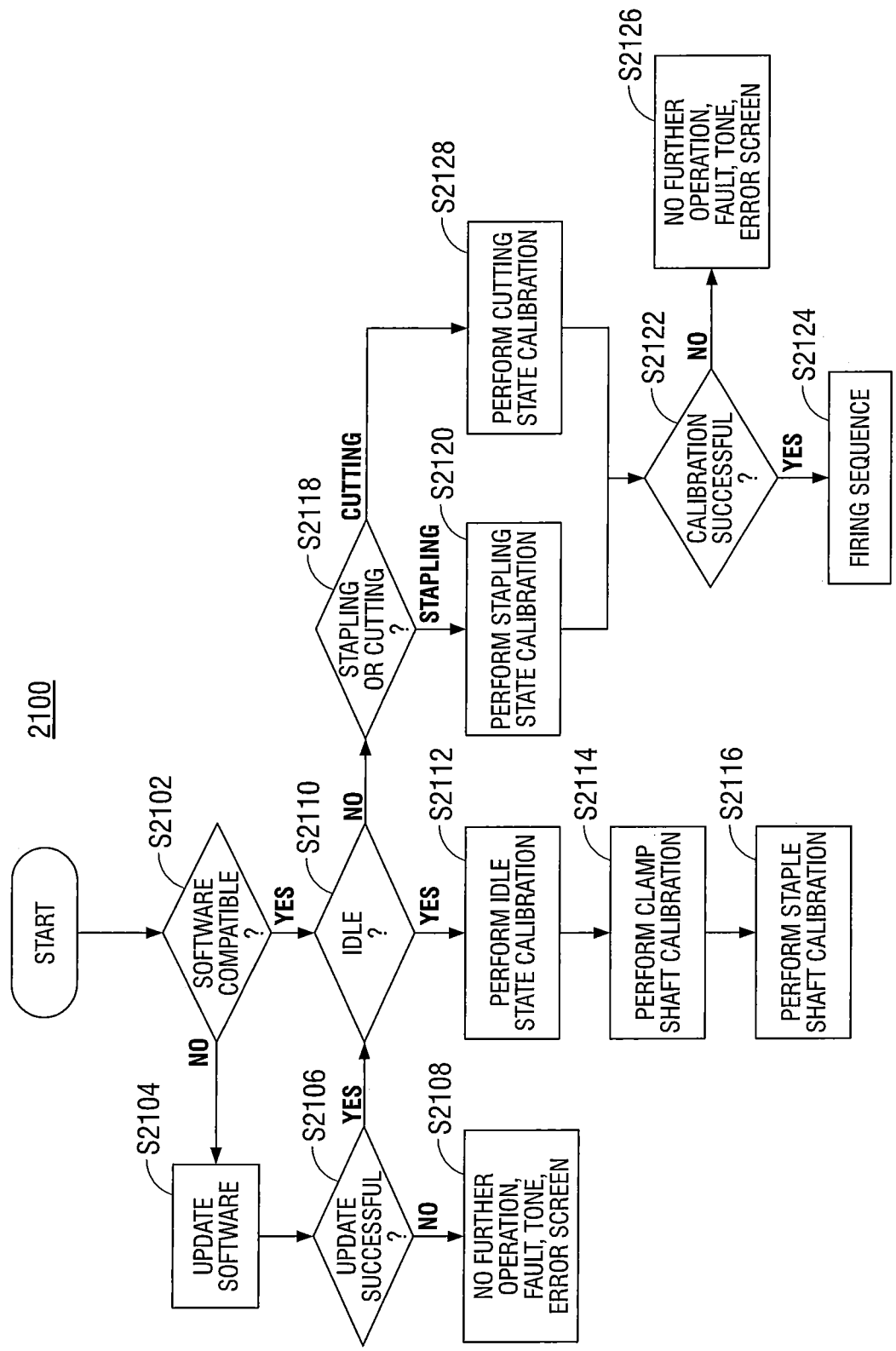
FIG. 81 is a flow diagram of another method of calibrating of the handheld surgical device of FIG. 1.

FIG. 81 is a flow diagram of a method 2100 of calibrating an adapter configured to attach to a loading unit of the second type. Here, calibration module 1120 includes a feature to perform idle state calibration, where the adapter is not in a stapling or cutting state. First, a determination is made as to whether the software of the adapter is compatible at S2102. If not, power-pack updates the adapter software before calibration at S2104. At S2106, a determination is made as to whether the update is successful. If such update fails, no further operation is allowed, a fault tone occurs, and an error screen is displayed at S2108.

If the software of the adapter is found to be compatible at S2102 or is successfully updated at S2106, a determination is made as to whether or not the adapter is idle at S2110. If the adapter is detected as in the idle state, the idle state calibration is performed at S2112. In particular, clamp shaft calibration is performed at S2114 by obtaining a reference position by driving the clamp shaft proximally until it stops at its mechanical limit. In response to an endstop, the clamp shaft is driven distally to its home position. In addition to the clamp shaft calibration, a staple shaft calibration is performed at S2116 by driving the staple shaft proximally until it stops at its mechanical limit. In response to an endstop, the staple shaft is driven distally to its home position. The pressing of any buttons during idle state calibration is ignored. Although the staple shaft calibration S2116 is described as being performed after the clamp shaft calibration S2114, it will be appreciated that the calibrations can be performed in no particular order. If calibration is not performed successfully, no further operation is possible until the adapter is removed, a fault tone occurs, and an "adapter error" screen is displayed.

Returning to S2110, if the adapter is not in the idle state, a determination is made as to whether the adapter is in a stapling state or a cutting state at S2118. If the adapter is in the stapling state, stapling state calibration is performed at S2120 by obtaining a reference position by driving the staple shaft proximally until it stops at its mechanical limit. The clamp and cut shaft calibration are not performed concurrently with the stapling state calibration, in an embodiment, and any button presses during stapling calibration are ignored.

If a cutting state is detected as S2118, calibration module 1120 performs a cutting state calibration at S2128. The cutting state calibration is performed by obtaining a reference position by driving the cut shaft proximally until it stops at its mechanical limit. The clamp and staple shaft calibration are not performed concurrently with the cutting state calibration, in an embodiment, and any button presses during stapling calibration are ignored.

A determination is made at S2122 as to whether the stapling state and cutting state calibrations have been performed successfully. If the stapling state calibration is successful, a firing sequence continues from stapling at S2124. If the cutting state calibration is successful, a firing sequence continues from cutting at S2124. If either the stapling state or cutting state calibration is not performed successfully, no further operation is possible until the adapter is removed, a fault tone occurs, and an "adapter error" screen is displayed at S2126.

As described briefly above, operation is effectuated by utilizing the buttons disposed on outer shell housing 10

Figure 82:
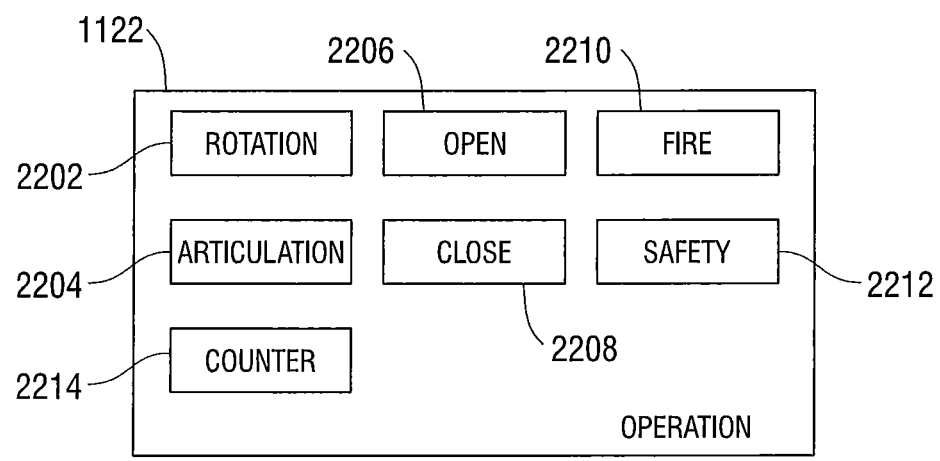
FIG. 82 is a block diagram of the operation module of the system hardware of FIG. 71.

(FIG. 1). Generally, operation module 1122 includes various modules to permit and inhibit various operations depending on the mode, status, state, and/or position of, among other components, the outer shell housing, the adapter, and the reload. The power-pack logs various data relating to the use and/or operation of the power-pack, the adapter, and the reload via communications transmitted across the 1-wire buses. Such data includes keystroke data relating to each of the buttons associated with the handheld, event logging data, fault and error data, knife position data, firing data, open/close data, etc. FIG. 82 is a block diagram of operation module 1122 including its various modules, according to an embodiment. Operation module 1122 includes rotation module 2202, articulation module 2204, open module 2206, close module 2208, firing module 2210, safety module 2212, and counter module 2214.

Rotation module 2202 causes rotation of the adapter in response to input received from pressing or actuating the appropriate button on surgical device 100 (FIG. 1), as detailed above. Additionally, rotation is permitted before attaching the adapter. In the event in which the adapter is not connected, the power-pack statistics screen is displayed on the display for a predetermined duration (e.g., 5 seconds) after all buttons are released. Rotation also occurs with or without a reload connected, even where there is insufficient battery charge to fire, where no power-pack or battery uses are remaining, where the reload has been used, or where the reload is in a clamp position. If another button is pressed during rotation, rotation is halted until the button is released. Further, if under an excess load is detected, rotation is stopped until the rotation button is released and re-depressed. Rotation is stopped in response to a detection of a motor velocity of 0 rotations per minute (RPMs) and remains stopped until button depression is detected again.

Articulation module 2204 articulates the reload. For example, in response to signals received from the appropriate button on surgical device 100 (FIG. 1), the reload is articulated either left or right. Articulation is permitted where there is insufficient battery charge to fire, where no power-pack or battery uses are remaining, where the reload is connected, or where the reload has been used and/or has no uses remaining. Depression of another button during articulation causes articulation to stop until the button is released. Articulation module 2204 includes an articulation current limit defined and set by adjusting the limit control on the motor controller circuit. The articulation current limit correlates to a maximum torque the motor will output. When a velocity threshold (e.g., of about −200 RPM±−5%) is reached or exceeded, articulation is stopped. Depression of any of the articulation buttons prior to attachment of the adapter and the reload does not cause articulation. In an embodiment, when the reload is in the clamp or closed position, articulation is effected at a slower rate as compared to articulation in the open position (e.g., 200 RPM±10 RPM).

Open module 2206 controls the opening of reload, in response to a pressing of the open button and determines whether opening operation continues or not based on various scenarios. For example, pressing the open button before the adapter or the reload is attached is ignored. During a reload opening, the reload remains open until the open button is released or the reload is fully opened. Opening is permitted with insufficient battery charge, with no power-pack or battery uses are remaining, or where the reload has been used. If another button is pressed during opening, opening is halted until the button is released. In an embodiment in which a trocar is used in conjunction with the surgical device, the trocar extends until fully extended, in response to an input received from a pressed open button. If the trocar is unable to be extended, no further operation is allowed, a fault tone occurs, and the "reload error" screen is displayed.

Close module 2208 controls the closing of reload, in response to a pressing of the close button and determines whether a close operation continues or not based on various detected or received inputs. In an embodiment, pressing the close button before the adapter or the loading is attached is ignored. Closing is effectuated until the close button is released or the fully closed position is achieved, at which time a tone is caused to be sounded. A closing operation is permitted where there is insufficient battery charge to fire, where no power-pack or battery uses are remaining, or where the reload has been used. If another button is pressed during closing, closing is halted until the button is released. A speed current limit is defined and set on the motor based on strain gauge. The speed current limit correlates to a maximum torque the motor will output. When a velocity threshold (e.g., of about −200 RPM±−5%) is reached or exceeded, the closing speed is reduced.

Firing module 2210 controls firing of staples in the reload by placing the reload in a firing state (during which staples can be fired) or out of the firing state (during which staples cannot be fired). In an embodiment, entering the firing state is only permitted when each of the following conditions is met:
 the outer shell housing has been installed, detected, verified as acceptable, and has not been used on a previous procedure;
 the adapter has been installed, detected, verified as acceptable, and calibrated successfully;
 the reload has been installed, verified as acceptable, passed encryption, can be marked as used, and has not been previously fired; and
 the battery level is sufficient for firing.

After the above conditions are met, and an input is detected indicating that the safety has been pressed, the power-pack enters the firing state and the attached the reload is marked as used its memory. While in in the firing state, pressing the close button advances the stapler pusher and knife to eject the staples through tissue and cut the stapled tissue, until the close button is released or the end stop of the reload is detected. If an endstop is detected, releasing and pressing the fire button again shall continue to advance the knife until the fire button is released or an end stop is again detected. Firing may continue upon re-actuation until forward progress is no longer made between end stops.

When the fire button is released and the open button is pressed twice, at any point during firing, the power-pack exits the firing state and the knife is automatically retracted to its home position. If the open button is pressed a single time during firing, i.e., while the fire button is pressed, firing stops. Firing does not continue until both the fire and open buttons have been released and the fire button is pressed again.

In the firing state, three speeds are provided: slow, normal, and fast. Rotation of adapter is inhibited in the firing state and, thus, the rotation buttons do not effect rotation. Rather, in the firing state, the rotation buttons are actuatable to increase or decrease the firing speed. The firing speed is initially set to normal. Articulation is also inhibited when in the firing state.

Loss of 1-wire communication between the power-pack and outer shell housing and/or adapter, or loss of communication regarding reload presence, does not interrupt firing.

However, such communication is checked after firing and retraction have been completed.

If the firing state is exited before any forward progress is made, reentering firing state does not increment the power-pack firing counter. Further, if the firing limit of the power-pack or adapter has been reached during an operation, the firing state remains accessible until the attached outer shell housing or adapter is removed.

If the firing state is exited before any forward progress is made, reentering firing state does not increment the power-pack firing counter. Further, if the firing limit of the power-pack or adapter has been reached during an operation, the firing state remains accessible until the attached outer shell housing or adapter is removed.

During the firing state, if linear sensor data no longer returns during a stapling sequence, stapling is interrupted, a fault tone occurs, and an "adapter error" screen is displayed. Additionally, if no movement of the staple shaft or the cut shaft is detected for a predetermined period of time (e.g., 1 second), stapling or cutting stops, a fault tone occurs, and a "reload error" screen is displayed. If an excessive load is detected during a stapling or cutting sequence, the stapling or cutting ceases, a fault tone occurs, and a "power-pack error" screen is displayed. In an embodiment in which an insufficient load is detected during a stapling or cutting sequence, the stapling or cutting ceases, a fault tone occurs, and a "power-pack error" screen is displayed.

Safety module 2212 controls entry of surgical device 100 (FIG. 1) into the firing state. Specifically, the firing state is entered when safety module 2212 detects that:
- an outer shell housing is installed, detected and supported;
- an adapter is installed detected, supported, and successfully calibrated;
- SULU or MULU is installed, detected, supported, and passed encryption;
- MULU cartridge is installed and has not been fired;
- SULU or MULU cartridge can be marked as used;
- reload is installed and detected;
- reload has not previously fired;
- battery level is sufficient for firing; and
- the outer shell housing has not been used on a previous procedure.

In an embodiment, a safety LED is lit when the power-pack is fully assembled and not in an error condition. When entering the firing state, a tone occurs and a "firing" screen is displayed, and the safety LED flashes until the firing state is exited. The firing state is exited when the open key is pressed, for example, twice, and a tone indicating exiting firing mode is displayed. The safety LED is not lit if the power-pack is unable to enter the firing state or when firing is complete.

Counter module 2214 maintains various counters that increment upon occurrence of specific events or conditions to indicate when certain components have reached the end of their usable lives. In particular, counter module 2214 maintains a power-pack procedure counter, a power-pack firing counter, an assumed autoclave counter for the adapter, and an adapter firing counter. These counters are in addition to the "used" markings assigned to outer shell housing and SULU, which are single-procedure-use components.

The power-pack procedure counter is stored in the memory of the power-pack. The power-pack procedure counter is incremented when the firing state is first entered after attaching a new outer shell housing to the power-pack. The power-pack procedure counter is not again incremented until the outer shell housing is removed a new outer shell housing installed and the firing state again entered, regardless of whether the firing state is entered multiple times while housed in a single outer shell housing. If the power-pack procedure counter cannot be incremented, power-pack can operate except in firing state, a fault tone occurs, and a "power-pack error" screen is displayed.

The power-pack firing counter is stored in the memory of the power-pack. The power-pack firing counter is incremented each time the firing state is entered except that, if the firing state is entered and no forward progress is made, reentering the firing state does not increment the power-pack firing counter. If the power-pack firing counter limit has been arrived at, power-pack is inhibited from entering the firing state. If the power-pack firing counter cannot be incremented, power-pack can operate except in firing state, a fault tone occurs, and a "power-pack error" screen is displayed.

The adapter autoclave counter is stored in the memory of the adapter and is incremented when the firing state is first entered after attaching a new outer shell housing. Due to the adapter being a reusable component, the adapter has a pre-set limit on usages, and it is assumed that the adapter is autoclaved prior to each procedure. If the adapter autoclave counter has already been incremented for a particular attached outer shell housing, it will not be incremented again until the outer shell housing is removed and replaced. If the adapter autoclave counter cannot be incremented, power-pack can operate except in firing state, a fault tone occurs, and an "adapter error" screen is displayed.

The adapter firing counter is stored in the memory of the adapter and is incremented when entering the firing state except that, if the firing state is entered and no forward progress is made, reentering the firing state does not increment the adapter firing counter. If the adapter firing counter limit has been arrived at, power-pack can operate except in firing state, a fault tone occurs, and a "power-pack error" screen is displayed.

In accordance with the present disclosure, in order to evaluate conditions that affect staple formation, such that a more intelligent stapling algorithm, may be developed, an electromechanical testing system may be used in place of a surgical device or stapler (e.g., powered hand held electromechanical instrument 100). The electromechanical testing system may be configured to deploy (e.g., fire) staples on ex vivo porcine stomach to measure forces and the resulting staple formation data may be collected. A sequential design of experiments may be utilized to assess the effects of four different factors, including speed of firing, tissue thickness, precompression time, and stapler length with respect to firing force and staple formation.

It was discovered that the firing force was affected by the speed of firing, a length of the reload (e.g., stapler length) and the tissue thickness. It was also discovered that staple formation was affected by the speed of firing and the tissue thickness. Finally, a correlation was discovered between the force on the electromechanical testing system and the staple formation; specifically, lower forces on the electromechanical testing system yielded better staple formation (e.g., fewer mis-formations, great complete formations, etc).

By slowing the speed of firing, particularly when relatively high forces are seen within a stapling system (e.g., surgical device or stapler, or powered hand held electromechanical instrument 100), the performance of the surgical device is improved It is contemplated that variations in the software are available to optimize output based on different reload types and in a variety of tissues with different characteristics (e.g., density, thickness, compliance, etc.). The intelligent stapling systems may be configured to continue to utilize clinical data and enhance device performance, leading to improved patient outcomes, by updating and/or modifying firing algorithms associated therewith.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A handheld electromechanical surgical device, comprising:
   a non-sterile power-pack including:
      at least one drive component, each drive component having a rotatable drive shaft extending therefrom;
      a main processor coupled to the at least one drive component and configured to control each drive component;
      a battery coupled to the main processor and the at least one drive component, the battery configured to power each drive component;
      an electrical receptacle coupled to the main processor; and
      at least one control interface coupled to the main processor, the at least one control interface actuatable to direct the main processor to control a functionality of at least one of the at least one drive component; and
   a sterile outer shell housing configured to removably encase the power-pack, the sterile outer shell housing defining a sterile barrier between the power-pack and an exterior of the outer shell housing when encased about the power-pack to enable use thereof in a surgical environment without breaking sterility, the outer shell housing including:
      a barrier plate assembly including:
         a coupler configured to transmit a rotation from the rotatable drive shaft of each drive component through the outer shell housing, wherein the coupler includes a plurality of rotatable coupling shafts, each rotatable coupling shaft including a proximal end configured to operably couple to a respective rotatable drive shaft to receive rotative forces therefrom, and a distal end projecting from the outer shell housing;
         at least one control button in operative registration with each of the at least one control interfaces such that actuation of the at least one control button actuates the at least one control interface in operative registration therewith; and
         a pass-through connector configured to transmit electrical communications from the electrical receptacle through the outer shell housing, wherein the pass-through connector includes a proximal end configured to operably couple to the electrical receptacle, and a distal end projecting out of the outer shell housing.

2. The handheld electromechanical surgical device according to claim 1, wherein the coupler transmits a rotation from the rotatable drive shaft of each drive component through the outer shell housing without breaking the sterile barrier.

3. The handheld electromechanical surgical device according to claim 1, wherein the at least one control button actuates the at least one control interface in operative registration therewith without breaking the sterile barrier.

4. The handheld electromechanical surgical device according to claim 1, wherein the pass-through connector transmits electrical communications from the electrical receptacle through the outer shell housing without breaking the sterile barrier.

5. The handheld electromechanical surgical device according to claim 1, further including an adapter assembly selectively connectable to the outer shell housing in operable engagement with the coupler and the pass-through connector to enable a rotation from the rotatable drive shaft of each drive component to be transmitted through the outer shell housing to the adapter assembly and to enable electrical communications from the electrical receptacle to be transmitted through the outer shell housing to the adapter assembly.

6. The handheld electromechanical surgical device according to claim 1, wherein the power-pack includes an inner housing enclosing each drive component, the main processor, and the battery, the inner housing including the at least one control interface and the electrical receptacle disposed thereon.

7. The handheld electromechanical surgical device according to claim 1, wherein the at least one drive component is a motor.

8. A handheld electromechanical surgical device, comprising:
   a non-sterile power-pack including at least one drive component having a rotatable drive shaft extending therefrom, a main processor coupled to each drive component, a battery coupled to the main processor and each drive component, an electrical receptacle coupled to the main processor, and at least one control interface coupled to the main processor;
   a sterile outer shell housing configured to removably encase the power-pack, the sterile outer shell housing defining a sterile barrier between the power-pack and an exterior of the outer shell housing when encased about the power-pack to enable use thereof in a surgical environment without breaking sterility, the outer shell housing including:
      a barrier plate assembly including:
         a coupler configured to transmit an output from each drive component through the outer shell housing, wherein the coupler includes a plurality of rotatable coupling shafts supported on the barrier plate assembly, each rotatable coupling shaft including a proximal end configured to operably couple to a respective rotatable drive shaft to receive rotative forces therefrom, and a distal end projecting from the outer shell housing; and
         a pass-through connector configured to transmit electrical communications from the electrical receptacle through the outer shell housing; and
      at least one control button in operative registration with each of the at least one control interfaces such that actuation of the at least one control button actuates the at least one control interface in operative registration therewith;
   an adapter assembly connected to the outer shell housing in operable engagement with the coupler and the pass-through connector to enable an output from each drive component to be transmitted through the outer shell housing to the adapter assembly and to enable electrical communications from the electrical receptacle to be transmitted through the outer shell housing to the adapter assembly; and a loading unit connected to the adapter assembly, wherein the adapter assembly is configured to effect an operation of the loading unit in response to an output from at least one of the at least one drive component of the power-pack and to enable electrical communication between the electrical receptacle of the power-pack and the loading unit.

9. The handheld electromechanical surgical device according to claim 8, wherein at least one of the loading unit and the adapter is selectively connectable.

10. The handheld electromechanical surgical device according to claim 8, wherein the coupler transmits an output from each drive component through the outer shell housing without breaking the sterile barrier.

11. The handheld electromechanical surgical device according to claim 8, wherein the at least one control button actuates the at least one control interface in operative registration therewith without breaking the sterile barrier.

12. The handheld electromechanical surgical device according to claim 8, wherein the pass-through connector transmits electrical communications from the electrical receptacle through the outer shell housing without breaking the sterile barrier.

13. The handheld electromechanical surgical device according to claim 8, wherein the at least one drive component includes a plurality of motors.

14. A handheld electromechanical surgical device, comprising:
- a non-sterile power-pack including:
  - at least one drive component, each drive component having a rotatable drive shaft extending therefrom;
  - a main processor coupled to the at least one drive component and configured to control each drive component;
  - a battery coupled to the main processor and the at least one drive component, the battery configured to power each drive component;
  - an electrical receptacle coupled to the main processor; and
  - at least one control interface coupled to the main processor, the at least one control interface actuatable to direct the main processor to control a functionality of at least one of the at least one drive component; and
- a sterile outer shell housing configured to removably encase the power-pack, the sterile outer shell housing defining a sterile barrier between the power-pack and an exterior of the outer shell housing when encased about the power-pack to enable use thereof in a surgical environment without breaking sterility, the outer shell housing including:
  - at least one control button in operative registration with each of the at least one control interfaces such that actuation of the at least one control button actuates the at least one control interface in operative registration therewith; and
  - a barrier plate assembly including:
    - a pass-through connector configured to transmit electrical communications from the electrical receptacle through the outer shell housing; and
    - a coupler configured to transmit a rotation from the rotatable drive shaft of each drive component through the outer shell housing, wherein the coupler includes a plurality of rotatable coupling shafts supported on the barrier plate assembly, each rotatable coupling shaft including a proximal end configured to operably couple to a respective rotatable drive shaft to receive rotative forces therefrom, and a distal end projecting from the outer shell housing.

15. The handheld electromechanical surgical device according to claim 14, wherein the coupler transmits a rotation from the rotatable drive shaft of each drive component through the outer shell housing without breaking the sterile barrier.

16. The handheld electromechanical surgical device according to claim 14, wherein the at least one control button actuates the at least one control interface in operative registration therewith without breaking the sterile barrier.

17. The handheld electromechanical surgical device according to claim 14, wherein the pass-through connector transmits electrical communications from the electrical receptacle through the outer shell housing without breaking the sterile barrier.

18. The handheld electromechanical surgical device according to claim 14, wherein the power-pack includes an inner housing enclosing each drive component, the main processor, and the battery, the inner housing including the at least one control interface and the electrical receptacle disposed thereon.

* * * * *